US009615213B2

(12) United States Patent
Tibbitts et al.

(10) Patent No.: US 9,615,213 B2
(45) Date of Patent: Apr. 4, 2017

(54) METHOD AND SYSTEM FOR CONTROLLING AND MODIFYING DRIVING BEHAVIORS

(71) Applicant: Katasi LLC, Niwot, CO (US)

(72) Inventors: Scott Ferrill Tibbitts, Niwot, CO (US); Franklin Tai, Playa Del Rey, CA (US); Ryan Tibbitts, Niwot, CO (US); Adam Stevenson, Boulder, CO (US); Malcolm Bruce Young, Lafayette, CO (US)

(*) Notice: Subject to any disclaimer, the term of this patent is extended or adjusted under 35 U.S.C. 154(b) by 0 days.

(21) Appl. No.: 14/139,698

(22) Filed: Dec. 23, 2013

(65) Prior Publication Data
US 2014/0113619 A1    Apr. 24, 2014

Related U.S. Application Data

(63) Continuation-in-part of application No. 13/612,748, filed on Sep. 12, 2012, which is a continuation-in-part
(Continued)

(51) Int. Cl.
*H04Q 7/20* (2006.01)
*H04W 4/02* (2009.01)
(Continued)

(52) U.S. Cl.
CPC ............ *H04W 4/027* (2013.01); *G07C 5/008* (2013.01); *G07C 5/0808* (2013.01); *H04K 3/415* (2013.01);
(Continued)

(58) Field of Classification Search
CPC ...... H04W 4/027; H04W 48/04; G07C 5/008; G07C 5/0808; H04B 5/0062; H04K 2203/22; H04K 3/415; H04K 3/45
(Continued)

(56) References Cited

U.S. PATENT DOCUMENTS 4,297,539 A    10/1981  Fairbanks
4,908,611 A     3/1990  Iino
(Continued)

FOREIGN PATENT DOCUMENTS

EP    0955210    10/1999
EP    0940051     8/2007
(Continued)

OTHER PUBLICATIONS

Notice of Allowance for U.S. Appl. No. 13/612,748, mailed Mar. 1, 2016.
(Continued)

*Primary Examiner* — Tan H Trinh
(74) *Attorney, Agent, or Firm* — Aspire IP; Scott J. Hawranek

(57) ABSTRACT

Disclosed herein is a method and system for detecting, monitoring and/or controlling one or more of mobile services for a mobile communication device (also referred to herein as a Controllable Mobile Device or CMD), and in particular, when the device is being used and the vehicle, operated by the user of the device, is moving. In addition, one aspect of the invention generally relates to a method and system for modifying a user's driving behaviors, in particular to a system and method for modifying a user's unsafe driving behaviors, e.g., using one or more services of a controllable mobile device while driving, by providing a score to the user rating indicating that they are using a mobile device in a distracting way, or driving in a manner that indicates that they are distracted.

76 Claims, 23 Drawing Sheets

Related U.S. Application Data of application No. 12/841,077, filed on Jul. 21, 2010, now Pat. No. 8,761,821.

(60) Provisional application No. 61/267,064, filed on Dec. 6, 2009, provisional application No. 61/227,404, filed on Jul. 21, 2009, provisional application No. 61/533,358, filed on Sep. 12, 2011, provisional application No. 61/745,349, filed on Dec. 21, 2012.

(51) Int. Cl.
| | |
|---|---|
| *H04K 3/00* | (2006.01) |
| *H04W 48/04* | (2009.01) |
| *G07C 5/00* | (2006.01) |
| *G07C 5/08* | (2006.01) |
| *H04B 5/00* | (2006.01) |

(52) U.S. Cl.
CPC .............. *H04K 3/45* (2013.01); *H04W 48/04* (2013.01); *H04B 5/0062* (2013.01); *H04K 2203/22* (2013.01)

(58) Field of Classification Search
USPC ....... 455/517, 569.2, 410, 411, 456.4, 456.3, 455/556.1, 456.1, 418, 404; 705/14.58, 4, 705/10, 1; 340/439, 936, 7.24, 903; 342/357.07, 357.1; 707/104.1; 701/29.6, 701/1, 36, 117, 51, 99
See application file for complete search history.

(56) References Cited

U.S. PATENT DOCUMENTS

| | | |
|---|---|---|
| 5,146,407 A | 9/1992 | Motohashi |
| 5,148,153 A | 9/1992 | Haymond |
| 5,191,312 A | 3/1993 | Altmann et al. |
| 5,504,482 A | 4/1996 | Schreder |
| 5,515,364 A | 5/1996 | Fague |
| 5,519,410 A | 5/1996 | Smalanskas et al. |
| 5,541,572 A | 7/1996 | Okamoto et al. |
| 5,548,764 A | 8/1996 | Duley et al. |
| 5,548,800 A | 8/1996 | Olds et al. |
| 5,749,052 A | 5/1998 | Hidem et al. |
| 5,815,407 A | 9/1998 | Huffman et al. |
| 5,842,124 A | 11/1998 | Kenagy et al. |
| 5,852,775 A | 12/1998 | Hidary |
| 5,862,476 A | 1/1999 | Hasegawa |
| 5,864,757 A | 1/1999 | Parker |
| 5,887,258 A | 3/1999 | Lemozit et al. |
| 5,890,067 A | 3/1999 | Chang et al. |
| 5,949,345 A | 9/1999 | Beckert et al. |
| 5,963,550 A | 10/1999 | Hirata et al. |
| 5,991,749 A | 11/1999 | Morrill, Jr. |
| 6,011,973 A | 1/2000 | Valentine et al. |
| 6,023,232 A | 2/2000 | Eitzenberger |
| 6,028,537 A | 2/2000 | Suman et al. |
| 6,085,096 A | 7/2000 | Nakamura |
| 6,088,586 A | 7/2000 | Haverty |
| 6,122,486 A | 9/2000 | Tanaka et al. |
| 6,122,682 A | 9/2000 | Andrews |
| 6,131,045 A | 10/2000 | Iwata |
| 6,134,447 A | 10/2000 | Havinis et al. |
| 6,154,172 A | 11/2000 | Piccionelli et al. |
| 6,198,927 B1 | 3/2001 | Wright et al. |
| 6,208,866 B1 | 3/2001 | Rouhollahzadeh et al. |
| 6,222,458 B1 | 4/2001 | Harris |
| 6,225,897 B1 | 5/2001 | Doyle et al. |
| 6,230,017 B1 | 5/2001 | Andersson et al. |
| 6,233,448 B1 | 5/2001 | Alperovich et al. |
| 6,256,503 B1 | 7/2001 | Stephens |
| 6,256,558 B1 | 7/2001 | Sugiura et al. |
| 6,262,657 B1 | 7/2001 | Okuda et al. |
| 6,263,190 B1 | 7/2001 | Mamori et al. |
| 6,285,868 B1 | 9/2001 | LaDue |
| 6,298,131 B1 | 10/2001 | Veschi |
| 6,311,078 B1 | 10/2001 | Hardouin |
| 6,314,282 B1 | 11/2001 | Weber et al. |
| 6,343,212 B1 | 1/2002 | Weber et al. |
| 6,343,213 B1 | 1/2002 | Steer et al. |
| 6,353,778 B1 | 3/2002 | Brown |
| 6,356,812 B1 | 3/2002 | Cragun |
| 6,389,287 B1 | 5/2002 | Smith et al. |
| 6,393,301 B1 | 5/2002 | Oda |
| 6,418,309 B1 | 7/2002 | Moon et al. |
| 6,421,544 B1 | 7/2002 | Sawada |
| 6,438,385 B1 | 8/2002 | Heinonen et al. |
| 6,456,822 B1 | 9/2002 | Gofman et al. |
| 6,459,891 B1 | 10/2002 | Whinnett et al. |
| 6,496,703 B1 | 12/2002 | da Silva |
| 6,496,709 B2 | 12/2002 | Murray |
| 6,505,046 B1 | 1/2003 | Baker |
| 6,526,275 B1 | 2/2003 | Calvert |
| 6,546,257 B1 | 4/2003 | Stewart |
| 6,556,810 B1 | 4/2003 | Suzuki |
| 6,580,973 B2 | 6/2003 | Leivian et al. |
| 6,594,483 B2 | 7/2003 | Nykanen et al. |
| 6,600,975 B2 | 7/2003 | Moriguchi et al. |
| 6,643,517 B1 | 11/2003 | Steer |
| 6,647,257 B2 | 11/2003 | Owensby |
| 6,647,269 B2 | 11/2003 | Hendrey et al. |
| 6,650,894 B1 | 11/2003 | Berstis et al. |
| 6,678,516 B2 | 1/2004 | Nordman et al. |
| 6,687,497 B1 | 2/2004 | Parvulescu et al. |
| 6,687,506 B1 | 2/2004 | Girod |
| 6,690,940 B1 | 2/2004 | Brown et al. |
| 6,701,158 B2 | 3/2004 | Moreth |
| 6,714,519 B2 | 3/2004 | Luzzatti et al. |
| 6,721,542 B1 | 4/2004 | Anttila et al. |
| 6,728,542 B2 | 4/2004 | Meda |
| 6,731,925 B2 | 5/2004 | Naboulsi |
| 6,771,946 B1 | 8/2004 | Oyaski |
| 6,807,435 B2 | 10/2004 | Yamashita |
| 6,816,731 B1 | 11/2004 | Maruyama |
| 6,819,928 B1 | 11/2004 | Hokao |
| 6,832,093 B1 | 12/2004 | Ranta |
| 6,847,822 B1 | 1/2005 | Dennison et al. |
| 6,885,869 B2 | 4/2005 | Raith |
| 6,922,571 B1 | 7/2005 | Kinoshita |
| 6,925,105 B1 | 8/2005 | Partyka |
| 6,934,547 B2 | 8/2005 | Suzuki |
| 6,961,561 B2 | 11/2005 | Himmel et al. |
| 6,973,333 B1 | 12/2005 | O'Neil |
| 6,978,136 B2 | 12/2005 | Jenniges et al. |
| 7,003,525 B1 | 2/2006 | Horvitz et al. |
| 7,006,793 B2 | 2/2006 | Himmel et al. |
| 7,015,831 B2 | 3/2006 | Karlsson et al. |
| 7,035,828 B2 | 4/2006 | Ketonen et al. |
| 7,039,425 B1 | 5/2006 | Mazawa et al. |
| 7,064,656 B2 | 6/2006 | Belcher et al. |
| 7,072,753 B2 | 7/2006 | Eberle et al. |
| 7,107,058 B2 | 9/2006 | Inoguchi et al. |
| 7,110,749 B2 | 9/2006 | Zellner et al. |
| 7,116,992 B1 | 10/2006 | Tsunehara et al. |
| 7,123,874 B1 | 10/2006 | Brennan |
| 7,149,627 B2 | 12/2006 | Ockerse et al. |
| 7,181,228 B2 | 2/2007 | Boesch |
| 7,181,229 B2 | 2/2007 | Singh et al. |
| 7,187,953 B2 | 3/2007 | Bauchot et al. |
| 7,206,615 B2 | 4/2007 | Ochi et al. |
| 7,242,946 B2 | 7/2007 | Kokkonen et al. |
| 7,260,390 B1 | 8/2007 | Skinner et al. |
| 7,269,627 B2 | 9/2007 | Knauerhase |
| 7,319,696 B2 | 1/2008 | Inoue et al. |
| 7,330,895 B1 | 2/2008 | Horvitz |
| 7,343,148 B1 | 3/2008 | O'Neil |
| 7,359,713 B1 | 4/2008 | Tiwari |
| 7,359,714 B2 | 4/2008 | Parupudi et al. |
| 7,369,845 B2 | 5/2008 | Keohane et al. |
| 7,394,791 B2 | 7/2008 | Proctor, Jr. |
| 7,395,046 B2 | 7/2008 | Hossain et al. |
| 7,400,891 B2 | 7/2008 | Aaron |
| 7,403,785 B2 | 7/2008 | Daniels et al. |
| 7,430,724 B2 | 9/2008 | Othmer |

(56) References Cited

U.S. PATENT DOCUMENTS

| | | |
|---|---|---|
| 7,437,752 B2 | 10/2008 | Heard et al. |
| 7,471,929 B2 | 12/2008 | Fujioka et al. |
| 7,474,264 B2 | 1/2009 | Bolduc et al. |
| 7,477,135 B2 | 1/2009 | Belcher et al. |
| 7,505,784 B2 | 3/2009 | Barbera |
| 7,619,507 B2 | 11/2009 | Santos et al. |
| 7,640,101 B2 | 12/2009 | Pair et al. |
| 7,734,315 B2 * | 6/2010 | Rathus et al. ............. 455/569.2 |
| 7,738,831 B2 | 6/2010 | Nath et al. |
| 7,813,741 B2 | 10/2010 | Hendrey et al. |
| 7,903,029 B2 | 3/2011 | Dupray |
| 7,979,057 B2 | 7/2011 | Ortiz et al. |
| 8,000,689 B2 | 8/2011 | Featherstone et al. |
| 8,045,976 B2 | 10/2011 | Kiddie et al. |
| 8,103,292 B2 | 1/2012 | Kelly et al. |
| 8,131,205 B2 | 3/2012 | Rosen |
| 8,160,560 B2 | 4/2012 | Geyer et al. |
| 8,224,353 B2 | 7/2012 | Wright et al. |
| 8,285,308 B1 | 10/2012 | Wright et al. |
| 8,359,005 B2 | 1/2013 | Smith et al. |
| 8,560,161 B1 * | 10/2013 | Kator et al. ................. 701/29.6 |
| 8,761,821 B2 | 6/2014 | Tibbitts et al. |
| 8,787,936 B2 | 7/2014 | Tibbitts et al. |
| 9,098,859 B2 * | 8/2015 | Moinuddin ............ G06Q 30/02 |
| 2001/0050614 A1 | 12/2001 | Yang |
| 2002/0032510 A1 | 3/2002 | Turnbull |
| 2002/0039896 A1 | 4/2002 | Brown |
| 2002/0049069 A1 | 4/2002 | Johnson |
| 2002/0065112 A1 | 5/2002 | Endoh et al. |
| 2002/0128000 A1 | 9/2002 | do Nascimento, Jr. |
| 2002/0198004 A1 | 12/2002 | Heie et al. |
| 2002/0198005 A1 | 12/2002 | Hilton et al. |
| 2003/0129995 A1 | 7/2003 | Niwa et al. |
| 2003/0137408 A1 | 7/2003 | Breiner |
| 2003/0143988 A1 | 7/2003 | Jamadagni |
| 2004/0092253 A1 | 5/2004 | Simonds et al. |
| 2004/0153362 A1 * | 8/2004 | Bauer et al. ..................... 705/10 |
| 2004/0156333 A1 | 8/2004 | Bush |
| 2004/0198332 A1 | 10/2004 | Lundsgaard |
| 2004/0203766 A1 | 10/2004 | Jenniges et al. |
| 2004/0203900 A1 | 10/2004 | Cedervall et al. |
| 2004/0248589 A1 | 12/2004 | Gwon et al. |
| 2004/0251745 A1 | 12/2004 | Baruque Lopez et al. |
| 2004/0253963 A1 | 12/2004 | Park et al. |
| 2005/0037760 A1 | 2/2005 | Maruyama |
| 2005/0070298 A1 | 3/2005 | Caspi et al. |
| 2005/0096026 A1 | 5/2005 | Chitrapu et al. |
| 2005/0119002 A1 | 6/2005 | Bauchot et al. |
| 2005/0153680 A1 | 7/2005 | Yoshioka et al. |
| 2005/0170850 A1 | 8/2005 | Edwards et al. |
| 2005/0184860 A1 | 8/2005 | Taruki et al. |
| 2005/0255874 A1 | 11/2005 | Stewart-Baxter et al. |
| 2005/0261011 A1 | 11/2005 | Scott |
| 2005/0264404 A1 | 12/2005 | Franczyk et al. |
| 2006/0040640 A1 | 2/2006 | Thompson et al. |
| 2006/0046765 A1 | 3/2006 | Kogure |
| 2006/0061988 A1 | 3/2006 | Johnson et al. |
| 2006/0099940 A1 | 5/2006 | Pfleging et al. |
| 2006/0099959 A1 | 5/2006 | Staton et al. |
| 2006/0099969 A1 | 5/2006 | Staton et al. |
| 2006/0104297 A1 | 5/2006 | Buyukkoc et al. |
| 2006/0116807 A1 | 6/2006 | Hijikata |
| 2006/0136131 A1 | 6/2006 | Dugan et al. |
| 2006/0136291 A1 | 6/2006 | Morita et al. |
| 2006/0148490 A1 | 7/2006 | Bates et al. |
| 2006/0211412 A1 | 9/2006 | Vance |
| 2006/0217130 A1 | 9/2006 | Rowitch et al. |
| 2006/0229058 A1 | 10/2006 | Rosenberg |
| 2006/0246918 A1 | 11/2006 | Fok et al. |
| 2006/0293842 A1 | 12/2006 | Casino |
| 2007/0016643 A1 | 1/2007 | Boss et al. |
| 2007/0072616 A1 | 3/2007 | Irani |
| 2007/0082678 A1 | 4/2007 | Himmelstein |
| 2007/0088823 A1 | 4/2007 | Fowler et al. |
| 2007/0257815 A1 * | 11/2007 | Gunderson et al. ........... 340/903 |
| 2007/0271234 A1 | 11/2007 | Ravikiran |
| 2007/0287420 A1 | 12/2007 | Kirke |
| 2007/0287474 A1 | 12/2007 | Jenkins et al. |
| 2008/0061988 A1 | 3/2008 | Mock et al. |
| 2008/0064446 A1 | 3/2008 | Camp et al. |
| 2008/0075056 A1 | 3/2008 | Thome |
| 2008/0139183 A1 | 6/2008 | Keohane et al. |
| 2008/0183388 A1 | 7/2008 | Goodrich |
| 2008/0214211 A1 | 9/2008 | Lipovski |
| 2008/0215209 A1 * | 9/2008 | Ikeda et al. ..................... 701/36 |
| 2008/0252487 A1 * | 10/2008 | McClellan et al. ........... 340/936 |
| 2008/0268769 A1 | 10/2008 | Brown et al. |
| 2008/0275604 A1 | 11/2008 | Perry |
| 2008/0294302 A1 | 11/2008 | Basir |
| 2008/0294690 A1 * | 11/2008 | McClellan et al. ........ 707/104.1 |
| 2009/0002147 A1 | 1/2009 | Bloebaum et al. |
| 2009/0004968 A1 | 1/2009 | Miyake |
| 2009/0029675 A1 * | 1/2009 | Steinmetz et al. ............ 455/410 |
| 2009/0082951 A1 | 3/2009 | Graessley |
| 2009/0085728 A1 | 4/2009 | Catten et al. |
| 2009/0085744 A1 | 4/2009 | Sellin et al. |
| 2009/0098855 A1 * | 4/2009 | Fernandez et al. ........... 455/410 |
| 2009/0111422 A1 | 4/2009 | Bremer et al. |
| 2009/0163243 A1 | 6/2009 | Barbera |
| 2009/0177336 A1 | 7/2009 | McClellan et al. |
| 2009/0309787 A1 | 12/2009 | Gildea |
| 2010/0033312 A1 | 2/2010 | Chauncey et al. |
| 2010/0069018 A1 | 3/2010 | Simmons et al. |
| 2010/0087984 A1 | 4/2010 | Joseph |
| 2010/0204877 A1 | 8/2010 | Schwartz |
| 2010/0207787 A1 | 8/2010 | Catten et al. |
| 2010/0210254 A1 | 8/2010 | Kelly et al. |
| 2010/0216509 A1 | 8/2010 | Riemer et al. |
| 2010/0233959 A1 | 9/2010 | Kelly et al. |
| 2010/0238009 A1 * | 9/2010 | Cook et al. ................... 340/439 |
| 2010/0250021 A1 * | 9/2010 | Cook et al. ....................... 701/1 |
| 2010/0323657 A1 | 12/2010 | Barnard et al. |
| 2011/0009107 A1 | 1/2011 | Guba et al. |
| 2011/0065456 A1 | 3/2011 | Brennan et al. |
| 2011/0077028 A1 * | 3/2011 | Wilkes, III ............ B60W 50/14 455/456.3 |
| 2011/0092159 A1 | 4/2011 | Park et al. |
| 2011/0151842 A1 | 6/2011 | Olincy et al. |
| 2011/0151852 A1 | 6/2011 | Olincy et al. |
| 2011/0231628 A1 * | 9/2011 | Gelter et al. .................. 711/171 |
| 2011/0263240 A1 | 10/2011 | Featherstone et al. |
| 2011/0294520 A1 * | 12/2011 | Zhou et al. ................. 455/456.1 |
| 2012/0015690 A1 | 1/2012 | Miao |
| 2012/0058750 A1 | 3/2012 | Olincy et al. |
| 2012/0058755 A1 | 3/2012 | Olincy et al. |
| 2012/0058756 A1 | 3/2012 | Olincy et al. |
| 2012/0071151 A1 | 3/2012 | Abramson et al. |
| 2012/0089423 A1 * | 4/2012 | Tamir et al. ....................... 705/4 |
| 2012/0101855 A1 * | 4/2012 | Collins .................. G06Q 40/08 705/4 |
| 2012/0108219 A1 | 5/2012 | Kiddie et al. |
| 2012/0109692 A1 * | 5/2012 | Collins .................. G06Q 30/00 705/4 |
| 2012/0123806 A1 * | 5/2012 | Schumann et al. ................ 705/4 |
| 2012/0129545 A1 | 5/2012 | Hodis et al. |
| 2012/0215594 A1 * | 8/2012 | Gravelle .............. G07B 15/063 705/13 |
| 2012/0226413 A1 | 9/2012 | Chen et al. |
| 2012/0231779 A1 * | 9/2012 | Rathus et al. ................. 455/418 |
| 2012/0264409 A1 | 10/2012 | Geyer et al. |
| 2012/0268235 A1 | 10/2012 | Farhan et al. |
| 2012/0323690 A1 | 12/2012 | Michael |
| 2013/0017816 A1 | 1/2013 | Talty et al. |
| 2013/0019262 A1 | 1/2013 | Bhatia et al. |
| 2013/0023229 A1 | 1/2013 | Messerly |
| 2013/0084847 A1 | 4/2013 | Tibbitts et al. |
| 2013/0238365 A1 * | 9/2013 | Nepomuceno ......... G06Q 40/08 705/4 |
| 2013/0316311 A1 * | 11/2013 | England ............... G09B 19/167 434/65 |
| 2014/0095305 A1 * | 4/2014 | Armitage ........... G06Q 30/0251 705/14.49 |

(56) References Cited

U.S. PATENT DOCUMENTS

| | | | | |
|---|---|---|---|---|
| 2014/0142989 | A1* | 5/2014 | Grosso | G06Q 40/00 705/4 |
| 2014/0236695 | A1* | 8/2014 | Shvarts | G06Q 30/0224 705/14.25 |
| 2014/0272847 | A1* | 9/2014 | Grimes | G09B 19/00 434/236 |
| 2014/0302834 | A1* | 10/2014 | Jones | H04W 4/027 455/418 |
| 2014/0322676 | A1* | 10/2014 | Raman | G09B 19/167 434/65 |
| 2014/0364108 | A1 | 12/2014 | Tibbitts et al. | |
| 2015/0081404 | A1* | 3/2015 | Basir | G06Q 30/0207 705/14.1 |
| 2015/0106289 | A1* | 4/2015 | Basir | G07C 5/08 705/325 |
| 2015/0120336 | A1* | 4/2015 | Grokop | B60W 40/09 705/4 |

FOREIGN PATENT DOCUMENTS

| | | |
|---|---|---|
| EP | 1931109 | 11/2011 |
| GB | 2344971 | 6/2000 |
| GB | 2362020 | 11/2001 |
| JP | 07-245782 | 9/1995 |
| JP | 10-200961 | 7/1998 |
| JP | 10-256979 | 9/1998 |
| JP | 10-294970 | 11/1998 |
| JP | 11-004190 | 1/1999 |
| JP | 11-088954 | 3/1999 |
| JP | 2000-349895 | 12/2000 |
| JP | 2006-304034 | 11/2006 |
| KR | 20010097024 | 11/2001 |
| WO | WO 98/34412 | 8/1998 |
| WO | WO 99/55102 | 10/1999 |
| WO | WO 2006/070253 | 7/2006 |
| WO | WO 2008/109477 | 9/2008 |

OTHER PUBLICATIONS

Official Action for U.S. Appl. No. 14/452,500, mailed Feb. 11, 2016.
U.S. Appl. No. 14/452,500, filed Aug. 5, 2014, Brown et al.
Fetter et al., "Digital Cellular Telephone Interaction with Implantable Cardioverter-Defibrillators," JACC vol. 31, No. 3, Mar. 1998, pp. 623-628.
Hahn et al., "The Economics of Regulating Cellular Phones in Vehicles," Working paper from AEI-Brookings Joint Center for Regulatory Studies, Oct. 1999, pp. 1-44.
Complaint for Declaratory Judgment and Jury Demand filed in U.S. District Court for the District of Colorado, Case No. 1:12-CV-03306-PAB-KLM, on Dec. 19, 2012, 20 pages.
Report on the Filing or Determination of an Action Regarding a Patent or Trademark filed in U.S. District Court for the District of Colorado, Case No. 1:12-CV-03306-PAB-KLM, on Dec. 19, 2012, 1 page.
Civil Cover Sheet filed in U.S. District Court for the District of Colorado, Case No. 1:12-CV-03306-PAB-KLM, on Dec. 19, 2012, 1 page.
Plaintiff Aegis Mobility, Inc.'s Corporate Disclosure Statement filed in U.S. District Court for the District of Colorado, Case No. 1:12-CV-03306-PAB-KLM, on Dec. 19, 2012, 1 page.
Summons in a Civil Action issued to Katasi, LLC in U.S. District Court for the District of Colorado, Case No. 1:12-CV-03306-PAB-KLM, on Dec. 19, 2012, 1 page.
Summons in a Civil Action issued to obdEDGE, LLC in U.S. District Court for the District of Colorado, Case No. 1:12-CV-03306-PAB-KLM, on Dec. 19, 2012, 1 page.
Report on the Filing or Determination of an Action Regarding a Patent or Trademark filed in U.S. District Court for the District of Colorado, Case No. 1:12-CV-03306-PAB-KLM, on Dec. 20, 2012, 3 pages.

Minute Order issued by the U.S. District Court for the District of Colorado, Case No. 1:12-CV-03306-PAB-KLM, on Jan. 2, 2013, 9 pages.
Minute Order issued by the U.S. District Court for the District of Colorado, Case No. 1:12-CV-03306-PAB-KLM, on Mar. 12, 2013, 1 page.
Joint Stipulation to Extend Time to Respond to Complaint Pursuant to D.C. Colo.LCivR 6.1(A) filed in U.S. District Court for the District of Colorado, Case No. 1:12-CV-03306-PAB-KLM, on Mar. 26, 2013, 2 pages.
Defendant Katasi, LLC 's Corporate Disclosure Statement filed in U.S. District Court for the District of Colorado, Case No. 1:12-CV-03306-PAB-KLM, on Apr. 18, 2013, 2 pages.
Defendant Obedge, LLC's Notice of Related Cases filed in U.S. District Court for the District of Colorado, Case No. 1:12-CV-03306-PAB-KLM, on Apr. 18, 2013, 2 pages.
Unopposed Motion for Extension of Time to Respond to Complaint filed in U.S. District Court for the District of Colorado, Case No. 1:12-CV-03306-PAB-KLM, on Apr. 18, 2013, 5 pages.
Minute Order issued by the U.S. District Court for the District of Colorado, Case No. 1:12-CV-03306-PAB-KLM, on Apr. 22, 2013, 1 page.
Answer of Katasi LLC's filed in U.S. District Court for the District of Colorado, Case No. 1:12-CV-03306-PAB-KLM, on May 8, 2013, 3 pages.
Defendant Obedge,LLC Cellcontrol's unopposed motion for extension of time to respond to complaint filed in U.S. District Court for the District of Colorado, Case No. 1:12-CV-03306-PAB-KLM, on May 9, 2013, 3 pages.
Minute order filed in U.S. District Court for the District of Colorado, Case No. 1:12-CV-03306-PAB-KLM, on May 10, 2013, 1 page.
Defendant Obdedge, LLC , d/b/a Cellcontrol's Unopposed Motion for Extension of Time to Respond to Complaint filed in U.S. District Court for the District of Colorado, Case No. 1:12-CV-03306-PAB-KLM, on May 23, 2013, 3 pages.
Joint Motion to Vacate and Re-set Date for Scheduling Conference and Date for Filing of Proposed Scheduling Order filed in U.S. District Court for the District of Colorado, Case No. 1:12-CV-03306-PAB-KLM, on May 24, 2013, 5 pages.
Minute Order issued by the U.S. District Court for the District of Colorado, Case No. 1:12-CV-03306-PAB-KLM, on May 28, 2013, 1 page.
Joint Stipulation of Dismissal filed in U.S. District Court for the District of Colorado, Case No. 1:12-CV-03306-PAB-KLM, on May 31, 2013, 17 pages.
International Search Report for International (PCT) Patent Application No. PCT/US2010/042793, mailed Sep. 10, 2010.
Written Opinion for International (PCT) Patent Application No. PCT/US2010/042793, mailed Sep. 10, 2010.
International Preliminary Report on Patentability for International (PCT) Patent Application No. PCT/US2010/042793, mailed Feb. 2, 2012.
Official Action for U.S. Appl. No. 12/841,077, mailed May 3, 2012.
Notice of Allowance for U.S. Appl. No. 12/841,077, mailed Oct. 31, 2012.
Supplemental Notice of Allowability for U.S. Appl. No. 12/841,077, mailed Dec. 2, 2012.
Notice of Allowance for U.S. Appl. No. 12/841,077, mailed Feb. 11, 2014.
Official Action for U.S. Appl. No. 13/386,643, mailed Apr. 12, 2013.
Notice of Allowance for U.S. Appl. No. 13/386,643, mailed Dec. 17, 2013.
Official Action for U.S. Appl. No. 14/336,282, mailed Sep. 28, 2015.
Official Action for U.S. Appl. No. 13/612,748, mailed Dec. 23, 2013.
Official Action for U.S. Appl. No. 13/612,748, mailed Dec. 26, 2014.
Official Action for U.S. Appl. No. 13/612,748, mailed Jul. 24, 2015.
Official Action for U.S. Appl. No. 14/452,500, mailed Jul. 11, 2016.
Notice of Allowance for U.S. Appl. No. 14/336,282, mailed May 11, 2016.

(56) References Cited

OTHER PUBLICATIONS

Complaint filed in United States District Court for the District of Colorado, Case No. 1:16-cv-439 on Feb. 24, 2016, 21 pages.
Summons to Obdedge, LLC d/b/a Cellcontrol filed in United States District Court for the District of Colorado, Case No. 1:16-cv-439 on Feb. 24, 2016, 2 pages.
Civil Cover Sheet filed in United States District Court for the District of Colorado, Case No. 1:16-cv-439 on Feb. 24, 2016, 2 pages.
Notice of Entry of Appearance of Yiu Au filed in United States District Court for the District of Colorado, Case No. 1:16-cv-439 on Feb. 24, 2016, 2 pages.
Notice of Entry of Appearance of Jeff Massey Au filed in United States District Court for the District of Colorado, Case No. 1:16-cv-439 on Feb. 24 2016, 2 pages.
Order to Show Cause Issued by United States District Court for the District of Colorado, Case No. 1:16-cv-439 on Feb. 26, 2016, 3 pages.
Motion to Dismiss without Prejudice filed in United States District Court for the District of Colorado, Case No. 1:16-cv-439 on Mar. 7, 2016, 1 page.

\* cited by examiner

METHOD AND SYSTEM FOR CONTROLLING AND MODIFYING DRIVING BEHAVIORS

This application claims the benefit under 35 U.S.C. §119(e) of U.S. Provisional Patent Application No. 61/745,349 filed Dec. 21, 2012, this application is also a continuation-in-part of U.S. patent application Ser. No. 13/612,748, filed Sep. 12, 2012 (now U.S. Pat. No. 9,386,447), which claims the benefit under U.S.C. §119(e) of U.S. Provisional Patent Application No. 61/533,358 filed Sep. 12, 2011, and which is a continuation-in-part of U.S. patent application Ser. No. 12/841,077, filed Jul. 21, 2010 (now U.S. Pat. No. 8,761,821), which claims the benefit under 35 U.S.C. §119(e) of U.S. Provisional Patent Application No. 61/267,064 filed Dec. 6, 2009 and which claims the benefit under 35 U.S.C. §119(e) of U.S. Provisional Patent Application No. 61/227,404 filed Jul. 21, 2009, each of the above-identified applications being fully incorporated herein by reference.

BACKGROUND OF THE INVENTION

Field of the Invention

The invention generally relates to a method and system for modifying a user's driving behaviors, in particular to a system and method for modifying a user's unsafe driving behaviors, e.g., using one or more services of a controllable mobile device while driving, by providing a score to the user rating indicating that they are using a mobile device in a distracting way, or driving in a manner that indicates that they are distracted.

Discussion of the Related Art

Mobile cellular phones have become the preferred communication device for most people around the world. They offer convenience, ease of use, communication flexibility, and extensive coverage almost anywhere a person places or receives a call. Manufacturers of mobile phones (also referred to as mobiles or cell phones) have diversified their products to add color, style, and the ability to accessorize such phones as a fashion statement. The power of communicating from anywhere, along with these personalizations, has made cell phones as indispensable as the automobile for most Americans.

In fact, the dependence on cell phones has changed the way most people communicate. Almost 20% of U.S. households have dropped their wired landline service and rely exclusively on their cell phone. People engage in cell phone conversations from restaurants, at the mall, at the airport, and while traveling between locations. It is this later situation of use while traveling that has received a great deal of attention over the past few years—more particularly, driving while talking on a cell phone. Sadly, many people are killed every year as a result of someone driving while talking on a cell phone (or trying to dial a number on a cell phone), becoming distracted, and causing an accident.

Some studies have found that just listening on a cell phone while driving is significantly distracting to the human brain, and can cause the driver to make driving errors similar to those that can occur while under the influence of alcohol. In fact, in one study at Carnegie-Mellon University, the part of the brain associated with driving had a 37% decrease in brain function while a person was listening to a conversation and trying to understand the topics discussed and formulate response questions. This serious drop in cognitive awareness occurred regardless of whether the test subjects were using hand-held or hands-free mobile devices.

To reduce automobile accidents, over 50 countries around the world have enacted laws which limit or ban cell phone use while driving. In the United States, 21 states have banned cell phone voice use by novice (typically teen) drivers and 5 have banned use for all drivers unless a hands-free device is used. Laws are also on the books in 17 states to ban all cell phone use by school bus drivers.

As risky and dangerous as cell phone voice use is, the exploding popularity of text messaging (also known as texting) in the past few years, has made texting while driving (TWD) an even greater risk. A recent poll found that over 46% of teenage drivers admitted to texting while driving, with the actual rate probably higher than that. Because texting obviously involves the visual attention of the user's eyes to read a message and type in a message, the degree of distraction is far greater. Local and national news outlets have sadly reported a steady stream of fatal accidents where the cause was texting while driving. As a result, many state legislatures have banned or are discussing bans of TWD. Fourteen states in the U.S. will have TWD bans for all drivers at all times in effect by the end of 2009, with 10 states banning texting for novice (typically teen) drivers. Most states make these primary offenses.

While legislation is a good and necessary step to influence safe driving behavior and reduce accidents, it is not sufficient to prevent, or really restrict, the incidents of distracted and dangerous driving while using a mobile device. Too many people continue to drive dangerously despite existing laws and the known dangers. What is needed is a technical solution to reliably restrict mobile device services in situations that could cause danger to the user or other people. Further, the solution needs to make it difficult to circumvent or break the solution itself. With the type of mobile devices expanding (cell phones, smart phones, Personal Digital Assistants {PDAs}, wireless computers, mobile digital TVs, etc.), and new wireless technologies emerging (cellular, WLAN, WiMAX, Whitespace, mobile DTV, etc.), and the types of mobile services diversifying (voice, text, video, Internet, games, etc.) the need for a technical solution is even greater.

In an attempt to solve the risks of TWD, a variety of technologies have emerged, or been proposed. One such technology, provided by a company Textecution, www.textecution.com, provides an application for Android phones wherein the technology disables the entire texting function when it determines the mobile phone is moving at more than 10 miles per hour (mph), which is based on the GPS (Global Positioning System) capability built-in to the phone. Another technology, identified by the name Key2SafeDriving, http://safedrivingsystems.com, uses a specially design key with a casing (also known as a fob) that surrounds the key. When the key is flipped or slid open the fob sends a Bluetooth wireless signal to the phone to disable the entire mobile phone. Similarly, a solution by ObdEdge, http://www.cellcontrol.com, uses a module attached to a vehicle to send a Bluetooth signal directly to a mobile phone indicating that the car is moving, and in turn, software on the phone disables the phone.

A primary disadvantage of the above-identified technologies is that each relies on software within the mobile phone to disable the entire phone or a specific service on the phone. The software in these technologies has to be implemented for each specific mobile phone model, and therefore isn't easily available on all phones. In addition, recent malware attacks on mobile devices by hackers and organized criminals have proven that software on mobile devices can be easily compromised. Such technologies that rely on software, within the phone itself, to disable the phone, are vulnerable to misuse. Further, some of these technologies rely on wireless Bluetooth signals from a module in the vehicle to the mobile phone, which creates another point of vulnerability. For example, a user could block the Bluetooth signal from reaching the phone, and in turn, the phone would never receive the instruction to turn itself off.

Another disadvantage of these technologies is that they tend to take an overly broad approach to solving the problems of talking while driving, and/or texting while driving. These technologies are designed to detect motion of the mobile (typically a speed above 5-10 miles per hour), and then typically disable the entire mobile phone. They do not distinguish whether the user of the mobile is in the driver's seat of a vehicle, or in the passenger seat, or the back seat, or a seat on a bus or train. As a result they typically incorporate an over-ride to allow the user to bypass the blocking feature when they are a passenger. It is obvious that this creates a significant limitation to blocking in that the user can disable the block when they desire to text and drive. That is, such technologies do not have a position detection mechanism, to operate in conjunction with a controller for activating/deactivating service (e.g., texting) provided by a mobile, for determining where a mobile is located within a moving vehicle and then determining whether a service provided by the mobile should be disabled or enabled.

Consequently, a need exists for a method and system which detects operation of a vehicle, and controls specific services on one or more mobile phones (more generally, "mobile communication devices" or "wireless communication devices"), wherein the use of such services, while driving, can sufficiently distract a driver due to, e.g., the driver viewing and/or composing one or more non-driving related communications via the mobile communication device so that there is a significant decrease in driving safety. In particular, a need exists for a reliable network-based solution that monitors vehicle and mobile device status, and provides information regarding such statuses, along with subscriber service settings, to a network-based service provider to thereby control the services provided by the mobile communication device. Such a network-based method and system can provide advantages over other arrangements which exclusively rely on software in the mobile communication device (which could be compromised) and/or on a wireless Bluetooth connection directly to the device.

Furthermore, a need exists for a method and system which: (i) detects the physical position of one or more mobile communication devices within the vehicle, (ii) determines whether one or more of those devices are within a restricted zone (e.g., the driver's seat) of the vehicle, (iii) relays information regarding such a device within such a restricted zone to a network-based database and server where alerts or reports can be generated to the subscriber, and/or the restricted zone information may be relayed to the service provider of the mobile device and in turn the service provider may enable or disable one or more services on the mobile device.

SUMMARY OF THE INVENTION

Accordingly, the invention is directed to a method and system for controlling a mobile communication device in a vehicle that substantially obviates one or more of the problems due to limitations and disadvantages of the related art.

Disclosed herein is a method and system for detecting, monitoring and/or controlling one or more of mobile services for a mobile communication device (also referred to herein as a Controllable Mobile Device or CMD), and in particular, when the device is being used and the vehicle, operated by the user of the device, is moving. The present method and system (also referred to as a "mobile services control system" herein) determines whether the vehicle is being operated by a user that may also have access to a mobile communication device which, if used concurrently while the vehicle is in operation, may lead to unsafe operation of the vehicle. If the mobile services control system determines that a vehicle operator has potentially unsafe access to a mobile communication device, the mobile services control system may restrict operator access to one or more services that would otherwise be available to the operator via the mobile communication device.

In at least some embodiments of the mobile services control system, the position of a mobile communication device within the vehicle is determined, and in particular, whether the mobile communication device (also referred to as merely a "mobile device" herein) is within a restricted zone of the vehicle, which may include, but is not limited to, the driver's seat, areas near the driver's seat, other locations within the vehicle, or in some cases, the entire vehicle occupant enclosure. The present mobile services control system may be utilized to restrict mobile communication device access over any of a plurality of wireless communication standards, protocols or wireless interfaces (including CDMA, WCDMA, TDMA, UMTS, GSM, GPRS, OFDMA, WiMAX, FLO TV, Mobile DTV, WLAN, and Bluetooth technologies), and may be provided across multiple wireless network service providers. The present mobile services control system may be used to restrict access to mobile communication device services (e.g., texting, voice calls, games, videos, Internet access, online books, etc.) on a plurality of mobile communication devices available within a single vehicle occupant enclosure. The ability of embodiments of the mobile services control system to control access to services on one or more mobiles (e.g., within a vehicle occupant enclosure) may be substantially facilitated by centralizing or concentrating information related to subscribers to the mobile services control system, wherein "subscribers" as used herein, unless explicitly indicated otherwise, refers to persons or entities that contract for the user services provided by the mobile services control system (e.g., for restricting user access to certain mobile services). The information that may be centralized or concentrated by the mobile services control system include, e.g., subscriber related data for identifying: mobile(s) and/or mobile user(s) and/or vehicle(s) to which access to certain services on mobiles are to be restricted. In particular, in at least one embodiment, such centralization or concentration of subscriber information may be provided and maintained independently of most wireless service providers. For example, such centralization or concentration of subscriber information may be maintained and accessed via an Internet website, wherein such subscriber information may be accessed from a data management system which, in addition to identifying the subscribers, contains operational information about the mobile communication devices to be controlled by the mobile services control system, and the subscriber vehicles and also configurable service control parameters for allowing, e.g., subscribers to configure the mobile services control system to meet their individual needs and/or circumstances. In particular, the mobile services control system provides a mechanism for transmitting data detected during operation of vehicles to the centralized data management system for determining any restrictions on mobile services to be activated or deactivated. The present mobile services control system may also provide support for the correlation of data from the one or more detectors and/or sensors within the vehicle and the mobile communication device, with usage data from the service provider of the mobile communication device. The correlated data may be used for, but is not limited to, reporting on the use of mobile services while the vehicle is moving, sending notification messages and/or alerts, and/or real-time control (enable/disable) of mobile services on the mobile communication device. Accordingly, embodiments of the mobile services control system described herein provide one or more of the following features:

(a) The mobile services control system monitors and/or controls mobile communication device access to services while a corresponding registered vehicle is in operation.

(b) The mobile services control system provides an in-vehicle Vehicle Detection System (VDS) which includes a vehicle motion sensor to determine the operational state of the vehicle, and may include a detection engine (e.g., a hardware/software configuration of computational equipment) with one or more detectors and/or sensors to determine the presence and identity of one or more Controllable Mobile Devices (CMDs) within the vehicle and possibly to determine the position of one or more CMDs within the vehicle.

(c) The mobile services control system may provide a centralized data storage system (herein also referred to as a Safe Driving Database which contains, but is not limited to, (i) subscriber identity information, (ii) registration information identifying the Vehicle Detection System (VDS) for each subscriber's vehicle whose operation triggers activation of the mobile services control system for controlling a Controllable Mobile Device (CMD) within the vehicle, (iii) registration information identifying the one or more CMDs, (iv) customizable service control settings, and (v) "vehicle plus mobile detected information" which includes, but is not limited to, vehicle operational status information (e.g., moving/not moving, possibly GPS position, etc.), the identity of each of one or more CMDs detected within the vehicle, possibly position information for each of the one or more CMDs (e.g., in/out of the restricted zone, position relative to the restricted zone, etc.), possibly the boundary definition of the restricted zone within the vehicle, and other related vehicle or mobile state/position information.

(d) The mobile services control system may provide a centralized data management system (herein also referred to as a Safe Driving Registration System or SDRS) with user interfaces for customers, administrators, and communication (wireless) service providers to configure data monitoring and service control settings, along with generating usage reports and alert messages, and for the SDRS to provide electronic interfaces via which such service providers or other entities may gain access to data contained in the Safe Driving Database.

(e) The mobile services control system may provide for the transmission of vehicle operational status and mobile communication device position information to the Safe Driving Database, either in real-time or with a store-forward mechanism.

(f) The mobile services control system may provide, for each vehicle occupant enclosure being monitored, an in-vehicle VDS which can determine the position of each Controllable Mobile Device (CMD) within the vehicle occupant enclosure relative to a predetermined restricted zone, wherein the restricted zone may be any sub-area within the vehicle occupant enclosure, or the entire vehicle occupant enclosure, and then wirelessly transmit that restricted zone position information to the Safe Driving Database.

(g) The mobile services control system may provide and maintain data for each monitored Controllable Mobile Device (CMD), wherein the data may include one or more of: (i) a Mobile Device Air Identifier to identify the CMD to the Vehicle Detection System (VDS), (ii) a wireless signal identifier generated by the CMDs wireless signal, (iii) identification of one or more mobile services or applications that may be controlled by the mobile services control system. The mobile services control system may also provide: (i) a vehicle wireless network interface which may connect the CMD wirelessly to the VDS ii) a service provider wireless network interface which may connect it to a communication (wireless) service provider for communicating with the vehicle, and (iii) control software which may control the services or applications.

(h) The mobile services control system may provide a Service Decision System in operation with the Safe Driving Registration System (SDRS) to receive the vehicle plus mobile detected information and to receive input service control parameters, where the Service Decision System may further be operational to send realtime service control directives to the wireless service provider for the mobile device or to the SDRS to enable or disable specific services for a specific CMD, or to enable to disable the CMD itself, wherein the Service Decision System or SDRS may provide an option for the subscriber of the mobile services control system or the user of the CMD to temporarily override the control of enabling or disabling services.

In at least some embodiments, the system described herein may be used for purposes beyond that of controlling mobile electronic devices. For example, the system described can be easily integrated into various other commercial systems that involve a connection between a vehicle and the internet or a cloud, such as systems that provide a connection between a vehicle and a cloud to capture driving behaviors that are relevant to the insurance industry (such as Usage Based Insurance), or connections between commercial vehicles and the internet cloud where vehicle and driver information is captured for safety and other business purposes. With subject invention can be integrated into these systems, so as to provide control of potentially distracting devices in the vehicles, or elements of the invention can be integrated into hese systems to be able to identify individuals within the vehicle, or identify the drivers of the vehicles, either by identifying that a CMD is within the vehicle through the techniques described herein, or by identifying the driver of the vehicle throu the techniques described herein. This information can then be used for various other commercial purposes other than controlling potentially distracting electronic devices, such as improving insurance company performance by knowing the identity of drivers, or by associationg particular safe or unsafe driving practices with specific drivers, or for commercial customers, identifying the drivers of a vehicle and or identifying safe or unsafe driving practices of a specific driver.

In at least some embodiments, registered or associated CMDs are utilized that are associated to a specific VDS and therefore represent the CMDs that are most likely to be used by a driver of the vehicle associated with the VDS. The use of registered CMDs (which is typically number between 1 and 5, but in some instances can be greater) limits the number of CMDs that are required to be determined to be in or out of a vehicle, and therefore significantly enhancing the functionality of the system for controlling mobile devices in vehicles. However, it is noted that various aspects of the invention can be utilized with non-registered or non-associated CMDs, or alternately a much larger populations of CMDs might be associated or registered with a CMD (such as the CMDs subscribing to a particular MSDP, or the CMDs in a particular geographic area may be registered to a specific CMD) to also enhance the system.

In one embodiment, the system can incorporate a reward for self-identifying the driver at the beginning of the trip through a handset, or through scheduling thereby eliminating ambiguity if the individual is driving, providing a more accurate score, creating the habit of self-identifying at the beginning of the trip, and providing additional accurate information for use by insurance companies and other parties that are interested in knowing the identify of an individual who is driving. In addition, the self-identifying feature of the application, can incorporate other information to the driver, such as driving information, route information, traffic information, motivational thought for the day, joke of the day, or similar type things that incentivize the driver to stop and identify themselves prior to starting the trip.

In an embodiment, an aspect of the invention seeks to control unsafe driving by changing the behavior of drivers to lessen the occurrence of unsafe driving events such as texting while driving, use of distracting features of a mobile device while driving, speeding, swerving, hard corners, e.g., greater than a predetermined threshold of acceleration, hard braking and acceleration, e.g., greater than a predetermined threshold of acceleration, lack of focus on driving, and lack of anticipation while driving. An embodiment provides immediate feedback or substantially immediate feedback on safe driving habits (as indicated by lack of unsafe behaviors) formatted as a game or score, thereby motivating the driver to change driving behaviors through a desire to win the game, meet personal goals, meet team goals, and through tangible and intangible rewards provided by doing well in the game, or by consequences for unsafe driving, provided by parents, law enforcement, insurance companies, schools, or other organizations or individuals that can provide material consequences or rewards to the driver.

It is understood that this Summary section is neither intended to be, nor should be, construed as being representative of the full extent and scope of the present disclosure. Additional benefits, features and embodiments of the present disclosure are set forth in the attached figures and in the description herein below, and as described by the claims. Accordingly, it should be understood that this Summary section may not contain all of the aspects and embodiments claimed herein.

Additionally, the disclosure herein is not meant to be limiting or restrictive in any manner. Moreover, the present disclosure is intended to provide an understanding to those of ordinary skill in the art of one or more representative embodiments supporting the claims. Thus, it is important that the claims be regarded as having a scope including constructions of various features of the present disclosure insofar as they do not depart from the scope of the methods and apparatuses consistent with the present disclosure (including the originally filed claims). Moreover, the present disclosure is intended to encompass and include obvious improvements and modifications of the present disclosure.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE ILLUSTRATED EMBODIMENTS

Figure 1:
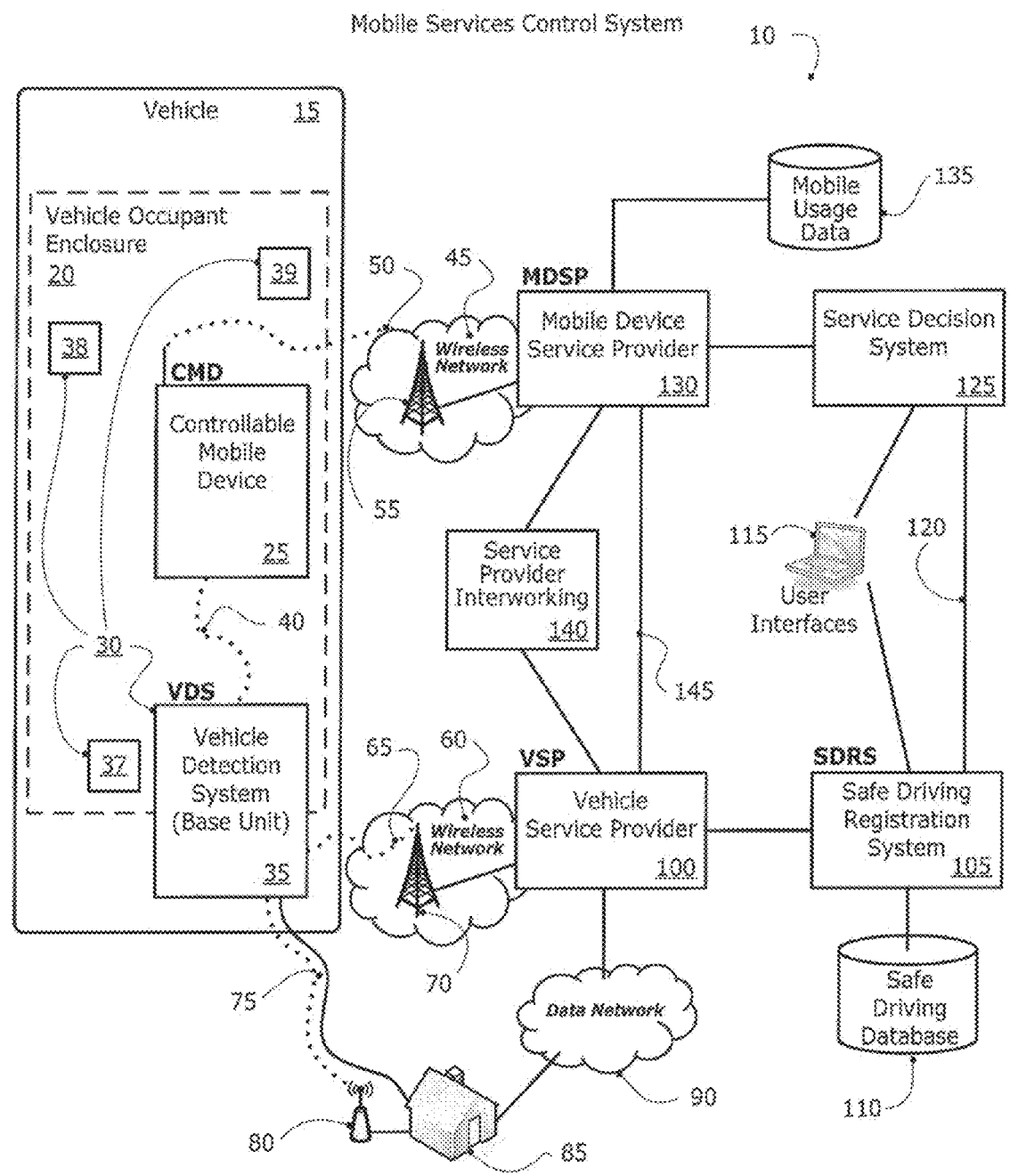
FIG. 1 discloses a system diagram of an illustrative embodiment for a system for controlling mobile devices in a moving vehicle's restricted zone.

For the purposes of promoting an understanding of the principles of the present disclosure, reference will now be made to the exemplary embodiments illustrated in the drawing(s), and specific language will be used to describe the same.

Appearances of the phrases an "embodiment," an "example," or similar language in this specification may, but do not necessarily, refer to the same embodiment, to different embodiments, or to one or more of the figures. The features, functions, and the like described herein are considered to be able to be combined in whole or in part one with another as the claims and/or art may direct, either directly or indirectly, implicitly or explicitly.

Functional units described in this specification may be labeled as modules, in order to more particularly emphasize their structural features. A module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like. Modules may also be implemented in software for execution by various types of processors. An identified module of programmable or executable code may, for instance, comprise one or more physical or logical blocks of computer instructions which may, for instance, be organized as an object, procedure, or function. Components of a module need not necessarily be physically located together, but may, e.g., comprise disparate instructions stored in different locations which, when joined logically together, comprise the module and achieve the stated purpose for the module.

A module and/or a program of executable code may be a single instruction, or many instructions, and may even be distributed over several different code segments, among different programs, and across several memory devices. Similarly, data or input for the execution of such modules may be identified and illustrated herein as being an encoding of the modules, or being within modules, and may be embodied in any suitable form and organized within any suitable type of data structure.

The various system components and/or modules discussed herein may include one or more of the following: a host server or other computing systems including a processor for processing digital data; a memory coupled to the processor for storing digital data; an input digitizer coupled to the processor for inputting digital data; an application program stored in one or more machine data memories and accessible by the processor for directing processing of digital data by the processor; a display device coupled to the processor and memory for displaying information derived from digital data processed by the processor; and a plurality of databases or data management systems.

The present disclosure may be described herein in terms of functional block components, screen shots, user interaction descriptions, optional selections, various processing steps, and the like. It should be appreciated that such descriptions may be realized by any number of hardware and/or software components configured to perform the functions described. Accordingly, to implement such descriptions, various integrated circuit components, e.g., memory elements, processing elements, logic elements, look-up tables, and the like may be used, which may carry out a variety of functions under the control of one or more microprocessors or other control devices. Similarly, the software elements of the present disclosure may be implemented with any programming or scripting language such as C, C++, Java, COBOL, assembler, PERL, Visual Basic, SQL Stored Procedures, AJAX, extensible markup language (XML), Flex, Flash, with the various algorithms being implemented with any combination of data structures, objects, processes, routines or other programming elements. Further, it should be noted that embodiments in the present disclosure may employ any number of conventional techniques for data transmission, signaling, data processing, network control, and the like as one skilled in the art will understand. Embodiments of the present disclosure may also include detection or prevention of security issues using various techniques. Additionally, many of the functional units and/or modules herein may be described as being "in communication" with other functional units and/or modules. Being "in communication" refers to any manner and/or way in which functional units and/or modules, such as, but not limited to, computers, laptop computers, PDAs, modules, and other types of hardware and/or software, may be in communication with each other. Some non-limiting examples include communicating, sending, and/or receiving data and metadata via: a network, a wireless network, software, instructions, circuitry, phone lines, Internet lines, satellite signals, electric signals, electrical and magnetic fields and/or pulses, and/or so forth.

Communication among the parties in accordance with the present disclosure may be accomplished through any suitable communication channels, such as, for example, a telephone network, an extranet, an intranet, Internet, point of interaction device (point of sale device, personal digital assistant, cellular phone, kiosk, etc.), online communications, off-line communications, wireless communications, transponder communications, local area network (LAN), wide area network (WAN), networked or linked devices and/or the like. Moreover, although the invention may be implemented with TCP/IP communications protocols, embodiments of the disclosure may also be implemented using IPX, Appletalk, IP-6, NetBIOS, OSI or any number of existing or future protocols. Specific information related to the protocols, standards, and application software utilized in connection with the Internet is generally known to those skilled in the art and, as such, need not be detailed herein. See, for example, DILIP NAIK, INTERNET STANDARDS AND PROTOCOLS (1998); JAVA 2 COMPLETE, various authors, (Sybex 1999); DEBORAH RAY AND ERIC RAY, MASTERING HTML 4.0 (1997); and LOSHIN, TCP/IP CLEARLY EXPLAINED (1997), the contents of which are hereby incorporated by reference.

As used herein, "comprising," "including," "containing," "is," "are," "characterized by," and grammatical equivalents thereof are inclusive or open-ended terms that do not exclude additional unrecited elements or method steps unless explicitly stated otherwise.

In order to more fully appreciate the present disclosure and to provide additional related features, the following references are incorporated therein by reference in their entirety:

(1) U.S. Pat. No. 6,122,486 by Tanaka et al. which discloses, a transmission restricting system which has a transmission interruption controlling means for generating and radiating a magnetic field pattern including a command code to command the transmission interruption to a radio communication terminal equipment in a radio-wave transmission-prohibited area, the transmission interruption controlling means being disposed at the entrance or exit of the radio-wave transmission-prohibited area; a transmission interruption releasing means for generating and radiating a magnetic field pattern including a command code to command the releasing of transmission interruption to the radio communication terminal equipment in the radio-wave transmission-prohibited area, the transmission interruption releasing means being disposed at the entrance or exit of the radio-wave transmission-prohibited area; and a radio communication terminal equipment comprising means for detecting a magnetic field pattern including a command code to command the transmission interruption or the releasing of transmission interruption, and means for controlling the process of the transmission interruption or the releasing of transmission interruption according to the result of the detection of the detecting means.

(2) U.S. Pat. No. 6,353,778 by Brown which discloses, an automobile computer control system for limiting the usage of wireless telephones in moving automobiles comprising an implementation for sensing when the velocity of the automobile exceeds a predetermined velocity, a wireless implementation for sensing when the wireless telephone is in use by the driver of the automobile and a function responsive to both of the sensing implementations for limiting the use of the wireless telephone by the driver of the automobile when the velocity of the automobile exceeds the predetermined velocity. For the best safety, the predetermined velocity is any moving velocity. Also, the wireless device for sensing when the velocity of the automobile exceeds a predetermined velocity may be carried out by an infrared device.

(3) U.S. Pat. No. 6,556,810 by Suzuki which discloses, a communication inhibiting apparatus with: disturbing wave generating means for generating a disturbing wave signal which disturbs communications to and from a portable telephone or similar communication terminal equipment; and disturbing wave emitting means for emitting the signal generated by the disturbing wave generating means, as the disturbing wave, to the communication terminal equipment.

(4) U.S. Pat. No. 6,690,940 by Brown et al. which discloses, a system for selectively disabling use of at least selected features of a stand-alone electronic device under a predetermined set of conditions. The system establishes a state of the set of conditions as being satisfied or unsatisfied, communicates the state to the electronic device, and disables the selected features if the state is satisfied. In one embodiment, the system may be advantageously be used to prevent vehicular accidents by at least partially disabling non-emergency use of a wireless telephone in a moving vehicle. In another embodiment, the system may be used to disable features of an electronic device within a predetermined area having a boundary that is independent of a communications network cell.

(5) U.S. Pat. No. 6,973,333 by O'Neil which discloses restrictions on use of a cellular telephone in a vehicle, such as an automobile, that are imposed using a global position system (GPS) device to determine the location of a vehicle in relation to geographic regions in which legal or customer restrictions on cellular telephone use are to be imposed. Network or local short-range wireless transmitters supply information to a cellular telephone describing potentially applicable restriction information retrieved from network databases. In response, a cellular telephone determines applicability of such restrictions and applies them to further use of the cellular telephone while such restrictions continue to apply. Alternative arrangements allow vehicle-based or network based processing of region and restrictions information to yield command messages to cellular telephones.

(6) U.S. Pat. No. 7,064,656 by Belcher et al. which discloses a controller to prevent access or utilization by a vehicle operator to communications devices installed on the vehicle when the vehicle is in motion thereby reducing distractions of the operator.

(7) U.S. Pat. No. 7,107,058 by Inoguchi et al. which discloses a printer that enables a determination whether a failure has occurred in a device during initialization or a radio wave condition is bad. Receive electric field strength during a time period from a time at which a turn-off message is outputted to a time at which turn-on message is outputted and receive electric field strength after the turn-on message is outputted are measured. The measurements are compared with each other and information indicating the condition of each of a plurality of channels is printed out according to the results of the comparison. A user can reference the printed information to determine whether a failure has occurred in a device or the radio wave condition is bad.

(8) U.S. Pat. No. 7,181,229 by Singh et al which discloses a system for disabling a cell phone in the presence of certain conditions, and for switching it off in the presence of some other conditions, while allowing its use in the normal fashion in the absence of these two sets of conditions. Thus, this system regulates cell phone use in accordance with specified restrictions in specific locations, and allows its normal functioning when these restrictions are not required. Specifically, a first condition is an attempt to operate a cell phone by the driver of a vehicle having its ignition on and/or moving above a certain speed. In such a condition the system would automatically disable the OK switch of a cell phone and may also perform the CALL END function. In the second condition the system automatically switches off any cell phone in the ON condition being carried on the person of an individual occupying a seat in an aircraft, or a committee room, or any other such location where such a restriction is envisaged. The system also makes a provision for automatic sequential dialing of a specified set of numbers like the police, medical services etc. during an emergency by allowing overriding any regulatory restriction. In addition, U.S. Pat. No. 7,181,229 also relates to control circuits provided in the system for preventing tampering with or bypassing the system by cell phone users.

(9) U.S. Pat. No. 7,206,615 by Ochi et al. which discloses a first transmitter that outputs a request signal requesting a response to a mobile device toward an area including a driver's seat and its neighborhood, and a second transmitter outputs a request signal toward an area covering the entire vehicle. The mobile device transmits a response signal to a receiver if receiving the request signal transmitted from the first or second transmitter. The controller detects the position of the mobile device based on a communication result between the mobile device and the receiver in response to the request signals transmitted from the first and second transmitters.

(10) U.S. Pat. No. 7,260,390 by Skinner et al. which discloses a panel provided to a wireless device that turns off all RF capability of the wireless device (including, but not limited to notifications, wireless web clipping, instant messaging, email sending/receiving, phone calls, etc.). The panel is brought up on a screen of the wireless device by pressing a programmed hard button for more than 1 second. Once the RF capability has been turned off, if the user attempts to access a program or other device that requires the RF capabilities, a notification is displayed that identifies the RF capabilities as being disabled and prompts the user whether to continue. If the user continues, the RF device is automatically enabled, otherwise the RF device remains disabled.

(11) U.S. Pat. No. 7,343,148 by O'Neil which discloses, restrictions on use of a cellular telephone in a vehicle, such as an automobile, that are imposed using a global position system (GPS) device to determine the location of a vehicle in relation to geographic regions in which legal or customer restrictions on cellular telephone use are to be imposed. Network or local short-range wireless transmitters supply information to a cellular telephone describing potentially applicable restriction information retrieved from network databases. In response, a cellular telephone determines applicability of such restrictions and applies them to further use of the cellular telephone while such restrictions continue to apply. Alternative arrangements allow vehicle-based or network based processing of region and restrictions information to yield command messages to cellular telephones to control their further use.

(12) U.S. Pat. No. 7,369,845 by Keohane et al. which discloses, a portable communication device that detects a current speed of travel of the portable communication device independent of any vehicle temporarily transporting the portable communication device. A speed based setting controller of the portable communication device compares the current speed to at least one threshold value set at the portable communication device. Responsive to the current speed exceeding the threshold value, the speed based setting controller automatically assigns a separate speed based setting to a current setting for each feature assigned to the threshold value, wherein each current setting for each feature designates the operability of that feature within the portable communication device, such that the current setting for each feature adjusts with a speed of travel as detected by the portable communication device.

(13) U.S. Pat. No. 7,395,046 by Hossain et al., which discloses a method and apparatus for enhancing the probability of a successful emergency call completion and emergency callback on a mobile station in a network, the method comprising the steps of: during an emergency call attempt, monitoring whether the mobile station has received a non-voice service request from the network and, if yes, ignoring the non-voice service request, Further, during a callback period, monitoring whether the mobile station has received a service request from the network and, if yes, ignoring the service request if the service request is a non-voice service request that is anything but a position location service request. Further, during a callback period, monitoring whether a user attempts to initiate a non-voice service request that is anything but a position location service request, and if yes ignoring the non-voice service request.

(14) U.S. Pat. No. 7,400,891 by Aaron which discloses wireless terminals that are remotely controlled by identifying a wireless terminal that is located at a premises and obtaining at least one operational authorization rule for the wireless terminal that was identified, and that applies to the premises at which the wireless terminal is located. Selected operations of the wireless terminal are disabled and/or enabled in response to the at least one operational authorization rule that was obtained for the wireless terminal that was identified and that applies to the premises at which the wireless terminal is located.

(15) U.S. Pat. No. 7,471,929 by Fujioka et al. which discloses a device and a method for telephone countermeasure in using a telephone during driving which can automatically suppress communication of only a driver in a vehicle. [Means For Solving Problems] The device for telephone countermeasure includes a database (3), a driver judgment unit, and a mode switching unit. The database (3) contains driver face data (3-1) and a telephone number (3-2) of a mobile telephone (7) used by the driver for each of the drivers. The driver judgment unit identifies the current driver of the vehicle in the database (3) by the face authentication. The mode switching unit extracts the telephone number (3-2) of the mobile telephone (7) used by the identified driver from the database (3) and switches the mobile telephone (7) of the driver to a drive mode such as a message recording mode by using the telephone number.

(16) U.S. Pat. No. 7,734,315 by Rathus et al. which discloses a method and system that limits the use of a communication device present in an area controlled by an intelligent controller. The intelligent controller detects any present communication devices in the area and conducts an inventory providing information about each detected device. The intelligent controller compares that information to a standard of use data, which specifies the conditions need to be present for allowing the usage of a communication device. If such conditions are not met, the intelligent controller sends commands to the communication device to restrict its functionality. Else if, the intelligent controller is incapable of restricting the communication device, it can notify authorities of unauthorized usage of a communication device in the restricted area.

(17) U.S. Pat. No. 7,640,101 by Pair et al. which discloses a system that uses a gps receiver and a computer program product to disable a feature of an electronic device when movement of the receiver is detected. Speed data from a gps data stream is monitored. When the speed of the gps receiver exceeds a predetermined value, the desired feature of the electronic device is disabled. For example, when the speed of the gps receiver exceeds 0.5 knots, a windows function call is executed to set a desired display element as a top window on a display screen. The system may allow for temporary enabling of disabled features and for rapid enabling of disabled features when motion stops. The system may also include navigational software. A manufacturer may also use a proprietary combination of one or more disabled data fields in a gps data stream to identify gps receivers approved for use with the system.

(18) U.S. Pat. No. 7,474,264 by Bolduc et al. which discloses a system and method for detecting use of RF transmit devices (e.g., cellular phones) in a vehicle. The system includes a first RF antenna for detecting signal strength of an RF signals transmit device at a first location in a vehicle and a power first detector for generating a first output signal indicative thereof. The system also includes a second antenna for detecting signal strength of the RF signals at a second location in the vehicle and a second power detector for generating a second output signal indicative thereof. The system further includes a signal processor for processing the first and second output signals to determine the presence of an RF transmit device in use in the vehicle and to further determine the location of the RF transmit device to determine if a driver is using the device.

(19) U.S. Pat. No. 7,477,135 by Belcher et al. which discloses an access (utilization) controller to restrict or block visual or aural interaction between a vehicle operator/driver and mobile communications and information devices such as computers, mobile telephones, pagers, personal digital assistants (PDAs), and the like mounted on or used in the vehicle is disclosed. The utilization controller comprises sensors to detect motion or "potential" motion of the vehicle, a processor receiving data from the sensors and inhibitor means responsive to the processor to "blank out" or otherwise inhibit any distracting visual or aural output from the communications or information devices while the vehicle is in motion or about to move. The sensor data such as speedometer, transmission gear position indicator, antilock brakes and others are extracted from a vehicle's internal monitoring and control systems.

(20) U.S. Pat. No. 7,619,507 by Santos et al. which discloses aspects that provide a system and method for receiving information in a vehicle. Information pertaining to the vehicle's driver may be stored. Information pertaining to the vehicle's driver may be made audile through the vehicle's radio system.

(21) U.S. Patent No. 2002/0198005 by Hilton et al. which discloses, a logic based control system to modify and improve operations of wireless communications devices and the operating systems of a plurality of portable wireless communications devices by continuously, selectively and automatically controlling, enabling and/or disabling access to the transmission and reception of portable wireless communication devices depending on the factors of velocity, location and/or time of the wireless communication device, while continually enabling access to emergency communications at any time, location and/or velocity.

(22) U.S. Patent No. 2005/0170850 by Edwards et al. which discloses, the methods and apparatuses for selectively disabling functionality of a device detect a device; detecting a device type of the device; and transmitting a signal to the device for selectively disabling a function of the device based on the device type.

(23) U.S. Patent No. 2005/0184860 by Taruki, which discloses a portable information terminal controlling system comprising the detector-transmitter and the cellular phone. The detector-transmitter includes the automobile moving state detecting unit and the control information transmitting unit. The cellular phone includes the function controlling unit, the transmitter-receiver, the display and the control unit. When the detector-transmitter detects that an automobile is moving, the detector-transmitter sends control information to a function controlling unit. When the detector-transmitter detects that an automobile is moving, the function controlling unit limits a part of a display function and a communication function of a portable information terminal, or limits all functions of the portable information terminal, and makes the portable information terminal be in a difficult state to use by giving an instruction to the control unit. Judgment of the driver's use of the portable information terminal is performed based on a signal arriving time and signal strength between the detector-transmitter and the function controlling unit, or an image extract with a camera included in the detector-transmitter.

(24) U.S. Patent No. 2005/0255874 by Stewart-Baxter et al. which discloses a system and method for detecting motion of a cell phone and disabling the use of the cell phone while moving or driving. The inventive system includes: a cell phone; a sensor to detect motion of the cell phone; software in the cell phone to disable the use of the cell phone when motion is detected. In a preferred embodiment, the system also recognizes the near proximity of an automobile and disables the use of the cell phone in this near proximity.

(25) U.S. Patent No. 2006/0099940 by Pfleging et al. which discloses a method for changing the status of a mobile apparatus based upon the velocity of the mobile apparatus. The communication system determines the velocity of a mobile apparatus by calculating the difference between a first position of a mobile apparatus at a first time and a second position of the mobile apparatus at a second time. If the velocity of the mobile apparatus exceeds a predetermined threshold, the communication system changes the status of the mobile apparatus to a sleep state and ends a call that the mobile apparatus is involved in.

(26) U.S. Patent No. 2007/0072616 by Irani which discloses, a method for preventing cellular phone usage while driving. In one embodiment a GPS system incorporated into the workings of the cellular phone is used to detect that the phone is in motion, and that the rate of movement exceeds some preset value indicating that the phone is in a moving vehicle. Having detected motion the phone will deliver a number of options ranging from complete shutdown until motion stops, to use only for emergency purposes, to only limited use, or to complete use by interjecting a preset PIN or other such password which will allow the cellular phone user to override the phone shutdown mechanism. Other alternate means for detecting motion include triangulation between numerous towers, to signal strength variation from a single tower, to signals generated by miniature accelerometers and velocity meters imbedded in the phone specifically for detecting rate of movement.

(27) U.S. Patent No. 2008/0139183 by Keohane et al. which discloses, a portable communication device that detects a current speed of travel of the portable communication device independent of any vehicle temporarily transporting the portable communication device. A speed based setting controller of the portable communication device compares the current speed to at least one threshold value set at the portable communication device. Responsive to the current speed exceeding the threshold value, the speed based setting controller automatically assigns a separate speed based setting to a current setting for each feature assigned to the threshold value, wherein each current setting for each feature designates the operability of that feature within the portable communication device, such that the current setting for each feature adjusts with a speed of travel as detected by the portable communication device.

(28) U.S. Patent No. 2008/0214211 by Lipovski which discloses, a system for selectively restricting or enabling the use of a cellular telephone module in a zone is described, comprising: a control signal transmitter for generating a control signal at an entrance to the zone or alternatively generating control signals throughout the zone; the cellular telephone including a module; a receiver module within the cellular telephone responsive to the control signal for generating a module enable/restrict upon receipt of the control signal; and a switch within the cellular telephone responsive to the module enable/restrict for selectively enabling or inhibiting the operation of the module for a predetermined period of time after receipt of the control signal. Additionally, this system's cellular telephone can dial a telephone, send a message to it, receive a text message from it, and send digits to it, to handle emergencies or conduct business. Finally, the system can remind owners to recharge their cellular telephone batteries.

(29) U.S. Patent No. 2009/0004968 by Miyake which discloses an in-vehicle apparatus that determines in the vicinity the presence of a portable terminal designated with a device requiring restriction on radio transmission as a device name thereof. Radio transmission from a cellular phone is thereby restricted. In contrast, when determining in the vicinity the absence of the portable terminal designated with a device requiring restriction on radio transmission, the restriction on radio transmission from the cellular phone is removed. In the event of a person with a cardiac pacemaker getting on the vehicle, if the person carries a portable terminal designated with a device requiring restriction on radio transmission as a device name, the concern of the person about a possibility that the cellular phone has a bad influence on the cardiac pacemaker can be prevented.

(30) U.S. Patent No. 2009/0029675 by Steinmetz, et al. which discloses, a safety device for automotive vehicles (cars, buses and trucks) or rail locomotives. The device inhibits use of cellular telephones and other communication devices that run the risk of distracting a driver/operator while the vehicle is in motion. Several techniques for inhibiting use are described which can be used individually or in a complementary combinations. In one technique, a rapidly varying signal level is created local to the communication device. The variations exceed the operational limits of the system, thereby inhibiting communications. In another technique, the safety device emits radiation that interferes with the reception of signals by the communication device only within the interior of the vehicle and will not interfere with cell phones or wireless devises outside the automotive vehicle or rail locomotive. As another alternative, masking signals also may be generated to prevent signals sent by the communication device within the vehicle from being intelligible at receiving stations outside the vehicle.

(31) U.S. Patent No. 2009/00895744 by Sellin et al. which discloses, a system for controlling access to a network includes a wireless switch configured for radio frequency communication with a mobile unit associated with a radio frequency identification tag. The wireless switch is adapted for determining if a radio frequency identification tag is located within a first area, and enabling the mobile unit to access the network according to a first scheme if the mobile unit is located within the first area.

(32) U.S. Patent No. 2009/0111422 by Bremer et al. which discloses, control systems and methods that are provided for controlling a personal communication device (PCD), such as a wireless telephone, personal data assistant (PDA), etc. The control systems and methods enable the controlled PCD (CPCD): (1) to determine (a) CPCD motion (speed, acceleration, or both) and/or (b) geographical location and (2) to (a) modify (enable, disable, and/or otherwise change) one or more CPCD functions based at least in part on the CPCD motion and/or geographical location and/or (b) communicate an alert (locally and/or to a remote communication device). The control of CPCD functions and alerts may also be dependent on other factors, such as the laws of the authoritative legal jurisdiction wherein the CPCD is located. The operation of the following CPCD functions can be modified, as nonlimiting examples: keypad, image display, microphone, speaker, camera, voice call out, voice call answer, text message creation, text message transmission, text message reception, email creation, email reception, image creation, image reception, Internet browsing, gaming, ring signal operation, communication signal transmission, and communication signal reception.

It is of great national importance to change the behavior of drivers so that distracted driving, such as using on or more services of a mobile device while driving is lessened, thereby promoting safe driving behavior. Legislation is failing to change behavior, and systems the only control texting are also not changing the behavior of the majority of the population also the current techniques are perceived as overly intrusive, and impinging on rights. Thereby, hastening the adoptions of the same.

Embodiments of the invention are directed towards a subject behavior modification method and system that provides a system that rewards the driver, both with intangible and tangible rewards the driver is both motivated to adopt the system and also then motivated to change their behavior. In one embodiment, intangible rewards may include a score or ongoing ranking on a social media site or communicated over some other network. Moreover, a tangible reward may include an economic incentive, e.g., a reduction in an insurance premium. By incorporating elements that reward other safe driving behaviors, such as staying within the speed limit, not swerving and not abruptly stopping, the system is also able to broaden the behavior modification to a larger suite of behaviors, so that the improvement goes beyond distracted driving, to actually creating safe drivers in multiple respects.

The system can incorporates both gamification and incentification, which have proven to be effective in changing behaviors in multiple domains, for instance skiing behaviors through the Epic Mix program, used by Vail Associates, to provide reward for skiers for the amount, and type of skiing they do.

An embodiment, combines elements such as distracted driving control systems, distracted driving reporting systems, measurement of vehicle characteristics indicating safe or unsafe behavior, indication of whether any of these systems have been overridden, and the ability to provide real time feedback and incentives (at the end of a trip). Thereby, the motivation to change behavior is powerful.

In an embodiment, reward for behavior changes or to motivate behavior change can include a number of different type of awards, e.g., intangible awards, tangible awards, combinations of the same and the like. Intangble awards or elements include, e.g., earning of badges, personal scores, team scores, competitors scores, leader boards, recognition on social media such as facebook twitter, public acknowledgement as a safe driver, other form of networked communication, combinations of the same and the like. In addition, competition can be used as a tangible award, for instance with individuals, corporations, family members, or other groups competing against one another to determine who has the safest driver population, such as cities competing against one another. In addition, the tangible rewards can be used in combination or in separate form intangible rewards. The tangible rewards can also include economic incentives, e.g., cash incentives provided for safe driving, insurance discounts, discounts on purchased (such as gasoline, food or other goods), discounts on other products of value to the driver such as discounts on beverages, or phone service provider service, or insurance, or food items, or hard goods such as clothing, that are provided by corporate partners to the program that recognize corporate reward for supporting social issues, brand halo effects, and from incentivizing individuals to go to their store and purchase an item for a discount.

The ability to provide feedback at the end of a trip as to the particular trip score and ultimate score, as well as the ability to identify the location at the end of the trip, allows instant gratification tie-ins to further drive behavior modification, such as at the end of the trip, when the score is provided, a map is presented showing nearby locations that will provide discounts, at that moment for safe drivers, for instance a coffee shop that is within a close distance, e.g., quarter mile, that will discount the price of a beverage, e.g., by 50%, if the arrive in the next period of time, including the ability for the discount to be increased if the score of the driver is increased.

These incentives can also be chosen by the driver to be things of value to them, for instance, they might choose from a list of possible incentives, to create a shorter list of the things that highly incentivize them, such as choosing a discount at high profile brand store such as Nike or Ambercrombie and Fitch, or choosing a gas discount. Thereby, further incentivizing the driver.

As a further incentive, the system can incorporate a multiplier feature, so that as the driver completes a certain number of safe drive sequences in a row, e.g., a greater award, the reward multiplies, creating an additional powerful incentive to continue to drive safely.

In a preferred embodiment, the system permits or enables both controlling a distracted driving and/or reporting on distracted driving. In an embodiment, the system is configured to monitor whether a mobile device is in use, or monitor if the system has been overridden or defeated, or if the system is not in use but the driver still used distracting features on the phone, and then penalizing the driver by limiting points gained, or taking points away, a powerful incentive is created to prevent distracted driving behavior. Further, by utilizing embodiments described herein the system can determine who is in the vehicle, as well as who is actually driving the vehicle, thereby the accuracy of the system is increased, reducing false positive and false negatives, so as to further incentivize the driver, as they are not being falsely penalized, or falsely rewarded.

In an embodiment, a record of a driver's performance, e.g., including a score, can provide the basis for additional tangible benefits, by providing a metric by with the individual can be rewarded directly by organizations, or by the parents, for instance the parents can provide a financial reward if a driver exceeds a certain number in a certain period, or a company can provide a reward in vacation, or pay, or other gifts if an employee exceeds a certain point score in a certain period. In addition, a third-party, e.g., an insurance company can provide a reward or a discount on insurance rates, if drivers exceed a certain score, or they can provide discounted rates to new insureds, if a driver exceeds a certain score, providing an additional incentive for insurance companies to adopt such a system.

In an embodiment, drivers programs can adopt such a system, schools can adopt the system, federal government, and/or states can legislate such a system as part of a Graduated License Program, so that it becomes mandatory for a new driver, with the rewards of the system supporting the adoption of the system.

In one embodiment, the system can incorporate a reward for self-identifying the driver at the beginning of the trip through a handset, or through scheduling thereby eliminating ambiguity if the individual is driving, providing a more accurate score, creating the habit of self-identifying at the beginning of the trip, and providing additional accurate information for use by insurance companies and other parties that are interested in knowing the identify of an individual who is driving. In addition, the self-identifying feature of the application, can incorporate other information to the driver, such as driving information, route information, traffic information, motivational thought for the day, joke of the day, or similar type things that incentivize the driver to stop and identify themselves prior to starting the trip.

In an embodiment, an aspect of the invention seeks to control unsafe driving by changing the behavior of drivers to lessen the occurrence of unsafe driving events such as texting while driving, use of distracting features of a mobile device while driving, speeding, swerving, hard corners, e.g., greater than a predetermined threshold of gravity force, hard breaking and accelerating, e.g., greater than a predetermined threshold of gravity force, lack of focus on driving, and lack of anticipation while driving. An embodiments provides immediate feedback or substantially immediate feedback on safe driving habits (as indicated by lack of unsafe behaviors) formatted as a game or score, thereby motivating the driver to change driving behaviors through a desire to win the game, meet personal goals, meet team goals, and through tangible and intangible rewards provided by doing well in the game, or by consequences for unsafe driving, provided by parents, law enforcement, insurance companies, schools, or other organizations or individuals that can provide material consequences or rewards to the driver.

In one embodiment, a mobile services control system for generating a score based on driving events. The system is configured to prevent unsafe driving, distracted driving, and/or change unsafe driving behavior of a user of the controllable mobile device. The system optionally includes an in-vehicle detection system and computational equipment. The computation equipment may reside in the cloud, partially within the cloud, and/or network. The in-vehicle detection system is configured to determine one or more characteristics of a vehicle indicative of the vehicle being operated by a user, e.g., key on, movement of vehicle, acceleration, combinations of the same and the like. The computational equipment is configured to generate the score based on a first input indicative of whether a controllable mobile device is within the vehicle when the vehicle is in operation, a second input comprising the one or more characteristics indicative of the vehicle being operated by a user, and a third input indicative of one or more of a use of the controllable mobile device, a use of the system that prevents unsafe use of the controllable mobile device, overriding the system that prevents unsafe use of the controllable mobile device, and unsafe driving events. Alternatively and/or optionally, the system can be configured to restrict one or more services of the controllable mobile device, report and monitor on the same.

In one embodiment, the use of the controllable mobile device includes any use, e.g., including but not limited to moving the phone, whether the phone is on or off, reviewing text message, typing a text message, sending a text message, reviewing an email message, typing a text message, sending an email, playing a game, viewing a video, and information provided via the Internet. In one embodiment, the score may include rewards, discounts and/or be indicative of a driving behavior of the user, e.g., may include one or more of a number of hard corners, a number of hard brakes, a number of overrides, a number of perfect segments, a number of perfect miles, over maximum velocity, over speed limit, miles driven, segments driven and other non-game data.

FIG. 1 is a diagram of an embodiment of the mobile services control system 10. The system 10 includes the Vehicle Detection System (VDS) 30 which detects the operational status of a vehicle 15 and may also detect the identity and presence of one or more Controllable Mobile Devices (CMD) 25 within the vehicle, and also may detect the position of the one or more CMDs 25 within the vehicle occupant enclosure 20 (e.g., the passenger seating compartment of the vehicle wherein the driver or operator also resides). The Controllable Mobile Device (CMD) 25 provides a person with access to one or more of a plurality of data and/or communication services, also often called "applications." The CMD 25 (as detailed below in FIG. 2) is typically made operable by a subscriber contracting with a communication service provider (e.g., a wireless carrier) for obtaining wireless communication services. The subscriber may be an individual person, a parent in a family, a business, or any person who wants the services offered to the CMD 25. These types of people may also be an actual user of the CMD 25, or the actual user to be a different person from the subscriber. For example, a parent may be a subscriber for providing communication services to a CMD 25 for one of the parent's teenagers who drives a family vehicle. Alternately, a business (the subscriber) may contract with a wireless carrier to provide communication services to a CMD 25 for one of their employees who drives a company vehicle, as in a transportation vehicle like a bus, or a delivery vehicle, or another type of company-owned vehicle.

The Controllable Mobile Device (CMD) 25 provides the user of the CMD with communication services (e.g., voice, text messaging, email, Internet access, gaming, video, and other services) via a wireless connection 50 through a wireless network 45 from a Mobile Device Service Provider (MDSP) 130 (e.g., a cellular or WiMAX wireless carrier). The MDSP 130 is operational to enable or disable services provided to each CMD 25 and records each instance a user uses a service in a mobile usage database 135.

In addition to the plurality of services available through a Controllable Mobile Device (CMD) 25, the CMD may also provide a unique identification capability which can be detected over-the-air from one or more position detectors and/or sensors 37, 38, 39 (three are shown in FIG. 1) generally positioned in or around the vehicle occupant enclosure 20. The one or more position detectors and/or sensors 37, 38, 39 may be provided as part of the Vehicle Detection System (VDS) 30 as detailed below in FIG. 3. Each of the position detectors 37, 38, 39 has a unique identifier which can be detected over-the-air to verify that detector is still present at the location it was installed. Further, the VDS 35 includes a motion sensing capability to determine when the vehicle 15 is moving and may also include a detection engine 300 (FIG. 3) to combine position information from the one or more detectors and/or sensors 37, 38, 39 to assist in determining the position of the CMD 25 within the vehicle 15. The VDS 30 may also be operational to detect the position of one or more CMDs 25 simultaneously.

In one embodiment of the mobile services control system 10, the Vehicle Detection System (VDS) 30 is operational to send data, via wireless signal 65, to a wireless network 60 (which may or may not be identical to the network 45), and subsequently to Vehicle Service Provider (VSP) 100 also included as part of the system 10 in at least some embodiments thereof. The VSP 100 may be provided by a network/service operator (wireless carrier) which (via the wireless network 60) provides a mobile (wireless) data connection to a plurality of VDSs 30 in a plurality of vehicles 15. Alternatively, the VSP 100 may not be operated by the wireless carrier operating the network 60, and instead is, e.g., operated by an entity that operates the mobile services control system 10. The VDS 30 may physically be located in various positions within the vehicle 15, including, but not limited to, entirely within the vehicle occupant enclosure 20 (e.g., under the dashboard), or entirely outside of the vehicle occupant enclosure 20 (e.g., in the engine or trunk compartments), or partially within and partially outside the vehicle occupant enclosure 20 (e.g., with the VDS base unit 35 under the dashboard and the one or more detectors/sensors 37, 38, and 39 located elsewhere in the vehicle 15).

The vehicle plus mobile detected information (as also described in (c) of the Summary section hereinabove) is transmitted over wireless connection 65 (i.e., to a wireless base station 70), and such information may include position information indicative of whether the Controllable Mobile Device (CMD) 25 is within a restricted zone for the vehicle 15, or outside of the restricted zone, wherein such a restricted zone may be a geospatial envelop (2-dimensional or 3-dimensional) within the vehicle occupant enclosure 20 that is particularly associated with where an occupant would be positioned for operating the vehicle. The vehicle plus mobile detected information may further include detailed information describing a more precise position of the CMD 25 within such a restricted zone. The position information may be defined in a 3-dimensional spatial grid of x, y, and z coordinate offsets from a reference point, which might be a point adjacent to or in the base unit 35 of the Vehicle Detection System (VDS) 30 with optional resolutions in inches or centimeters, etc, or the position information may be provided as a one dimensional distance from, e.g., the detector and/or sensor 37 located near the driver's seat (more generally, the operator's position). Further, the data transmitted via connection 65 may include vehicle state information as to whether the vehicle 15 is moving and the operational status of the VDS 30 itself. In one embodiment, all of the data may be transmitted over the wireless connection 65 to the Vehicle Service Provider (VSP) 100 in a real-time, near-continuous stream of information. Alternately and/or optionally, the CMD may also provide information via 50 to a wireless network 45, the information including but not limited to information about a user's use of one or more services, number of finger pushes, e.g., selection of one or more feature of the phone, number of services used during a segment of distance or time, number of times a password was entered, texting services being used including reading, responding, phone services usage, internet services usage, game services usage, application usage, internet being usage, location of CMD, velocity of CMD, acceleration of CMD, deceleration of CMD, movement of CMD, power of CMD, e.g., was CMD on/off, self-identification of user and combinations of the same.

Alternately and/or optionally, the Vehicle Detection System (VDS) 30 may store the vehicle status information related to each restricted zone, each CMD 25 position, and other data in local non-volatile memory within the VDS for later forwarding to the Safe Driving Registration System (SDRS) 105 via the Vehicle Service Provider (VSP) 100. The VSP 100 may provide multiple network access methods by which the VDS 30 may forward the stored data. In one embodiment, when the VDS 30 enters receive/transmit range of VSP's 100 network 60, the VDS may be operational to transmit the stored data to wireless network base station 70 via wireless signal 65. In another embodiment, the VSP 100 may provide access to the VDS 30 through a data network 90. For example a wireless connection and signaling between the VSP 100 and the VDS 30 may be tunneled through an Internet data connection (e.g., TCP/IP) wherein the data network 90 is used to communicate data to the Mobile Services Control System 10, e.g., when the vehicle 15 resides at the premises 85 as shown in FIG. 1. Examples of this embodiment include, but are not limited to, the user driving their vehicle into a home garage, or a business parking lot, or business depot garage (for commercial uses), wherein the VDS 30 transmits the stored data via an over-the-air connection 75 to an on premises 85 wireless transceiver 80, such as, for example a Wireless Local Area Network (WLAN)/Wi-Fi, femtocell or picocell, Bluetooth, Wireless USB, or some similar connection. The wireless transceiver 80 is operational to connect to a wide area data network, such as, for example, the Internet 90. Alternately and/or optionally, the VDS 30 may use a wired LAN connection 75 at the premises building 85 to connect through the wide area network 90 to the VSP 100.

Alternately and/or optionally, the Vehicle Detection System (VDS) 30 may be configured and operable to transmit the vehicle plus mobile detected information and other data directly to the Controllable Mobile Device (CMD) 25 via an over-the-air connection 40. In this configuration both the CMD 25 and the VDS 30 include vehicle wireless network interfaces, such as, for example a WLAN/Wi-Fi, femtocell or picocell wireless, Bluetooth, Wireless USB, or some similar connection. In this configuration, control software on the CMD 25 may determine what action to take on specific services or applications operating on the CMD, such actions may include, but is not limited to: disabling a specific service, a set of services, or all services on the CMD; enabling a specific service, a set of services, or all services on the CMD; or enabling a specific service, a set of services, or all services on the CMD but also delivering a warning to the user via a CMD user interface. In one embodiment, the vehicle operational status, restricted zone, position, and other data transmitted directly to the CMD 25 via an over-the-air connection 40, may operate directly with a specially constructed battery on the CMD, which in turn disables the entire CMD. The special battery (not shown) may be constructed in the same shape, size, and form of a standard battery for the CMD with the addition of internal digital logic which controls the flow of power from the battery to the CMD wherein the digital logic receives the vehicle operational status, restricted zone, position, and other data transmitted via over-the-air connection 40 and decides whether to enable or disable the flow of power to the CMD.

Alternately and/or optionally, the VDS may be connected to the vehicle, e.g., through the OBDII port of the vehicle, which can provide power to the VDS, as well as other information through the vehicle computer information network. Information provided to the VDS through the OBDII port for communication to the SDD 110 and SDS 125 by transmission wirelessly to the CMD 25 carrier network, or through other wirelessly connected means such as WiFI, either real time, or in a store and forward mode, may include vehicle speed, vehicle location over a segment of travel, vehicle acceleration, information indicative of a hard breaking event, serving event, hard acceleration event, accident, vehicle power on/off, mileage, vehicle maintenance information, RPM, seat position information and other information available to the VDS through the OBDII port in support of limiting distracted driving, or for other business reasons.

The VDS may be connected to vehicle power, either through a direct connection to vehicle wiring, or through a power outlet in the vehicle. In this embodiment, the VDS is not directly connected to the OBDII port, but captures vehicle location and speed information from GPS data collected by a GPS chip connected to the VDS, or by using an accelerometer connected to the VDS, or through changes in cell-tower connection data detected by the wireless cell connection within the VDS, or a combination of the above. Detection of motion via the accelerometer may include detection of vibration indicative of engine operation or vehicle movement, or by integration of acceleration data indicative of velocity. In another embodiment of the invention, the VDS is not connected to vehicle power, but is powered by solar cells on the VDS that is connected to a battery that would be charged by the solar cells and allow operation during periods of darkness.

Returning to FIG. 1, in one embodiment the Vehicle Service Provider (VSP) 100 and the Mobile Device Service Provider (MDSP) 130 may be different business entities wherein the wireless networks 60 and 45 are physically separate and distinct networks which may, or may not, use different wireless technologies. When VSP 100 and MDSP 130 are different service providers data may be exchanged between them via connection 145 when no data format or signaling protocol conversion is needed, or via a Service Provider Interworking function 140 when some type of interworking is necessary. Alternately and/or optionally, the VSP 100 and the MDSP 130 may be the same business entity, or related business entities that act as a single business entity, wherein the wireless networks 60 and 45 may be the same physical network.

The Vehicle Service Provider (VSP) 100 may be operational to deliver the vehicle plus mobile detected information to the Safe Driving Registration System (SDRS) 105 for storage in the Safe Driving Database 110, also included in the mobile services control system 10. The SDRS 105 may be provided by the Vehicle Service Provider (VSP) 100, the Mobile Device Service Provider (MDSP) 130, or a third party service provider as one skilled in the art will understand. The SDRS 105 may store the vehicle plus mobile detected information in a data management system 110, also denoted herein as the Safe Driving Database 110, which may be considered as a component of the system 10 in at least some embodiments. Note that the Safe Driving Database 110 may also contain, but is not limited to, information identifying each subscriber subscribing to the services provided by the mobile services control system 10, registration information identifying the Vehicle Detection System (VDS) 30 for a specific vehicle managed/owned by the subscriber, registration information identifying one or more mobile devices 25 for this subscriber, customizable service control settings (e.g., allowed or restricted services, time-of-day controls, report options, etc.), game parameters including rewards, discounts, locations of redemptions, prechosen user identified categories and awards, and information that describes subscribers to the SDRS 105 (e.g., name, address, etc.). Subscribers subscribing to the services provided by the mobile services control system 10 include, for example, parents who register a vehicle 15 for a teenage child and equip it with the VDS 30 to disable use of the teen's CMDs 25 within that vehicle. Note that other entities may access the subscriber data within the Safe Driving Database 110. These other entities may include, for example, one or more Mobile Device Service Providers (MDSP) 130 which provide mobile wireless services (e.g., voice, text messaging, email, Internet access, gaming, etc.) to, e.g., a teenager's CMD 25. Note that in at least some embodiment of the mobile services control system 10, such providers 130 are not part of the system 10, but instead, are necessary for the operation of the system 10.

Figure 6:
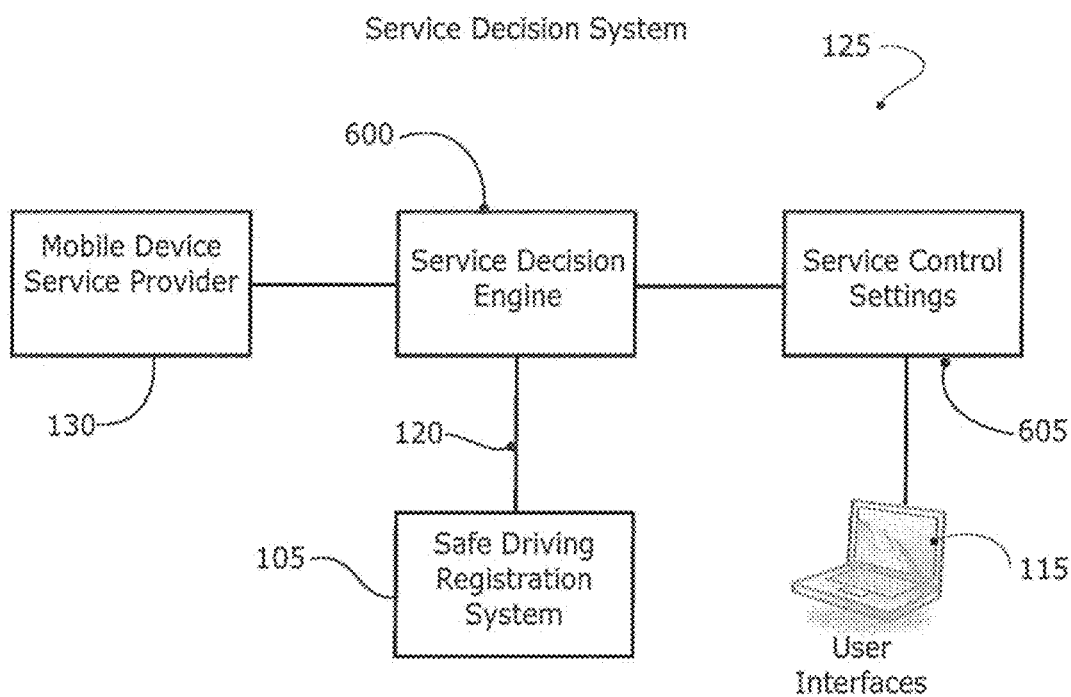
FIG. 6 discloses an illustrative functional block diagram of the Service Decision System.

In addition, the Safe Driving Registration System (SDRS) 105 may be operational to provide user interfaces, such as, for example, Internet web-based interfaces 115 for users (e.g., subscribers to the services provided by the mobile services control system 10) to configure data monitoring, rewards, discounts and service control settings for the one or more vehicles 15 and one or more CMDs 25 such users manage. The service control settings may define which mobile services (e.g., voice, text messaging, email, Internet access, gaming, etc.) to allow and which to disable under which conditions (e.g., when the vehicle is moving). Alternately and/or optionally service control settings may be provided as part of the Service Decision System 125 (FIGS. 1 and 6). Further, the SDRS 105 may provide each subscriber with configurable settings for receiving alert messages, game score, information about the vehicle and/or CMD, the alert message can include information about a vehicle 15, registered with the mobile services control system 10, is in operation and/or when a registered Controllable Mobile Device (CMD) 25 is turned on in the moving vehicle 15, and/or when a registered CMD is within a restricted zone of the vehicle 15). The alert messages may include, but are not limited to, a text message, and email message, or a phone call to the subscriber alerting the subscriber about the operational status of the registered vehicle 15 or the registered CMD 25. The SDRS 105 may also provide user interfaces 115 for the subscriber or third-party to access reports of the vehicle 15, alerts, score, and CMD 25 status or usage, or the SDRS may automatically generate reports.

In one embodiment, the Safe Driving Database 110 (and/or the SDRS 105) is configured to generate a score, e.g., game score, based on one or more of the following; did the driver self-identify themselves during the trip as a driver, frequency of use of one more services of the CMD, location of vehicle, acceleration, deceleration, number of perfect distance segments (number of times a predetermined distance was driven without an event indicating distracted) that satisfy a predetermined criteria, e.g., without using one or more services on the CMD that could be distracting, that the driver did not override the distracted driving control system, that they handled the CMD a certain way, or a certain number of times, that they pressed button on the CMD a certain amount of times, number of times one or more services of the CMD is overridden, power of the CMD, e.g., off or one, use and/or movement of CMD, e.g., was a text looked at or answered or usage, was the phone answered or usage, fuel economy of travel and combinations of the same. The game score can also be based on the number of perfect distance segments driven in sequence (a streak), so that the longer the streak, the greater the score, or score multiplier. The Safe Driving Database may also be configured to allow team competitions to occur, where multiple drivers can combine their scores to compete against other groups of multiple drivers, the groups being chosen by the drivers or by a third party. The Safe Driving Database 110 (and/or the SDRS 105) is configured to communicate with the internet, e.g., social media including Twitter, Facebook, Advertiser, e-commerce, and the like, thereby allowing a subscriber, user or third-party to post the score, results, team results, notification of team rewards, provide discounts, provide awards, team competitions, leader boards and the like.

In one embodiment, the Safe Driving Database 110 (and/or the SDRS 105) may be hosted in a network, such as, any location or network site connected to the Internet and independently operated from the VSP 100 and/or MDSP 130. Alternatively, the Safe Driving Database 110 (and/or the SDRS 105) may be hosted at a location or network site administered by a network-based VSP 100, or by a network-based MDSP 130, wherein the Safe Driving Database 110 (and/or the SDRS 105) may be operated by the VSP 100, the MDSP 130, or by a third-party. As such, the Safe Driving Database 110 may operate as a national database monitoring and managing all registered vehicles 15 with multiple mobile service providers 130 that are able to access the Safe Driving Database 110. Alternately, the Safe Driving Database 110 may be operated by an independent "third party" company (e.g., a software or insurance company) for a specific set of subscribers, and/or within a specified geographic region, or the Safe Driving Database may be managed and operated by the Vehicle Service Provider (VSP) 100 or the Mobile Device Service Provider (MDSP) 130.

In one embodiment, the Safe Driving Registration System (SDRS) 105 may be implemented as two or more modules, where one or more of those modules is hosted on a subscriber's computing platform, such as, for example, a home personal computer, a subscriber's mobile device, or some similar platform, and with one or more other modules hosted in a service provider 130 network. This arrangement allows distributed report and control management from a remote subscriber computer. In yet another embodiment, all modules of the SDRS 105 may be located on a subscriber computing platform.

In one embodiment, the registrations of one or more CMDs 25 are associated in the SDRS 105 with the registration of the VDS 30 for a specific vehicle 15. The mobile services control system 10 may simply be operable to control services (enable or disable) on the one or more registered CMDs 25 whenever motion is detected by the VDS 30 in the associated vehicle 15, or alternately stated, the system 10 does not detect the presence or position of a CMD 25 within the registered vehicle 15, and instead assumes that services on the one or more registered CMDs 25 should be disabled whenever the vehicle 15 is in motion. With this configuration of mobile services control system 10, there may be situations where the subscriber to the mobile control services system 10 knows that the user of CMD 25 (e.g., their teenaged child, or their employee) will not be using the associated vehicle 15 (registered through the vehicle's VDS 30) on a particular day, or during a particular time. In such situations, the vehicle 15 may be used by another person and may be moving while the subscriber knows the registered CMD 25 is not in the vehicle 15. A similar situation may arise when the subscriber and user are one in the same person and that person drops their vehicle 15 off at an auto repair shop for work during the day and takes their registered CMD 25 with them. Throughout that day the vehicle 15 may be driven by repair shop personnel, but the CMD 25 is with the subscriber/user where it is desirable to allow full use of the CMD 25 services.

Alternately and/or optionally, the mobile services control system 10 may be operational to provide an override function to the subscriber or user of the mobile services control system 10 which allows the subscriber or user to temporarily override the control of services on the CMD 25 by selecting an option via a user interface 115 (e.g., an Internet web interface, a mobile device interface, some other computer interface, etc.), or via an option displayed on the CMD 25. Alternately and/or optionally, the override may be initiated by the user of the CMD 25 by sending a simple text message or voice message to a specified number designated by the Service Decision System 125, or alternately, the Safe Driving Registration System 105 to receive override messages, such message initiating the override for a specific amount of time specified by the user of the CMD 25 via the message. In such a case, the Service Decision System 125 or alternately the Safe Driving Registration System 105 may send an email or voice or text alert to the subscriber of the mobile services control system 10 that may also include information of the times that the associated vehicle 15 was in motion in relation to the time of the override. These text alerts then provide a method for the subscriber to change the configuration of the mobile services control system 10 to disallow user of CMD 25 to self-generate override messages if this feature is being abused. Alternately and/or optionally, in one embodiment, when: (i) the VSP 100 and MDSP 130 are operated by the same business entity, and wireless networks 45 and 60 are one in the same network (or substantially so), or (ii) the VSP 100 and MDSP 130 are different business entities but are sharing information to support increased operability of the Mobile Services Control System 10, then in either case, information related to the location of the base stations in wireless communication with the CMD 25 and VDS 30 (e.g., base stations 70 and 55 in FIG. 1, and which may be the same base station) may be used to programmatically deduce whether the Controllable Mobile Device (CMD) 25 is possibly within the vehicle 15 having the VDS 30, or probably not within the vehicle 15. If the VDS 30 is connected to a unified wireless network, including both the network 60 and the network 45 (herein the combined network also denoted 60+45) through one base station 70, but the CMD 25 is connected through a different base station 55 then the mobile services control system 10 may use this information and predefined geographical information about the locations of base stations 70 and 55, to determine if the CMD 25 is physically in a different location from the location of the VDS 30 and vehicle 15. If the mobile services control system 10 concludes that the CMD 25 is not in the same base station area as the vehicle's 15 VDS 30 then the mobile services control system may temporarily suspend control of services on the CMD 25. Alternately and/or optionally, this determination may be made by the location of VDS 30 with respect to CMD 25 by triangulation and calculation of multiple cell tower signals received from VDS 30 and CMD 25. Alternately and/or optionally, since information indicative of relative signal strength from wireless communication changes with movement of a CMD 25, such movement can be used to determine the approximate velocity of both the VDS 30 and CMD 25, and such approximate velocities can be compared to conclude if the CMD 25 is in the same vehicle as the VDS 30, and if not, temporarily suspend control of services on the CMD 25.

In one embodiment of the mobile services control system 10, the Services Decision System 125 may be operational to receive the vehicle plus mobile detected information (e.g., vehicle operational status, CMD position information, CMD use information, override, self-identification, auto-identification, restricted zone data, etc.) and service control settings (e.g., subscriber service selections, awards, discounts, subscriber preferences, service provider options, etc.) to determine for each managed communication service whether to enable or disable the service. The vehicle plus mobile detected information may be received by the Service Decision System 125 periodically at set intervals or in a real-time near-continuous stream of data. A high level flowchart of the processing performed by the Service Decision System 125 is described herein below, and illustrated in FIG. 7.

In one embodiment, the Service Decision System 125 may be operational to connect with the Mobile Device Service Provider (MDSP) 130 or third-party source to receive the vehicle plus mobile detected information from the MDSP via the Vehicle Service Provider (VSP) 100 from the Safe Driving Registration System (SDRS) 105 where the vehicle plus mobile detected information is stored in the Safe Driving Database 110. Data is transmitted to and from between the MDSP 130 and VSP 100 via a direct connection 145 when a compatible data format and signaling interfaces exist, or alternately/optionally via Service Provider Interworking function 140 when some type of data format or signaling conversion is necessary. The vehicle plus mobile detected information may be transmitted based on service provider access parameters by periodic polling and "pull" requests from the MDSP 130 to the Safe Driving Registration System (SDRS), or based on event-driven "push" transmissions from the SDRS 105 to the MDSP 130. In one embodiment, thes vehicle plus mobile detected information is transmitted in a real-time data stream to allow real-time control of the plurality of services on each CMD 25 as it is moved in and out of the restricted zone in the vehicle occupant enclosure 20. In this later configuration, the Service Decision System 125 forwards the determinations it makes (e.g., to enable or disable a specific service) on to the MDSP 130 which, in turn, may enable or disable one or more of the services on the CMD 25. Further, in this configuration, the Service Decision System 125 may be physically hosted by the MDSP 130 in the MDSP's network, or hosted by a third party service provider, which may, or may not, be the same service provider hosting the Safe Driving Registration System (SDRS) 105 and/or Safe Driving Database 110.

Alternately and/or optionally, the Service Decision System 125 may be operational to connect directly via communications path 120 and/or path to user interfaces 115 to the SDRS 105 to receive the vehicle plus mobile detected information from the SDRS 105 without transiting the VSP 100 and MDSP 130. In this configuration, data may still be transmitted between the SDRS 105 and Service Decision System 125 using a polling ("pull"), or event-driven ("push") method, or real-time near continuous stream. In this configuration, the Service Decision System 125 forwards the determinations it makes to enable or disable a CMD 25 specific service to the SDRS 105 which sets an enable/disable flag for each such service in the SDRS, which the MDSP 130 is then operational to query that flag via a "pull" request or "push" notification. Further, in this configuration, the Service Decision System 125 may be physically hosted by the same service provider hosting the Safe Driving Registration System (SDRS) 105 and/or Safe Driving Database 110, or possibly by a third party service provider.

The Service Decision System 125 also provides a user interface 115 (e.g., a computer software interface, an Internet web interface, a mobile device interface, or some other user interface) for subscribers, users or third-parties to view and manage their service control settings, for administrators of the Mobile Device Service Provider (MDSP) 130 to manage operational settings, scoring parameters, e.g., game parameters, awards, offered discounts, advertisements, and/ or for administrators of the SDRS 105 to manage operational parameters.

Figure 2:
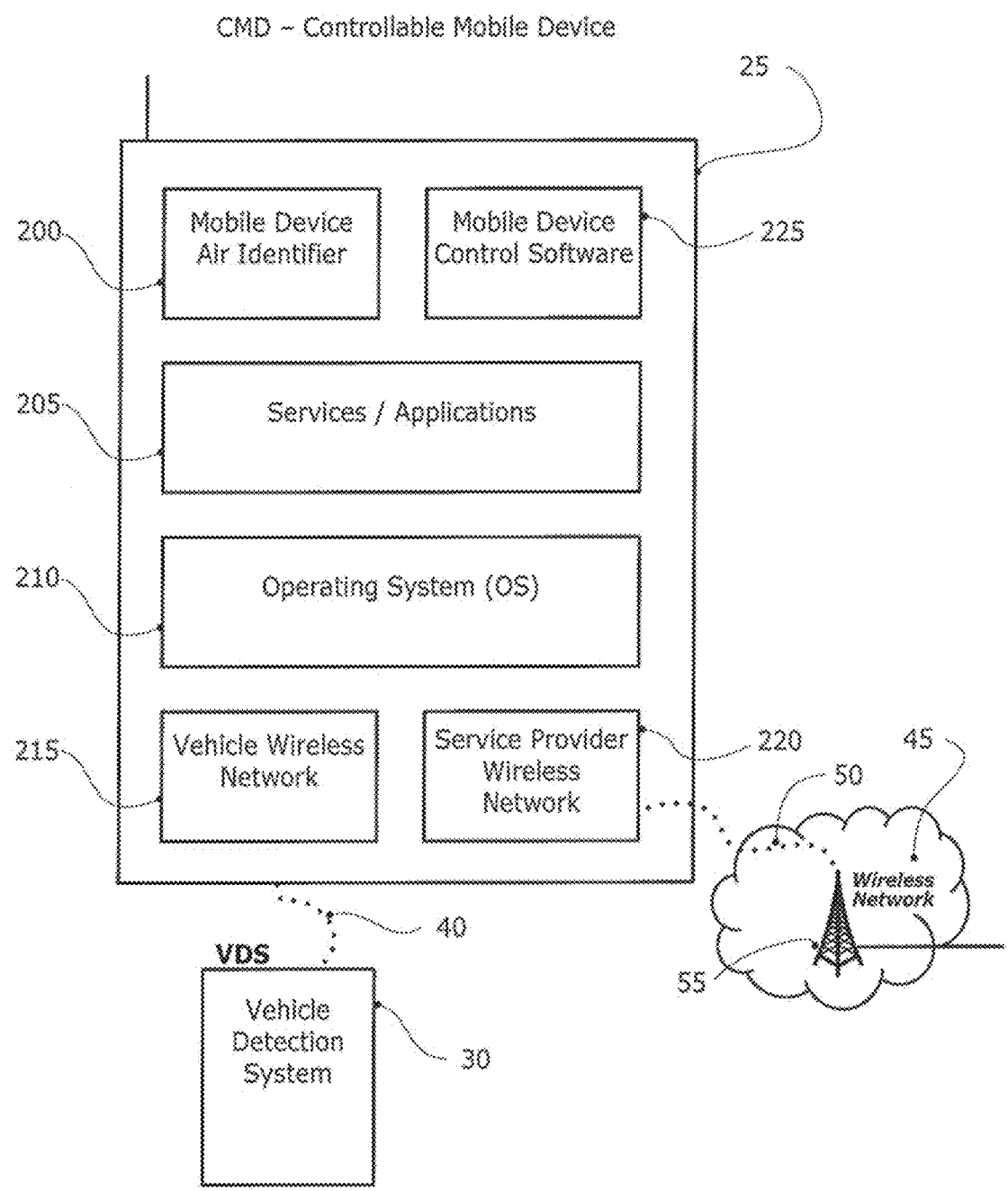
FIG. 2 discloses an illustrative functional block diagram of the Controlled Mobile Device (CMD).

Disclosed in FIG. 2 is one embodiment of the functional components that may be provided on a Controllable Mobile Device (CMD) 25. The CMD 25 may be a cell phone, smart phone, Personal Digital Assistant (PDA), a personal computer with wireless network connectivity, a mobile digital TV, an in-vehicle navigation system, or any other mobile communication device which offers services, also known as "applications," to a user. For the present disclosure, such mobile communication devices 25 include various mobile communication devices that can be moved in and out of a vehicle 15 or moved around within a vehicle 15, as well as devices that move with the vehicle 15, that is, devices that may be built-in to a vehicle (e.g., a navigation system), but nonetheless provide services that may be distracting to a driver while the vehicle is moving. One with ordinary skill in the art may envision built-in vehicle navigation systems one day providing all of the typical cell phone services like voice, text messaging, video, Internet access, mobile DTV, and games. As such, to control the use of potentially distracting services on a mobile communication device within the restricted zone of a moving vehicle, devices fixed to the vehicle, (e.g., attached to, or built-in, as CMDs) are disclosed herein that assist in controlling a driver using such services.

The implementation of the Controllable Mobile Device (CMD) 25 may include an operating system 210 and a plurality of services/applications 205, including, but not limited to, voice, text messaging, video, Internet access, games, and other types of service. The term "service" in the present context, includes interactive mobile communication services, display or output only services, and input only services. The CMD 25 may also include a vehicle wireless network interface 215 which supports a typical wireless local area network (WLAN), for example, Wi-Fi, or some other wireless local network capability, like, for example, femtocell or picocell wireless, Bluetooth, Wireless USB, etc. The vehicle wireless network 215 may be configured for wireless connection to the Vehicle Detection System (VDS) 30, or other wireless devices in proximity to the CMD 25. In addition, as a mobile device, the CMD 25 also provides a service provider wireless network interface 220 which connects the CMD 25 to the Mobile Device's Service Provider (MDSP) 130 (i.e., wireless network 45), shown in FIG. 1, over a wireless connection 50.

The Vehicle Detection System 30 (VDS) may be operational to detect a Controllable Mobile Device 25 (CMD) through the Mobile Device Air Identifier 200 (FIG. 2). In one embodiment the Mobile Device Air IDentifier 200 is (or includes) a Radio Frequency IDentifier (RFID) transponder (also known in the art as a "tag"). The Mobile Device Air IDentifier 200 may be built-in to the CMD 25 and completely contained within the CMD, or the Mobile Device Air IDentifier 200 may be attached to the CMD with some form of adhesive to place it on the outer surface of the CMD, or the Mobile Device Air IDentifier 200 may be integrated with the battery for the CMD, where such batteries may be provided as an after-market component for the CMD. Such an attached Mobile Device Air IDentifier 200 may be affixed in such a way so as to prevent tampering, wherein such tampering may include removal of the Mobile Device Air IDentifier 200 or covering of the Mobile Device Air IDentifier 200 with a material which occludes the radio frequency signal from reaching the Mobile Device Air IDentifier 200. Further, the Mobile Device Air IDentifier 200 may be "passive," without a power source, or it may be an "active" tag by drawing power from the CMDs power source. There are multiple advantages to the Mobile Device Air IDentifier 200 being an active RFID tag. In particular, the following advantages may be provided: (i) the detectors 37, 38, 39 (disclosed in FIG. 3) may require less power to sense the RFID tags, (ii) such an active RFID tag may be sensed over a greater distance, and (iii) there may be greater accuracy in reading the identity of an active RFID tag. The Mobile Device Air IDentifier 200 may be used for routing mobile device position information by the Vehicle Service Provider (VSP) 100 to the appropriate Mobile Device Service Provider (MDSP) 130.

Alternately, the Vehicle Detection System (VDS) 30 and CMD 25 may be operational to use another over-the-air identification and position detection technology other than RFID, such as, using acoustic methods such as ultrasound, using optical technologies such as InfraRed (IR), or other similar technologies for determining the position of the CMD relative to the VDS.

The Controllable Mobile Device (CMD) 25 may further be operational to support control software 225 (FIG. 2) which provides the ability to control—that is, monitor, enable, disable, and report on—other services 205 provided on the CMD. The control software 225 may receive data or instructions as input from the VDS 30 via wireless connection 40 (FIG. 1) or from the Mobile Device Service Provider (MDSP) 130 via wireless connection 50.

Figure 3:
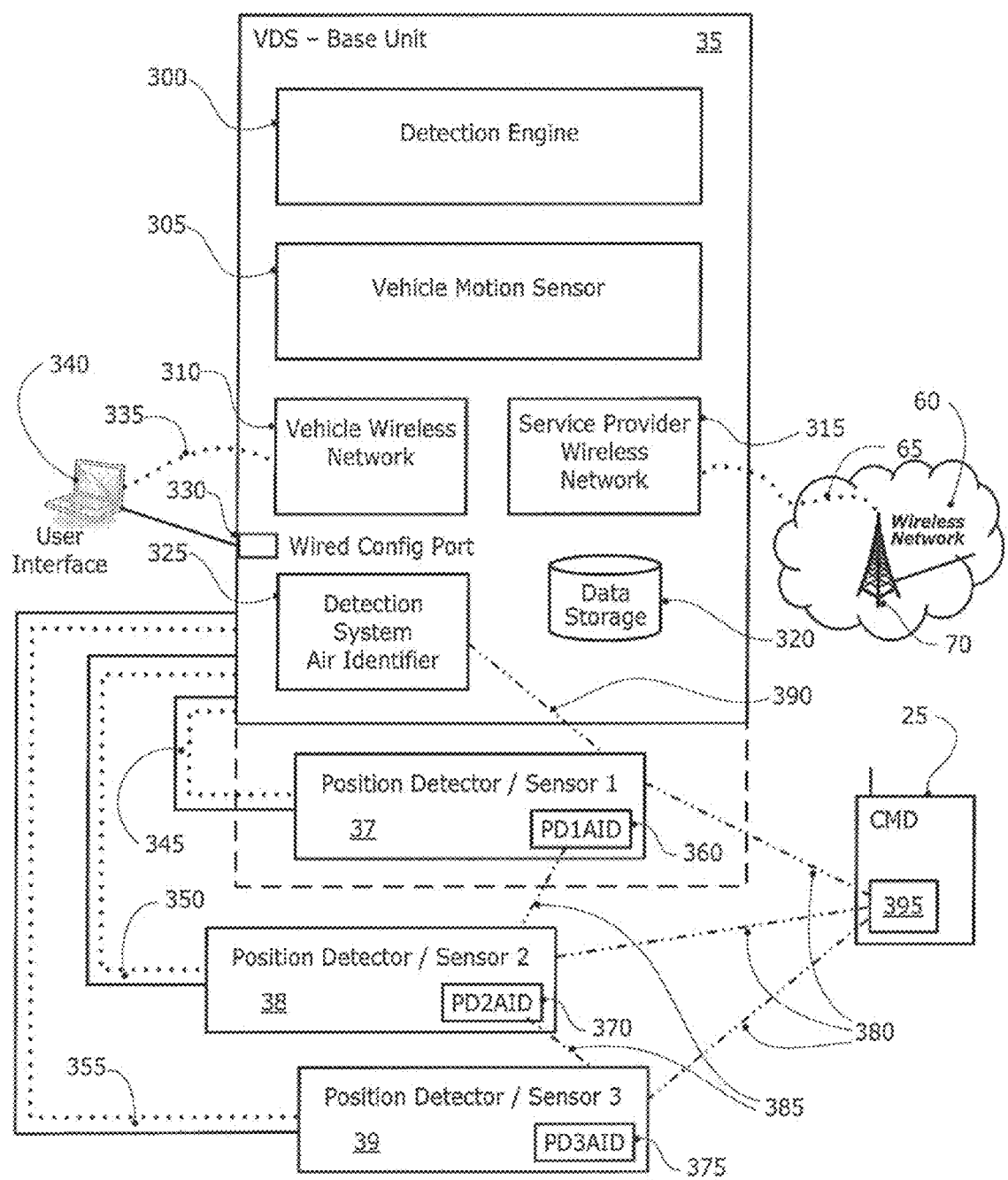
FIG. 3 discloses an illustrative functional block diagram of the Vehicle Detection System (VDS).

Disclosed in FIG. 3 is one embodiment of the functional components that may be provided on a Vehicle Detection System (VDS) 30. The VDS 30 may be a single hardware unit, or multiple hardware components each hosting various functions as described below. Each hardware component of the VDS 30 may be factory installed at the time a vehicle is manufactured and therefore built-in to the dashboard, engine compartment, ceiling, molding, or other parts of the vehicle, and in general, out-of-sight from users. Alternately and/or optionally, the one or more hardware components of the VDS 30 may be "after-market installed" at some point in time after the vehicle has been shipped from the manufacturer. After-market components may be visible to the user, or designed to blend-in with other parts of the vehicle, and may receive wired, or perhaps wireless power, from the vehicle's power, or they may be battery powered, or powered from some other energy source, such as, for example, solar power, wind power through vehicle movement, or possibly by converting the kinetic energy of the vehicle motion to electrical power, or other power sources. In one embodiment, the Vehicle Detection System (VDS) 30 base unit 35 may be configured with a single position detector/sensor 37 in a small, molded unit (also referred to herein as a "pod") which may be mounted under the dashboard of vehicle 15, or on or near the steering column in close proximity to a fuse box thereby allowing a straightforward connection to the vehicle's power. In another embodiment, the pod may directly connected to the On Board Diagnostic (OBD) interface that is available in all US vehicles manufactured after 1996, so as to both provide power, and provide information on the status of the vehicle 15 including whether it is powered, and therefore implying that it is in motion, or velocity information directly, such information to be used by the VDS 35 to establish the status of the vehicle.

As disclosed in FIG. 3 the Vehicle Detection System (VDS) 30 may be operational to provide a vehicle motion sensor 305 capability which senses when the vehicle is in motion. The vehicle motion sensing 305 capability may be configured to sense any motion, such as, for example, less than 1 mile per hour, or it may be configured to consider motion to be any speed over 5, or 10 miles per hour, or the sensing capability may be configurable by adjusting a control (e.g., a knob, or button, or a software configurable control) on the vehicle motion sensor to set the threshold speed limit. Examples of vehicle motion sensing 305 functionality include, but are not limited to, an accelerometer, a GPS tracking device, the speedometer built-in to the vehicle, or other similar motion sensing devices. Alternately, or in addition to, the vehicle motion sensor 305 may infer vehicle motion from power being turned on in the vehicle 15, by conversely indicating the vehicle 15 is not in motion by the absence of power to the vehicle (the vehicle key being turned off).

Figure 4:
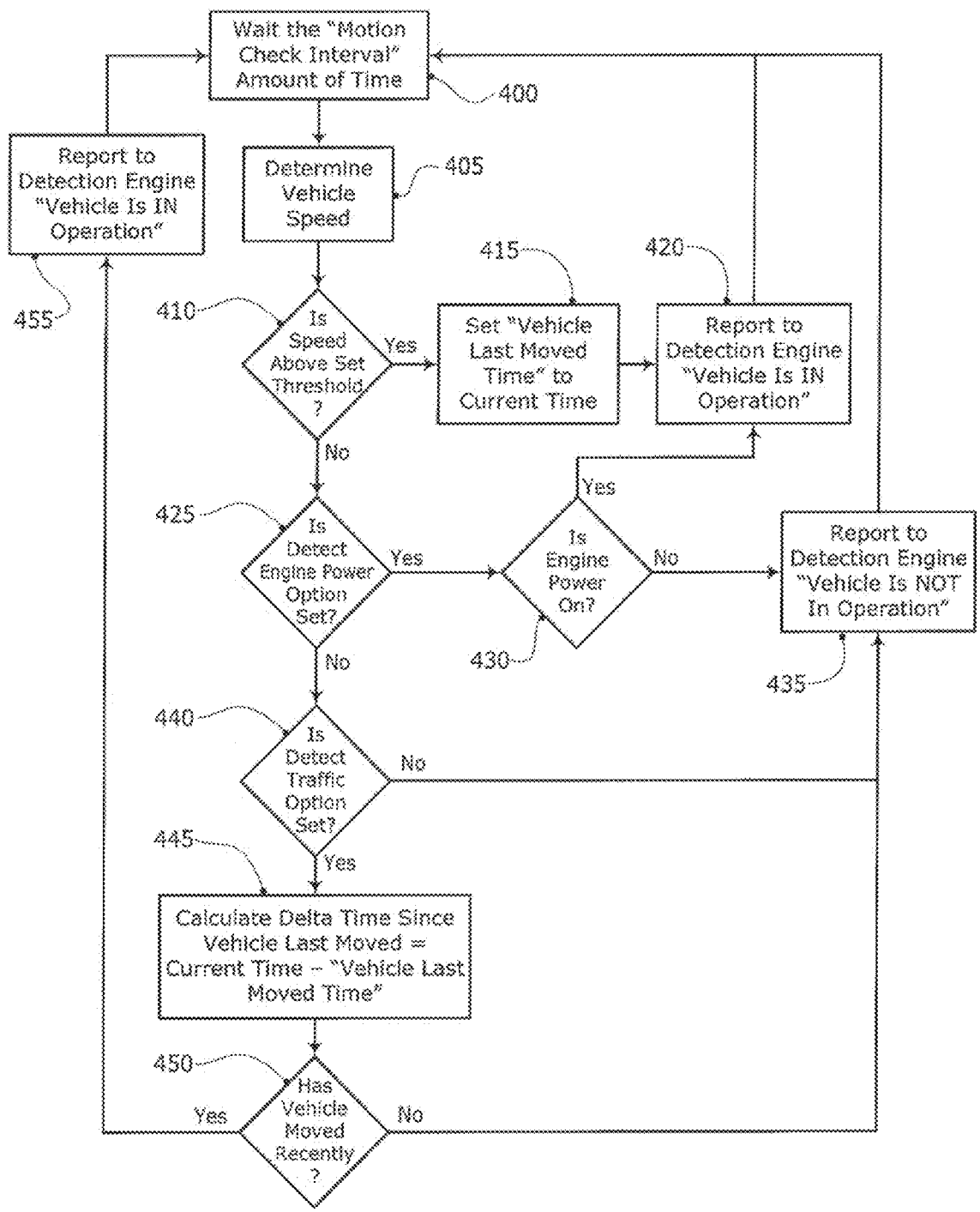
FIG. 4 discloses a flowchart for the Vehicle Motion Sensor logic.

Disclosed in FIG. 4, the vehicle motion sensor 305 may report the vehicle is in operation to the Safe Driving Registration System (SDRS) 105 based purely on whether the vehicle 15 is in motion (steps 405, 410) or not. As such, when the vehicle 15 comes to a stop (e.g., at a traffic red light), or when the vehicle's speed drops below the minimum threshold (step 410) (e.g., in congested traffic), then the vehicle motion sensor 305 may signal that the vehicle is no longer moving. When the vehicle 15 moves again, the vehicle motion sensor 305 may signal that vehicle motion is occurring. This moving, not moving, moving, not moving change of status, however, might intermittently enable services (e.g., text messaging) during those brief periods the driver has stopped or slowed down. It may be desirable to disable services when a vehicle is in slow traffic or stopped briefly at a traffic light. In one embodiment, if the vehicle 15 slows below the threshold speed (step 410) and if the engine is still powered on (step 425), the vehicle motion sensor 305 concludes the vehicle is in operation (step 420) and waits a configured amount of time to check the motion status again in step 400.

Alternately and/or optionally, the vehicle motion sensor 305 may report the vehicle is in operation to the SDRS 105 based on a combination of current movement or recent movement (e.g., within the past 2-4 minutes, or some configurable amount of time). If the detect traffic option (as determined in step 440) is set in the vehicle motion sensor 305, then the logical combination would prevent intermittent use of CMD 25 services during traffic stoplights, or in stop-and-go congested traffic whereby the vehicle motion sensor 305 would continuously report the vehicle 15 is in operation until it is no longer moving. Recent motion is calculated (step 445) by continually updating a time variable each time the vehicle motion sensor 305 determines that the vehicle is in motion 415 as the difference between the current time and the vehicle last moved time. If the vehicle speed (as determined in step 405) is below the threshold (step 410) and the detect traffic option (as determined in step 440) is on, and the vehicle 15 has not moved recently, then the vehicle motion sensor 305 reports to the VDS detection engine 300 that the vehicle is not in operation in step 435. Otherwise, if the vehicle 15 has moved recently then the vehicle motion sensor 305 reports the vehicle is in operation in step 455.

The vehicle motion sensor 305 may report the raw data including vehicle speed, g-force data, engine power state, the vehicle last moved time, and the detect traffic option to the SDRS 105 via the VSP 100 where the SDRS 105 would be operational to provide the vehicle motion sensor logic to determine whether brief traffic stops or congested traffic constitute that the vehicle is in operation, or not. Alternately and/or optionally, the vehicle motion sensor 305 may only report state changes to the SDRS 105 (e.g., the vehicle 15 is in operation, or the vehicle is not in operation), or the vehicle motion sensor may regularly and periodically report (e.g., every minute, or every few seconds, a real-time stream, or some such appropriate interval) the current status to the SDRS 105. Alternately and/or optionally, the Service Decision System 125 may provide the vehicle motion sensor logic with the raw data transmitted from the VDS 30 to the Service Decision System via the SDRS 105.

Returning to FIG. 3, the Vehicle Detection System (VDS) 30 may also include a vehicle wireless network interface function 310 which supports a typical wireless local area network (WLAN), for example, Wi-Fi, or some other wireless local network capability, like, for example, Bluetooth, Wireless USB, etc. The vehicle wireless network 310 may be configured for wireless connection to one or more CMDs 25 and/or for wireless connection to the one or more position detectors and/or sensors, identified in FIG. 3 as 37, 38, 39 that are part of the VDS 30. In addition, the VDS 30 also provides a service provider wireless network interface 315 which connects the VDS to the Vehicle's Service Provider (VSP) network, 60 shown in FIG. 1, over a wireless connection 65. The vehicle wireless network 310 may be configured to detect free-access local networks such as free-access WiFi, and automatically connect to these to download store-and-forward data to the Safe Driving Registration System (SDRS) 105.

The Vehicle Detection System (VDS) 30 may also include a detection engine 300 (e.g., a hardware/software configuration of computational equipment) which determines whether a detected Controllable Mobile Device (CMD) 25 is within a restricted zone while the vehicle 15. In one embodiment the detection engine 300 is in communication with one or more of a plurality of position detectors and/or sensors 37, 38, 39 to receive real-time position information about one or more Controllable Mobile Devices 25. The detection engine 300 also receives motion sensing information from the vehicle motion sensor 305 and possibly engine powered on/off information from the vehicle 15. If the vehicle motion sensor 305 uses an accelerometer to provide motion sensing information, the detection engine 300 may be operational to discern vibrations associated with vehicle motion from other motions caused by other sources such as wind, or movement within the vehicle 15.

In one embodiment, the Vehicle Detection System (VDS) 30 may receive motion sensing information from the CMD 25, via the Mobile Device Service Provider (MDSP) 130, which may include, but is not limited to, a GPS capability built-in to the CMD, or motion determination by the MDSP wireless network, such as, for example, triangulation of signals between multiple cellular radio frequency towers, or other means available in the MDSP to determine motion of the CMD. In one variation of this embodiment, the motion sensing information is determined by the MDSP 130 and relayed via the Vehicle Service Provider (VSP) 100 over wireless connection 65 to the VDS 30, where the MDSP and VSP may be the same network service provider. In another variation, the motion sensing information may be relayed by the MDSP 130 back to the CMD 25 via wireless connection 50 and then transmitted by the vehicle wireless network 215 on the CMD to the vehicle wireless network 310 on the VDS.

The detection engine 300 further may be operational to provide the ability to define a "restricted zone" within the vehicle wherein CMDs 25 are detected and possibly services on the Controllable Mobile Device (CMD) are disabled. In one embodiment, such a restricted zone is configurable by the person who installs the Vehicle Detection System (VDS) 30 or possibly by the subscriber. The detection engine 300 of the VDS 30 may provide a wired configuration port 330, such as, for example a serial port, a USB port, or similar interface technology, to allow a computational device, such as, for example, a personal computer, a notebook computer, a PDA, or even a mobile phone, to connect to the detection engine and provide a user interface 340 for configuring the restricted zone. The user interface (UI) may be graphical, or numerical, or some such appropriate UI. The connection between the detection engine 300 and the computational device may be wired or a wireless connection, and it may use the vehicle wireless network interface 310, for example a Wi-Fi connection. Alternately and/or optionally, the detection engine 300 may provide a default restricted zone.

The Vehicle Detection System (VDS) 30 may further be operational to provide a Detection System Air Identifier 325. In one embodiment the Detection System Air IDentifier 325 includes a Radio Frequency IDentifier (RFID) transponder or tag. The one or more position detectors and/or sensors 37, 38, 39 may be operational to read the Detection System Air IDentifier to verify that the Detection System Air IDentifier is readable, thereby deducing that the VDS base unit 35 (FIG. 1) has not been obstructed and occluded from detecting one or more CMDs 25. Further, the position detectors and/or sensors 37, 38, 39 read the Detection System Air IDentifier 325 to confirm the location of the Detection System Air IDentifier, relative to its initial location at the time of installation, and thereby confirm that the VDS base unit 35 has not been moved, which could alter the restricted zone. The Detection System Air IDentifier 325 helps prevent tampering of the VDS base unit 35. The Detection System Air IDentifier 325 may be passive, without a power source, or it may be an active tag by drawing power from the VDS's power source. Alternately, the Detection System Air IDentifier 325 may be a similar over-the-air identification and position detection technology other than RFID.

Alternately and/or optionally, the VDS 30 may be operational to detect and identify a Controllable Mobile Device (CMD) 25 via one or more wireless signals from the CMD 25. This includes, but is not limited to, detection and identification via the local area vehicle wireless network capability 310 in the VDS 30 and corresponding local area wireless network capability 215 in the CMD 25 over wireless connection 40 wherein the presence of a specific CMD 25 may be detected and identified. Alternately and/or optionally, the VDS 30 may be operational to receive and connect with the wireless network signal 50 (e.g., the cellular or some such similar technology) from the CMD 25 intended for the MDSP 130 service provider through the MDSP's wireless network 45 wherein the VDS 30 may be operational to have the necessary encryption codes and wireless signaling technology to read the wireless network signal 50 and through that signal identify the specific CMD 25.

The VDS base unit 35 configuration of the Vehicle Detection System (VDS) 30 may include the detection engine, 300 vehicle motion sensor 305, Detection System Air IDentifier 325, vehicle wireless network 310, and service provider wireless network 315 components or functions. The VDS base unit 35 may also include one of the position detectors 37, 38, 39.

As described above, the Vehicle Detection System (VDS) 30 may yet be operational to provide one or more position detectors and/or sensors 37, 38, 39. In one embodiment, each position detector 37, 38, 39 includes a Radio Frequency IDentifier (RFID) reader. Each such RFID reader transmits a signal 380 wirelessly which any of the RFID tags in the area pick-up and in turn each tag transmits it's ID number, and possibly other data including driver ID, back to the reader. Passive tags use the signal from such a reader to generate enough power for the tag to transmit the response. The VDS 30 may provide one or more RFID readers as position detectors and/or sensors 37, 38, 39. A configuration of one reader could be placed in the dashboard area of a vehicle and provide approximately a circular detection area as the restricted zone. In this implementation the single position detector 37 (one RFID reader) may be implemented in the same component (a single "pod") along with all of the other VDS functions described above. Alternately, or in addition to, the single position detector 37, could be implemented in a separate physical component from the other base unit VDS 35 functions.

Additional position detectors and/or sensors 38, 39, for example, a total of three detectors and/or sensors 37, 38, 39 placed at appropriate distances from one another, may allow the detection engine 300 of Vehicle Detection System (VDS) 30 to triangulate the exact position of a CMD 25, by comparing relative response signal strengths, and thereby determine whether it is within a restricted zone. The triangulation logic employs standard algorithms to calculate a more accurate position of the CMD 25. In one embodiment, the VDS 30 may use one or two detectors and/or sensors 37, 38, 39 to determine the approximate position of the CMD 25 by also detecting the relative strength of the RFID signals with respect to the known location of the detectors and/or sensors 37, 38, 39, and thereby approximate whether the CMD is within the restricted zone. The VDS 30 may support more than three position detectors and/or sensors 37, 38, 39 depending on the position accuracy needed and the size of the vehicle.

Each position detector 37, 38, 39 may be connected to the VDS base unit 35 by a wired connection 345, 350, 355 for transmitting detected information to the detection engine 300 along with providing power to each of the remote position detectors and/or sensors 37, 38, 39. Alternately, each position detector may provide it's own vehicle wireless network interface, such as, for example, Wi-Fi, to transmit data wirelessly 345, 350, 355 to and from the VDS base unit 35. Wireless position detectors and/or sensors 37, 38, 39 may receive power from some other source, such as, for example, batteries, solar power, wireless power, wind power through vehicle movement, or other power sources.

Further, each position detector 37, 38, 39 may also be configured with a Position Detector Air Identifier 360, 370, 375, such as, for example, an integrated RFID tag, within the detector which is configured to respond to the queries of other detectors and/or sensors (e.g., RFID readers). At the same time, each position detector is configured to ignore it's own Position Detector Air Identifier. FIG. 3 illustrates one embodiment of the Vehicle Detection System (VDS) 30, wherein the Position Detector Air IDentifiers in each position detector are labeled PD1AID 360, PD2AID 370, and PD3AID 375. The purpose of the other Position Detector Air IDentifiers is to provide a multi-way "heart-beat" capability for other detectors and/or sensors to confirm that each detector and/or sensor is still detectable, and that the other position detectors and/or sensors 37, 38, 39 are at the location they were originally installed. In a preferred embodiment the Position Detector Air IDentifiers located within each position detector are not isolated, but rather are connected to the position detector and the power source of the position detector. As such, when each Position Detector Air Identifier is polled for a heart-beat response it may be able to provide a smart-heart-beat response including status information about the detector and/or sensor itself. In addition, the VDS base unit 35 may be able to exchange other status information with each detector and/or sensor.

The Vehicle Detection System (VDS) 30 may additionally be operational to detect wireless signal 380 from one or more Controllable Mobile Devices 25 in parallel within the restricted zone and to process that data through the detection engine 300 and to transmit that data to the VPS 100 via the service provider wireless network 315 interface in an interleaved, virtually simultaneous fashion.

In one embodiment, the Vehicle Detection System (VDS) 30 may use other technology methods to detect the position of one or more CMDs 25 within a restricted zone. These include, but are not limited to, detecting the strength of an electromagnetic signal from the CMD 25, such as, for example, a radio frequency signal, which may emanate from the Bluetooth or Wi-Fi capability on the mobile device, or from the cellular signal of the mobile device, or from a different electromagnetic signal source on the CMD 25.

In a further embodiment, the detection engine 300 of the Vehicle Detection System (VDS) 30 may compare the absolute position of the Controllable Mobile Device (CMD) 25 to the absolute position of the VDS base unit 35 to determine if the CMD is within the relative boundary of the restricted zone. In this configuration, the absolute position of the CMD 25 may be determined by multiple methods, including, but not limited to, the Mobile Device Service Provider (MDSP) 130 using the signal strength from its wireless network base stations 55 to triangulate the position of the CMD, or by a GPS location capability built-in to the CMD 25 in operation with a GPS network and the MDSP 130. Further, in this configuration, the absolute position of the VDS 30 may be determined by multiple methods, including, but not limited to, the Vehicle Service Provider (VSP) 100 using the signal strength from its wireless network base stations 70 to triangulate the position of the VDS 30, or by a GPS location capability built-in to the VDS 30 in operation with a GPS network and the VSP 100. Both the MDSP and the VSP, or the GPS network, are operational to transmit the determined absolute position, probably stated in geographical coordinates, to the VSP via wireless network connection 65 where the detection engine compares the absolute positions of the CMD 25 and VDS 30 with the relative boundary of the restricted zone.

In yet another embodiment, the Vehicle Detection System (VDS) 30 may detect a CMD 25 through conduction of an electrostatic charge by the user holding the mobile device and touching the steering wheel, or similar part of the vehicle in the driver's seat, thereby creating an electrostatic connection leading to the deduction that the driver user is holding the mobile device within the restricted zone.

Figure 5:
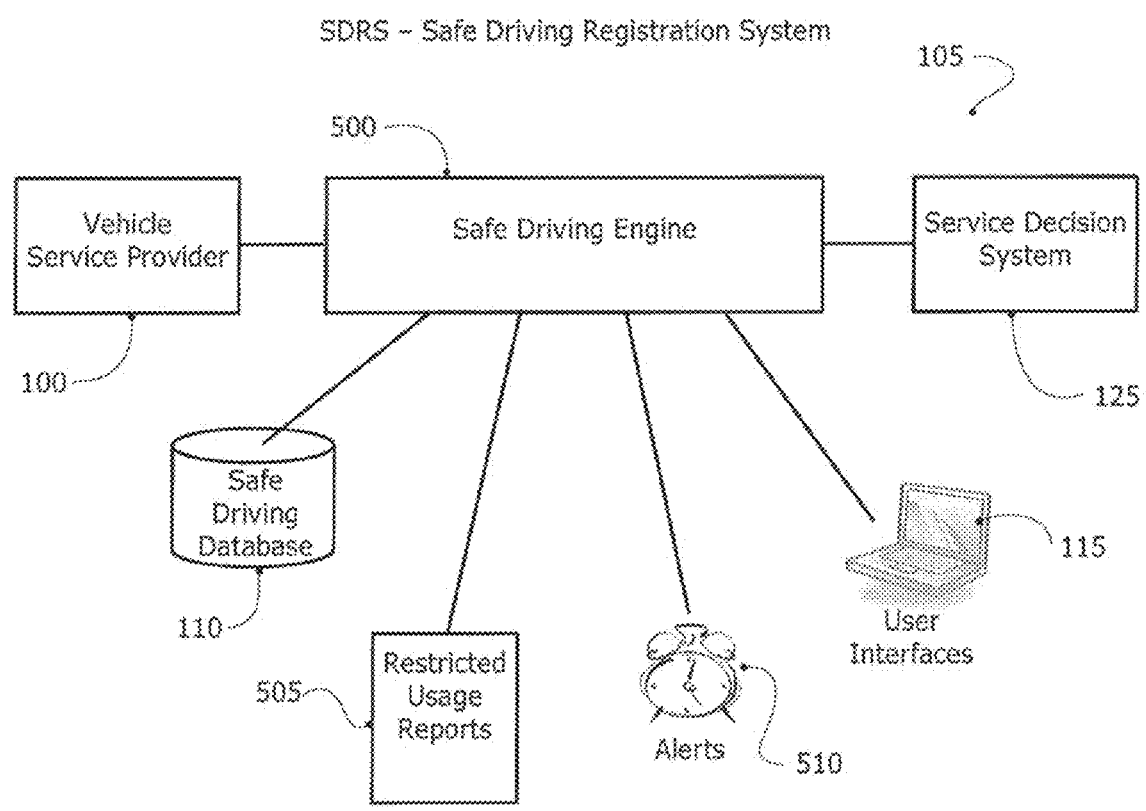
FIG. 5 discloses an illustrative functional block diagram of the Safe Driving Registration System (SDRS).

Disclosed in FIG. 5 is one embodiment of the functional components that may be provided in the Safe Driving Registration System (SDRS) 105. The SDRS 105 includes a safe driving engine 500 (e.g., a hardware/software configuration of computational equipment) which receives the vehicle plus mobile detected information about the vehicle 15 and possibly Controllable Mobile Device (CMD) 25 position information from the Vehicle Detection System (VDS) 30 via the Vehicle Service Provider (VSP) 100. The safe driving engine 500 stores the received information, along with information identifying the registered vehicle 15, the registered CMDs 25, and the subscriber, in the Safe Driving Database 110. Further, the safe driving engine 500 provides user interfaces 115 for subscribers, system administrators, and possibly data subscribers to access data stored in the Safe Driving Database 110, configure preference and service control settings, configure alert message options 510, configure game settings, awards, tokens, discounts, and to generate reports 505. The user interfaces 115 provided by the safe driving engine 500 may be accessed by computational devices, such as, for example, a personal computer, a personal digital assistant (PDA), a smart phone, a mobile phone, or other similar device equipped with an Internet connection, which may also provide an Internet web browser.

The safe driving engine 500 is also operational to transmit information from the Safe Driving Database 110 to the Mobile Device Service Provider (MDSP) 130 via the Vehicle Service Provider (VSP) 100 through various land based and wireless based communication networks and/or to receive information from the MDSP 130 which may include, for example, usage data for specific mobile services. With mobile usage data, the safe driving engine 500 may correlate that data with vehicle operational data and, possibly CMD 25 restricted zone position data, and/or perform other calculations on the data.

Disclosed in FIG. 6 is one embodiment of the functional components that may be provided in a Service Decision System 125. The Service Decision System 125 may include a service decision engine 600 (e.g., a hardware/software configuration of computational equipment) which receives vehicle plus mobile detected information. In one embodiment, the service decision engine is in direct communication with the Mobile Device Service Provider (MDSP) 130 (shown in FIG. 1) wherein the MDSP 130 is allowed to access the Safe Driving Registration System (SDRS) 105 and either queries the SDRS for update vehicle operational use and restricted zone data from the centralized Safe Driving Database, or the MDSP registers with the SDRS for regular and periodic updates (e.g., every minute, or every few seconds, a real-time stream, or some such appropriate interval) of the data to be sent by the SDRS. Alternately, or in addition to, the Service Decision System 125, via the MDSP 130, may receive the data to be stored and forwarded in some other timing arrangement.

Alternately and/or optionally, the Service Decision System 125 may be in direct communication 120 with the Safe Driving Registration System (SDRS) 105 to receive the vehicle plus mobile detected information.

The service decision engine 600 may also be operational to receive input service control settings 605 which may include, but are not limited to, parameters defined by state or local laws, parameters set by the Mobile Device Service Provider (MDSP) 130, parameters set by individual subscribers for all users of CMDs 25 for the subscriber, parameters of a game, or awards, or discounts and/or individual users within a group managed by the subscriber. The service control settings 605 may include, but are not limited to, parameters that define which service the service decision engine 600 controls for which users (e.g., voice calls, text messaging, video calls or messaging, Internet access, games, etc.); how those services are controlled (e.g., disable the service when the vehicle is operational, disable the service when the Controllable Mobile Device (CMD) 25 is within the restricted zone, enable the service when the CMD moves outside of the restricted zone, enable the service when the CMD is within the restricted zone but send a warning or reminder message to the CMD, as well as other possible control scenarios); what time frames some services may be enabled or disabled, as well as other control preferences.

Further, the service control settings 605 may be stored and managed in operations with the service decision engine of the Service Decision System 125, or in direct operation with the SDRS 105.

Figure 7:
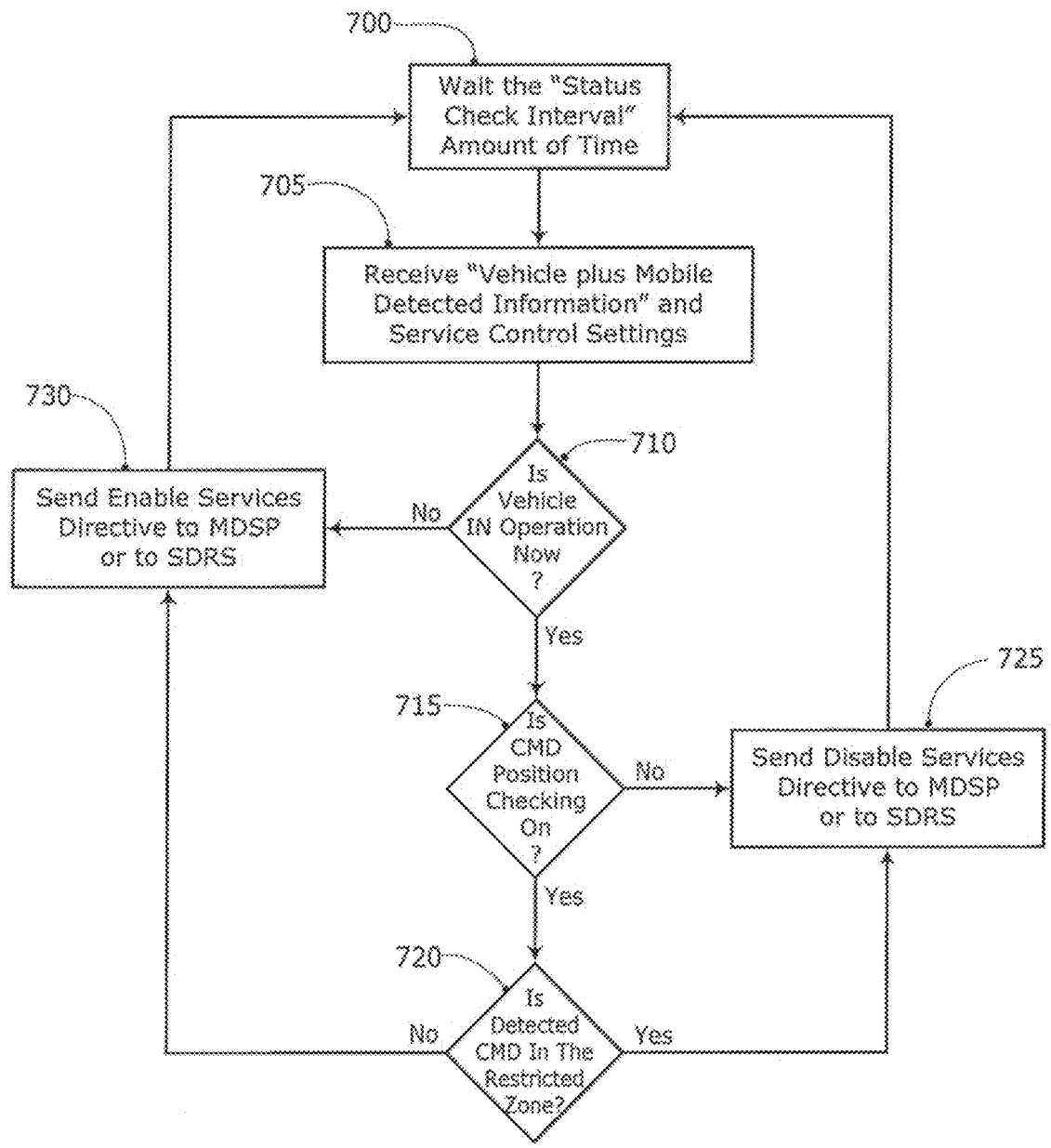
FIG. 7 discloses a flowchart for the Service Decision Engine logic.

Disclosed in FIG. 7 is a flowchart illustrating some of the steps in the service decision engine 600 to determine whether to enable or disable services. The service decision engine 600 may receive vehicle plus mobile detected information and service control settings (step 705). If the vehicle 15 is not in operation (as determined in step 710) the service decision engine 600 sends an enable services directive to either the MDSP 130 or the SDRS 110, depending on how it is configured (disclosed in FIG. 1). Conversely, if the vehicle is in operation (as determined in step 710) and the option to check for CMD 25 positioning relative to the restricted zone (step 715) is off, then the service decision engine 600 sends a disable services directive (step 725) to either the MDSP 130 or the SDRS 110. Alternately, if the vehicle 15 is in operation (as determined in step 710), the option to check for CMD positioning is on (step 715), and the CMD 25 is within the restricted zone of the vehicle (as determined in step 720), then the service decision engine 600 sends a disable services directive in step 725, or if the CMD is outside the restricted zone, then the service decision engine 600 sends an enable services directive in step 730. Regardless, after the service decision engine 600 sends the appropriate enable/disable service directive, it waits a configured amount of time in step 700 (e.g., a minute or two, or perhaps even seconds) before repeating the process and receiving updated vehicle plus mobile detected information in step 705. The service directive may specify individual services, may direct all services (except emergency response services), may direct disabling the battery on the CMD (which in turn, would prevent operation of the CMD), may directly disable all functions on the CMD, or may send a warning message to the user of the CMD and/or to the subscriber.

In one embodiment, the service directive is transmitted in a real-time or near-continuous stream to the MDSP 130 or SDRS 105, or alternately could be stored and forwarded in some other timing arrangement.

Alternately, the Service Decision System 125 and service decision engine 600 may be provided in any other suitable component of the mobile service control system 10, including, but not limited to, the mobile device control software 225 of the CMD 25 (as illustrated in FIG. 2).

Figure 8:
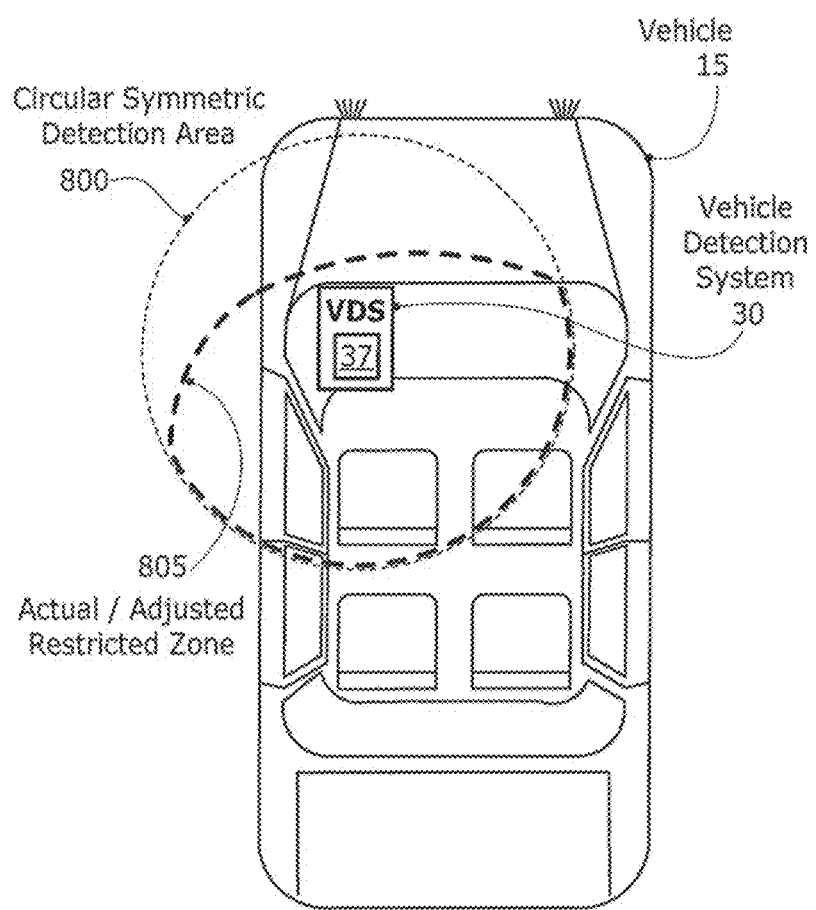
FIG. 8 discloses an illustrative layout of a single position detector in a vehicle.

FIG. 8 shows one embodiment of the Vehicle Detection System (VDS) 30 with position detection capabilities in a passenger vehicle 15. A single position detector 37 is shown along with the circular symmetric detection area 800. In practice, however, the perimeter of the detection coverage area may be irregular and influenced by the dashboard, driver's door, the seats, and materials used in and around the driver's seat of the vehicle. In a single position detector 37 configuration, the restricted zone 805 for detecting an Controllable Mobile Device (CMD) 25 is the same as the actual perimeter of the circular symmetric detection area. Further, the VDS 30 may provide the ability to adjust the extent of the restricted zone 805 by adjusting the power level of the position detector 37, such as, for example, adjusting the RFID reader. For example, in some deployments the restricted zone may only extend to the edge of the driver's seat, whereas in others it may extend to the middle of the front passenger's seat and behind the driver's seat as illustrated in FIG. 8.

Figure 9:
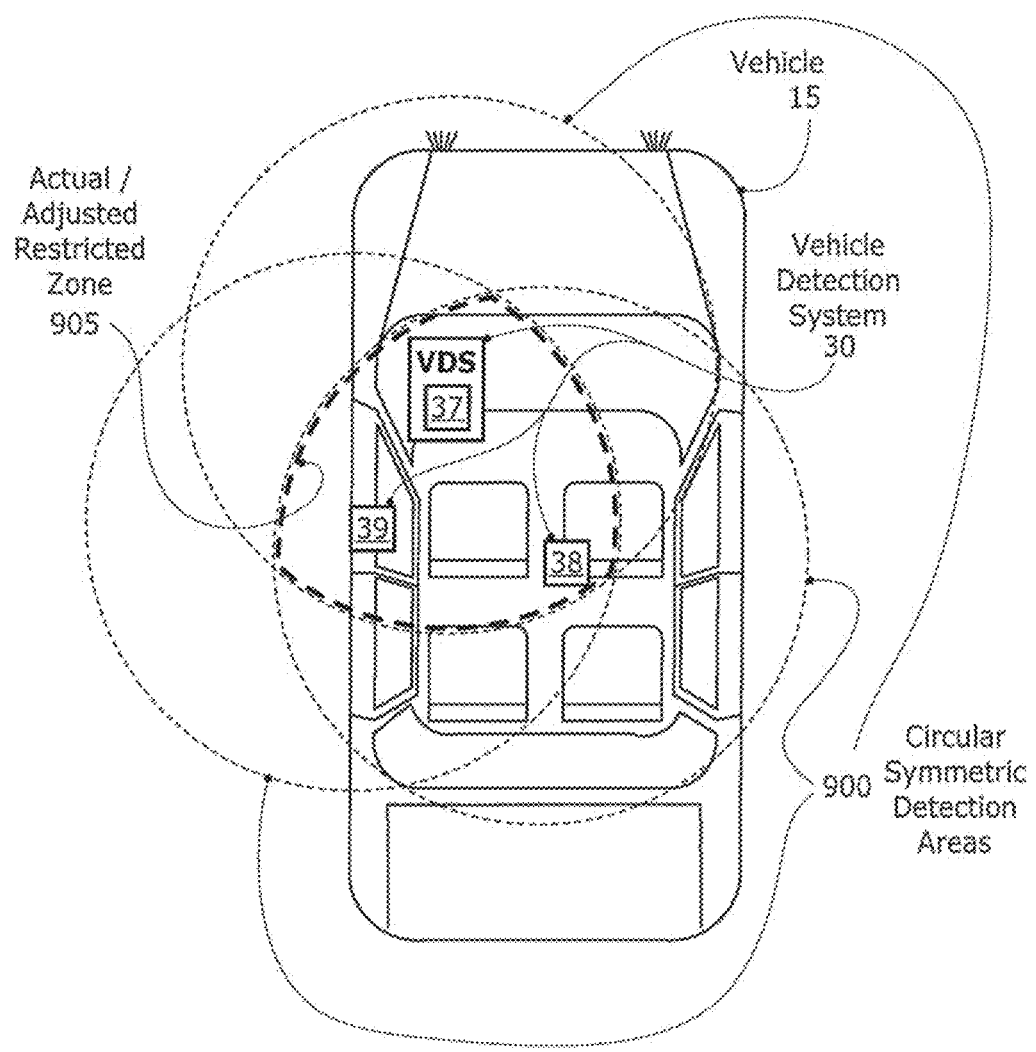
FIG. 9 discloses an illustrative layout of multiple position detectors in a vehicle.

Disclosed in FIG. 9 is one embodiment of the Vehicle Detection System (VDS) 30 in a passenger vehicle 15 with three position detectors and/or sensors 37, 38, 39 with their unconstrained circular symmetric detection areas 900. In this type of configuration the three detectors and/or sensors 37, 38, 39 can be used to triangulate an accurate position of the Controllable Mobile Device (CMD) 25. The overlap of the coverage areas from the three position detectors and/or sensors 37, 38, 39 defines the restricted zone 905, which is illustrated with a darker dashed line.

Referring again to FIG. 1, the mobile services control system 10 disclosed herein, including, but not limited to, the Vehicle Detection System (VDS) 30, the Vehicle Service Provider (VSP) 100, the Safe Driving Registration System (SDRS) 105, the Safe Driving Database 110, the Mobile Device Service Provider (MDSP) 130, the Service Decision System 125, and the Controllable Mobile Device (CMD) 25, are all operational to allow emergency, or other designated priority communications, including voice calls, video calls, text messages, emails, or other similar communications, at all times even when the system has determined that one or more services should be disabled due to vehicle operational status or the position of a CMD within a restricted zone of a vehicle.

Disclosed herein is another embodiment of the mobile services control system 10 that is well suited for vehicles 15 that are primarily operated by a single driver-operator, or driven or operated by multiple driver-operators who are scheduled so that at any particular time, the driver-operator of a corresponding vehicle 15 is known with high confidence (e.g., commercial drivers of vehicles such as trucks and taxi cabs, operators of public transportation such as buses or trains, and drivers of government vehicles). Since such a driver-operator of a vehicle 15 is often the primary user of a unique CMD 25 or unique CMDs, knowledge of the motion of the vehicle 15 in conjunction with knowledge of the operator of that vehicle (perhaps at a specific time) in conjunction with knowledge of a unique identifier of the operator's CMD 25 (such as a cell phone number of the CMD(s), or Mobile Device Air Identifier of the CMD(s)), enables the Mobile Services Control System 10 to provide notifications to appropriate wireless carrier network equipment for activating and/or deactivating CMD services (e.g., texting, etc.). In particular, such activation and/or deactivation may be substantially solely dependent upon a determination of whether the vehicle 15 is moving. In this embodiment, the Safe Driving Registration System 105 (FIG. 1) is configured through one or more of the User Interfaces 115 (by a person and/or an automated input) with information specific to a unique vehicle 15 having with a Vehicle Detection System (VDS) 30, or information specific to a plurality of vehicles 15 each having a Vehicle Detection System (VDS's) 30, wherein the information includes: (i) at least one primary operator of vehicle 15, or if multiple operators are scheduled for the vehicle, information specifying the times that a specific one of the operators will be operating the vehicle 15. Additionally, the Safe Driving Registration System 105 is provided (e.g., via a User Interface 115) with CMD information identifying which CMD 25 or CMDs 25 are associated with each of the operator(s), as well as information as to what incoming and outgoing calls, text messages or other information should be allowed for emergency use or otherwise while services to such CMD(s) are being controlled by the mobile services control system 10. Note that in this embodiment, vehicle 15 incorporates a Vehicle Detection System (VDS) 30 that may or may not incorporate a Detection Engine 300 since the requirement you detect the location or position of an operator's CMD 25 within the vehicle occupant enclosure 20 may not be necessary.

Figure 10:
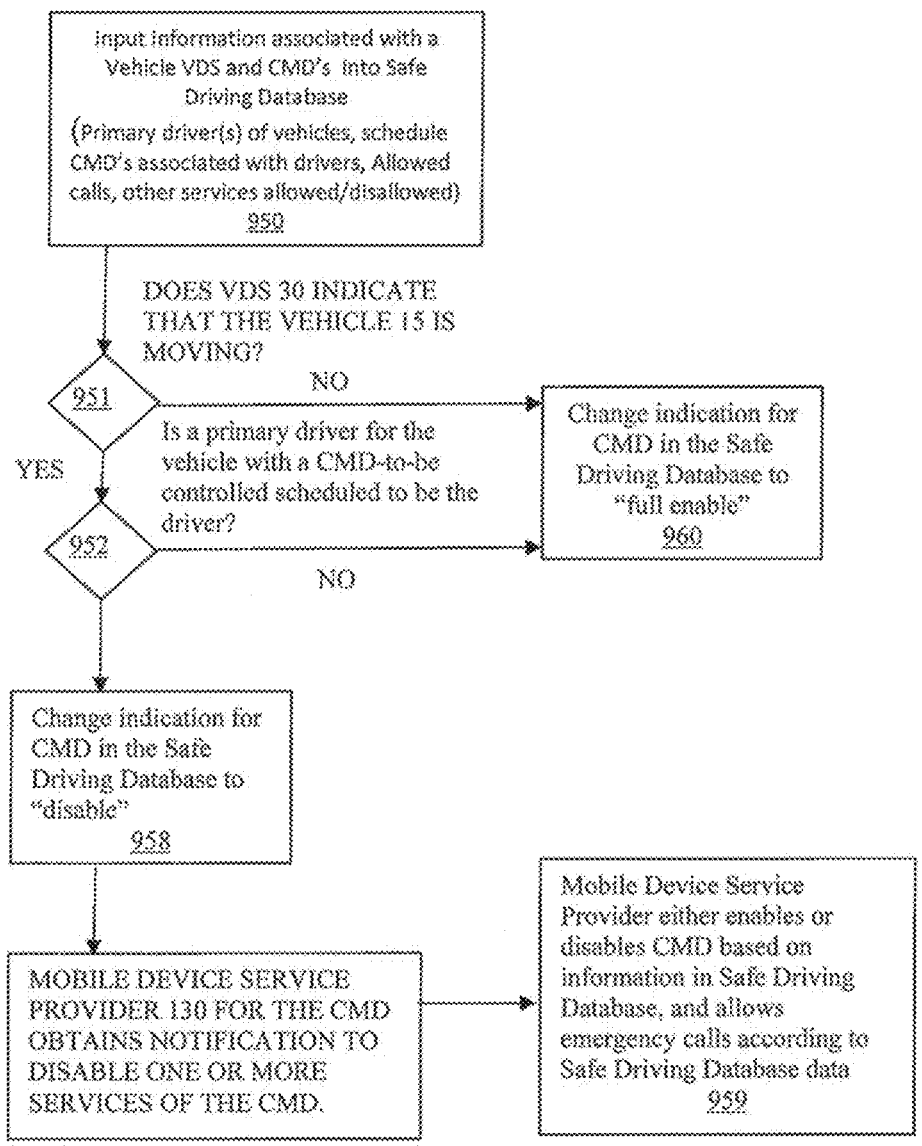
FIG. 10 discloses a flowchart of a simplified embodiment of the processing performed by the mobile services control system 10.

Referencing FIG. 1 and the flowchart in FIG. 10, in step 950, a user (e.g., subscriber) provides input for configuring the Safe Driving Registration System 105 with the identification of the driver-operator(s) associated with each particular vehicle 15 (or VDS 30 therein), the identification(s) of each such vehicle (or VDS 30 therein), as well as (if known) the times that each such driver-operator is scheduled to operate a corresponding vehicle 15. Additionally, identifiers for the each of the CMDs 25 (e.g., cell phone numbers and wireless carrier provisioning the CMD) that is used by each of the driver-operators and that are desired to be controlled 950 are also input to the Safe Driving Registration System 105. For each of the VDSs 30 (which in the present embodiment need not include the detection engine 300, nor any of the position detectors), in step 951, the VDS monitors the condition of its vehicle 15 (for instance whether the vehicle is moving or not through methods described elsewhere in this specification), and intermittently communicates the condition of the vehicle through wireless connection 65 to base station 70 and wireless network 60 to Vehicle Service Provider 100, and thereby to the Safe Driving Registration System 105 and Safe Driving Database 110. The intermittent connection between the VDS 30 and the VSP 100 may be specified so that a very limited amount of information is transmitted infrequently (every minute or several minutes), so that even though the VDS reports the condition of the vehicle, the power requirements of the VDS are minimal, potentially enabling a solar-powered or battery powered VDS that does not require connection to vehicle 15 power. When, through this connection, the VDS 30 indicates to the Safe Driving Registration System 105, that the vehicle 15 is not moving, then in step 960, the Service Decision System 125 indicates within the Safe Driving Database 110 that an associated CMD 25 (for a potential operator of the vehicle) does not require disabling by the Mobile Device Service Provider 130. However, when the VDS 30 indicates vehicle motion through this connection, then in step 952, the Service Decision System 125 utilizes the information associated with that vehicle 15 that is within the Safe Driving Registration System 105 and Safe Driving Database 110, to determine if a particular one or more CMDs 25 associated with this vehicle should have one or more services disabled. If the CDMs 25 are to be disabled, then in step 958 data indicative of such disablement is stored in the Safe Driving Database 110. Then in step 970, the mobile device service provider 130 for the CMD 25 obtains (via notification or polling) to disable services for the CMD. In step 959, the information within the Safe Driving Database, including information regarding allowable emergency numbers for a specific CMD, is made available to the Mobile Device Service Provider (MDSP) through the Internet, or other wired or wireless services to indicate that the MDSP should disable the CMD associated with vehicle 15. Alternately, in step 959, the information contained in the Safe Driving Database regarding a particular CMD and the associated vehicle may be transmitted via the Internet or other wired or wireless services directly to the MDSP directing the MDSP to disable the CMD associated with vehicle 15. Optionally, as an alternative step to step 952, the system 10 may utilize information derived from comparing the relative strength of signals received by Wireless Base Station 55 and Wireless Base Station 70, and the locations of Wireless Base Station 55 and Wireless Base Station 70 to determine if the CMD 25 is proximal to VDS 30 of a specified vehicle 15, and therefore determine whether the CMD should be disabled or whether that CMD 25 is distant from the VDS 30 of the specified vehicle 15, and therefore even if vehicle 15 is moving, this CMC should not be disabled. Optionally, as an alternative step to step 952, the system 10 may incorporate a detection engine 300, through techniques described elsewhere in this specification to determine if a particular CMD associated with vehicle 15 is within vehicle 15 and therefore should be disabled. It is possible that the system 10 described in this embodiment disables a CMD that is not within the associated vehicle 15. In this instance, the system 10 may allow such disablement of services to be overridden through a variety of methods that may include input by an administrator or subscriber of the control services offered by the system 10 for a CMD account authorizing an override of the disabled CMD. Alternatively/optionally, the system 10 may allow the transmittal of a text or voice message by the CMD to a telephone number associated with the system 10 that can authorize an override for the CMD (CMD User Override). Optionally, if the CMD sends a text or voice message that authorizes an override of the disabled CMD, the system 10 may send a text, email or voice message to the administrator or subscriber of the CMD account indicating that a CMD User Override has been executed as well as information as to the condition of vehicle 15 associated with the CMD at the time of the CMD User Override, so as to provide information to the administrator or subscriber of the account. Note that such overrides may be logged for identifying abuse of the CMD User Override. In the event of CMD User Override abuse, the administrator or subscriber of the CMD account can disable the CMD User Override for a specific CMD via user interface 115.

Figure 11A:
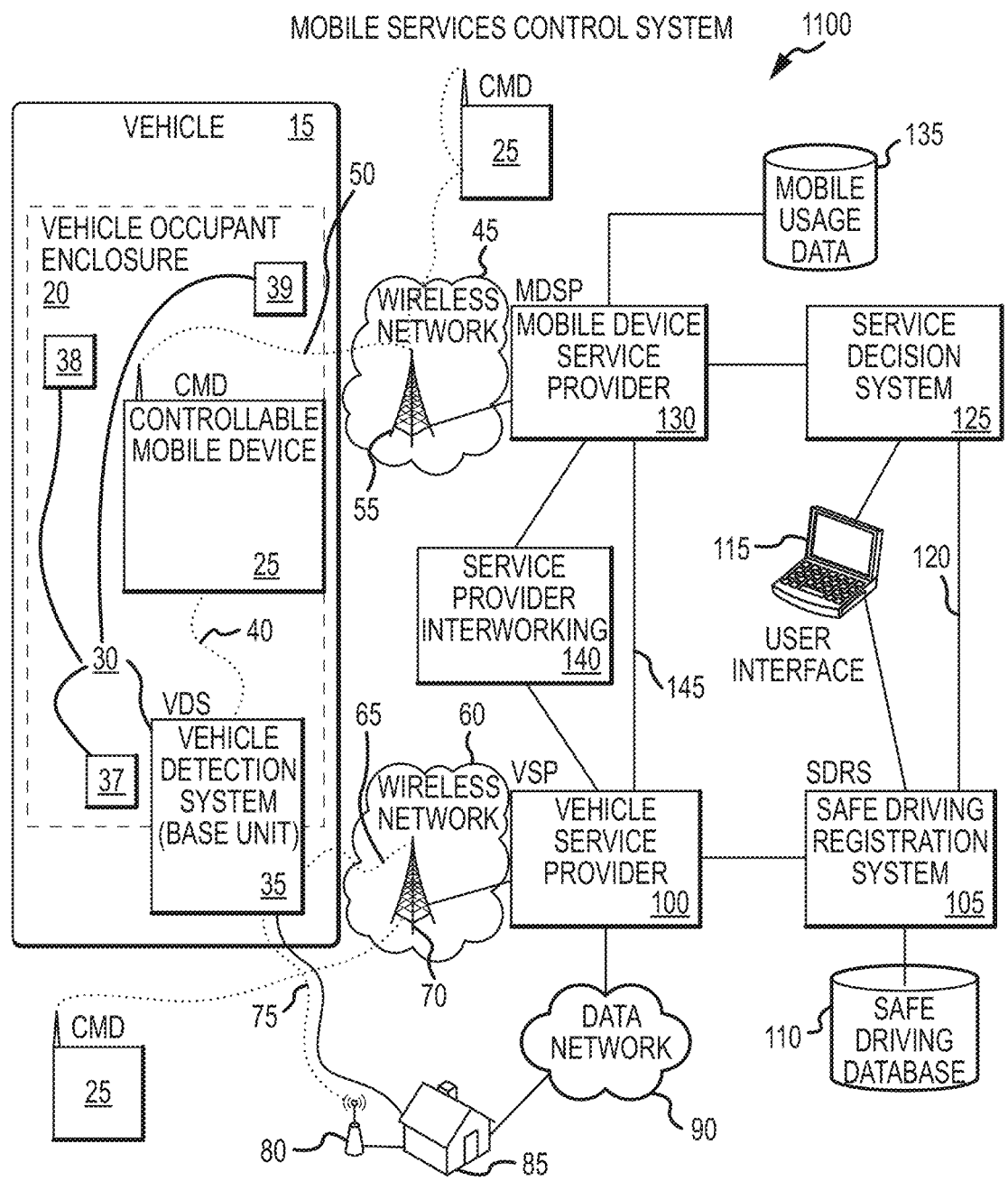
FIG. 11A discloses a system diagram of an illustrative embodiment for a system for controlling mobile devices.

FIG. 11A discloses a system diagram of an illustrative embodiment for a system for controlling mobile devices.

Referring to FIG. 11A, the system 1100 components are described in detail with reference to FIG. 1. The system includes SDS 125 is configured to use a variety of different inputs from at least one of a CMD 25, VDS 35, and/or Vehicle 15 in this embodiment. At least one CMD 25 may be associated or registered with the VDS 35 in that the CMD is registered as being used by a potential driver(s) of vehicle 15 associated with VDS 35, optionally including additional information about the potential driver(s). As with any embodiment of the invention a CMD may be associated or registered with a VDS 35 such that it is a registered controllable mobile device, such registration simplifying the process of determining if CMDs are in vehicle 15 or in use by a driver by limiting the number of CMDs that are likely to be in the vehicle when it is in an unsafe state such as when moving. The term registered and associated are used interchangeably throughout. Alternatively, for some embodiments it is not necessary that the CMD be registered with VDS 35.

In a preferred embodiment, only a single CMD is associated or registered to a VDS. Alternatively or optionally, more than one CMD may be associated or registered with a VDS or vehicles. Moreover, the association of a CMD may change over time according to a predetermined schedule. For example, on a Monday a first CMD may be associated with a VDS or vehicle, on Tuesday a second CMD (adding or deleting the association of the first CMD) may be associated with the same VDS or vehicle, and so on. In addition, more than one CMD may be associated with a VDS or vehicle for a business. Also, every CMD in a particular area may be associated with a VDS or vehicle as needed. Also, every CMD associated with a specific MDSP may be associated with a specific VDS, or multiple VDSs.

In one embodiment, SDS 125 is configured to use one or a combination of location, location error, velocity direction of travel, the location of cell towers connected to a particular CMD 25 or VDS 35 and time since start of trip to determine the probability of a CMD 25 being in a vehicle. This data may be obtained from the CMD 25, VDS 35, and/or Vehicle 15 by either an electronic query from the SDS 125 (pull) or by data provided to the SDS 125 without query as part of the operation (push), or by other techniques known in the art. Electronic query means communication between two components (hardware, software and/or combinations), e.g., including but not limited to any connection between devices such as over a wireless network, wired network, or other communication mechanism.

In one embodiment, the location of CMDs 25 that have been previously been identified as possibly being used by a driver of a particular vehicle containing a VDS 35, e.g., a registered CMD associated to a specific driver, can be combined with the location of the VDS 35 in the Vehicle 15, and the estimated or calculated errors in each of the location measurements, and other data as such listed above to establish which of the CMDs are likely within the vehicle, and therefore could potentially distract the driver of the vehicle.

Moreover, in one embodiment the SDS 125 is operable to send a signal to MDSP 130, to the CMD 25 via the MDSP 130, or to third party providers that can control functionality of the CMD 25 The MDSP 130 is operable to send a disable signal to a predetermined CMD 25 or to disable or partially disable operation of a predetermined CMD 25. By way of definition, the term disable and partially disable shall be used interchangeable throughout the application, and shall mean to completely or partially limit the functionality of a CMD. The term disable signal shall mean a signal that provides notification that a CMD should be partially or fully disabled as used throughout the document. The disable signal can be emitted from any component or module of the system as described herein. Third party providers are operable to provide a disable signal to the CMD 25 or to disable or partially disable operation of a predetermined CMD 25 on receiving a disable signal from the SDS. The CMD 25 may be operable to disable or partially disable potentially distracting functions on receiving a disable signal from the SDS 125, MDSP or third party provider.

In another embodiment, when the CMD may possibly not be operable to be disabled or for other reasons may be desired to not be disabled, the disable signal for a specific CMD shall be recorded in the SDD along with the time it was sent, the identity of the CMD and the identity of the associated VDS, and other related information to allow a comparison with usage records for that CMD, provided by the MDSP, or another third party provider of services to the CMD, so as to provide a record of when the CMD was used while the vehicle was in a potentially unsafe state, and optionally to provide alerts of potentially unsafe CMD use. In embodiments of the invention, upon an enabling event or disabling event such as sending a disable signal or disabling a CMD, the following information is optionally simultaneously recorded in the SDD including at least the time of disable signal, identities of VDSs, CMDs and drivers, and other information related to the event.

In operation, various information, e.g., velocity, location, location error, direction of travel of the vehicle can be obtained directly from the VDS 35 using techniques such as vehicle GPS data, and velocity data from a GPS chip integral to the VDS 35. This information may also be obtained through sensing change in velocity from an accelerometer imbedded on the VDS 35, accelerometers in the vehicle, from vehicle information (such as speed) provided to the VDS through various means, or from velocity information provided by CMDs known to be within the vehicle, e.g., by GPS data or accelerometer data provided by the CMD 35 within the vehicle. Optionally, the VDS 35 may be connected to an OBDII port or other port in the vehicle to provide data from vehicle sensors.

Figure 11B:
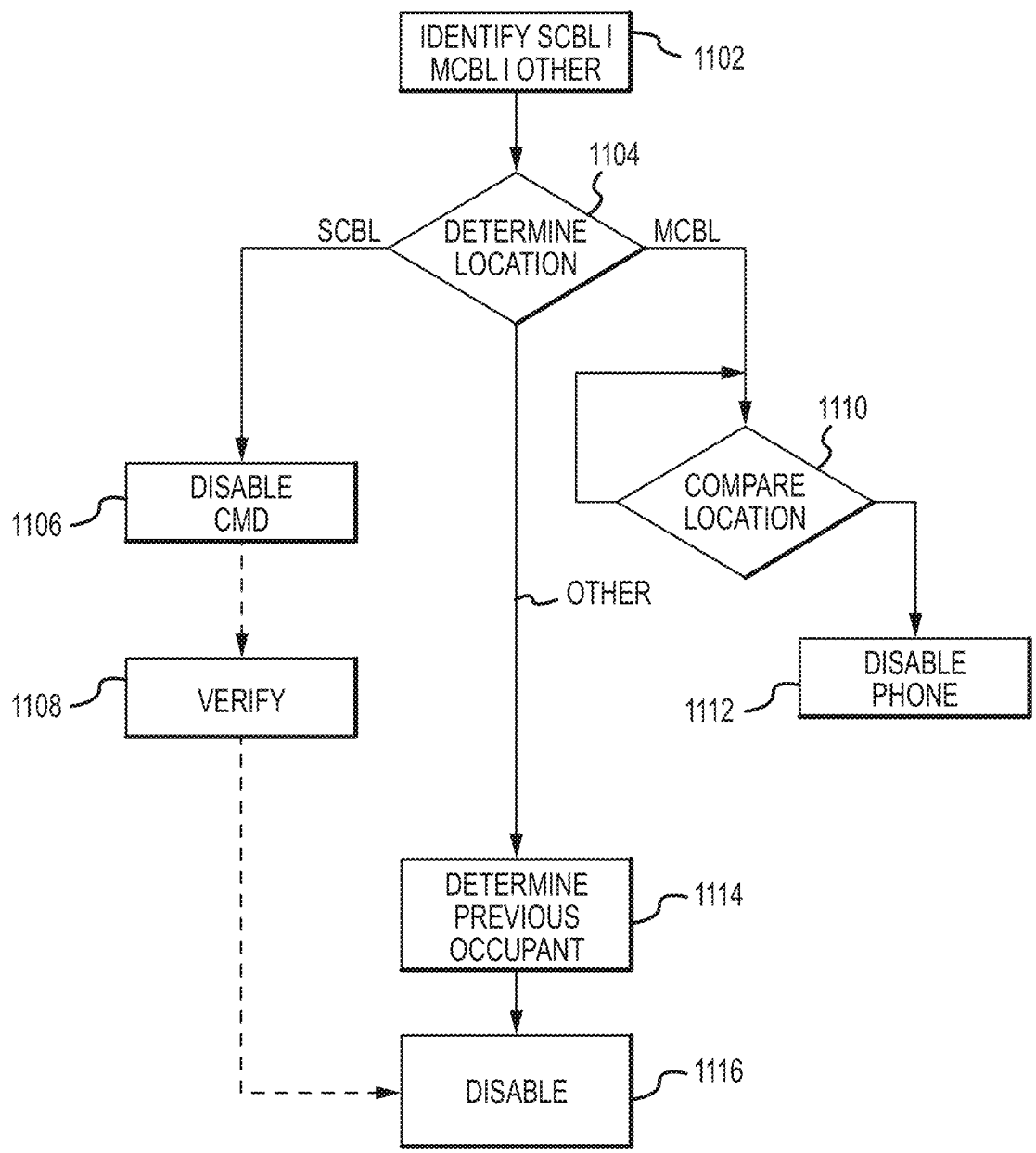
FIG. 11B discloses a flowchart of a simplified embodiment of a technique performed by the mobile services control system to determine if a CMD is in a vehicle with a VDS.

FIG. 11B discloses a flowchart of a simplified embodiment of a technique performed by the mobile services control system to determine if a CMD is in a vehicle with a VDS.

Referring now to FIG. 11B, beginning of trip location information, e.g., information associated with start of a trip in which a CMD may potentially be distracting, is utilized to simplify and enhance determinations of whether CMDs are located within a vehicle or a CMD is associated with a driver of a vehicle. Generally, the locations can be divided into three categories including Multiple CMD Base Location (MCBL) information, Single CMD Base Location (SCBL) information and location information that is neither MCBL information nor SCBL information.

MCBL information is a predetermined geographic location such as a home or place of business, where multiple drivers share a vehicle and therefore a given vehicle associated with a VDS, may have any one or more drivers with registered CMDs associated with the VDS be within the vehicle or driving the vehicle on trip start. In this case the SDS is operable to discriminate which registered CMDs are in the vehicle from those not in the vehicle but potentially proximal to the MCBL A VDS is associated or registered with one or more MCBLs, so that any given car at one of these locations may have one of a finite number of possible drivers.

SCBL information is a predetermined geographic location such as a home, place of business, school, or shopping center, or similar location where it is probable that only one driver associated with one or more CMDs is driving a vehicle associated with a VDS on trip start. The VDS is associated or registered with one or more SCBL, so that the driver of the vehicle can be quickly identified.

MCBL and/or SCBL information may be assigned via a User Interface 115 by a user or third party. The MCBL and/or SCBL such information includes user information, VDS identities associated with the location, associated driver identities, associated CMD identities, physical addresses or GPS locations associated with a list of places, e.g., home, business, gym, shopping, schools, resorts, other locations of interest and optionally additional information may also be associated to the MCBL and/or SCBL information including but not limited to the probability that specific drivers may be driving the vehicle when starting from that location. In a preferred embodiment, MCBL and/or SCBL information is stored in the SDD 110.

Moreover, the SCBL or MCBL information may be acquired automatically by system 1100. The determination of SCBLs and MCBLs associated with a given VDS and CMDs can be inferred over time from previous trips, by establishing which CMDs are in the vehicle at a particular location on trip start by other means described herein. When the probability of a particular CMD being within a vehicle on trip start from a specific location, or is determined to be above a predetermined threshold, the associated location can be identified as an SCBL or MCBL for that VDS and CMD(s). In the instance when only a single CMD is likely to be within the vehicle from that trip start location it can be defined as a SCBL. Alternately, the location may be defined as an MCBL for a given VDS and a group of CMDs, when there is a likelihood that there are one of several drivers within the vehicle at trip start. The location information is added to the SDD 110 and associated with the particular MCBL and/or SCBL information.

Referring again to FIG. 11B, on trip start, an identification of whether an SCBL or MCBL is associated with a VDS is performed (Step 1102). This identification may be conducted by a SDS 125 query of SDD 110 for associated or registered SCBLs and/or MCBLs to a particular VDS.

After determining whether the VDS is associated with a SCBL, MCBL or neither, the geographic location of the VDS is acquired (Step 1104). The geographic location of the VDS may be determined by deriving information from the carrier network related to the VDS 35, such as the location of the cell tower 55, 70 that the VDS 35 is connected to, triangulation of cell tower signals that the VDS 35 is connected to, location information provided wirelessly from a GPS device within the VDS 35, time of flight methods of determining location from the VDS signal, various techniques used for e911 emergency location of a mobile device, information captured on the VDS 35 with respect to cell tower connection information and relative signal strength from various cell towers, and assisted GPS (aGPS) enabled on the VDS 35, other technique described herein throughout, or other techniques as known in the art. In a preferred embodiment, the geographic location of the VDS is determined by accessing the last location of the VDS stored in the SDD 110.

After the location of the VDS has been determined go to step 1106 if the desired VDS is associated with a SCBL. Step 1106 requires the system to disable the CMD associated or registered with SCBL information. The disabling of the CMD may be conducted as described herein. Optionally, a verification step 1108 may be performed.

The verification step 1108 includes determining the location of the disabled CMD, and optionally other CMDs associated with the VDS, and comparing it with the location of the VDS. This location of CMDs may be obtained from a pull query or push query of the CMD via the system 1100 or with other techniques described herein. Typically, this is a low cost method, such as using cell tower information, or information provided by a GPS-equipped CMD, either through push or pull techniques. Alternatively or optionally, the location of the CMD may be obtained with high cost location method, e.g., directly from a network, data provider, third party as a charged service.

The VDS location and CMD location are compared to establish if the distance between them is within the predetermined threshold error distance (PTED. The PTED is related to the accuracy of the location information, and is typically less than 200 meters for GPS data, is typically less than 3000 meters for cell tower location techniques in rural areas with large distances between cell towers, and may be less than 500 meters in urban areas with small distances between cell towers. Of course this PTED can change depending on the accuracy of the CMD location and/or VDS location. The more accurate the CMD location and/or VDS location the shorter the PTED can be set. That is, if the accuracy from both the CMD and VDS are within 5 meters or less, then a 10 meter PTED can be used. Alternately, as the accuracy of CMD location and/or VDS location lessens, the greater the PTED.

The verification step 1108 is a double check that is optionally performed to confirm that the disabled CMD is within a vehicle and other associated CMDs are not. If the locations of the CMD and the VDS when compared indicate a distance less than the PTED threshold step 1106 the CMD remains disabled and other CMDs identified to be within the vehicle are disabled, if the location of any associated CMDs and the VDS when compared are greater than the PTED then the CMD can be enabled (while other previously disabled CMDs remain disabled). Alternately a disable signal can be sent when the distance between the CMD and VDS are such that when accuracies in location measurement are considered and optionally combined with other information described herein, there is a high probability that the CMD is within the vehicle although the location information alone does not confirm the CMD is in the vehicle.

Optionally, after step 1102, previous trip information is provided by SDD 110 on a query from SDS 125, including the identify of CMDs within the vehicle at the end of the previous trip associated with the VDS, (as also described in step 1114 below). If this information indicates that a single registered CMD is different than that typically associated with the SCDL was in the vehicle, then it is probable that the CMD in the vehicle on the previous trip is within the vehicle at the start of trip, and therefore step 1106 is performed with the CMD identified from the previous trip, rather than with the CMD associated with the SCBL. Similarly if multiple associated CMDs are identified as having been in the vehicle on the previous trip, the trip is treated as starting from a MCBL (as described in step 1110 below) with the CMDs associated with the start of trip location as if the location was a MCBL, being those identified as being within the vehicle on trip end.

If the desired VDS is associated with MCBL information, go to step 1110. Step 1110 requires the system 1100 to obtain the location of each of the multiple CMDs associated with the MCBL and VDS. The location of each of these CMDs may be obtained from a pull or push query of the CMD as described herein. Typically, this is high accuracy method. Alternatively or optionally a low accuracy location may be obtained from cell tower information or other low accuracy, low cost means, or other means can be used to determine if a registered CMD is in the vehicle our outside of the vehicle.

The location of each CMD is compared to the starting location of step 1104 and the VDS location. The location of the CMDs and VDS associated with that MCBL are determined by means described herein. If the error in the CMD and VDS location measurement allows discrimination of CMDs in the vehicle from those remaining at the MCBL, then the SDS proceeds to step 1112. Alternately the SDS can utilize a Predetermined Threshold Distance (PTD), which is a threshold distance between a VMD and a base station that given typical CMD and VMD location accuracies has a high probability of enabling discrimination of CMDs remaining at the base from those in a vehicle. The PTD is typically greater than 100 meters with GPS-based location measurements. Of course this PTD can change depending on the accuracy of the CMD location and/or VDS location. The more accurate the CMD location and/or VDS location the shorter the PTD can be set. That is, if the accuracy from both the CMD location and/or VDS location is 5 meters or less than a 10 meter predetermined threshold distance can be used. Alternately, as the accuracy of CMD location and/or VDS location worsens, the PT can be set to greater values to take in account the increased likely error of location. By way of example, the PTD may be greater than 500 m in urban areas with a high cell tower concentration when a non-GPS cell tower-based location is used, and greater than 3000 m in rural areas of low cell tower concentration when cell tower-based location is used.

If the CMD and VDS location error is so large as to not allow discrimination between CMDs located at the MCBL from CMDs in the vehicle, then the SDS waits a predetermined amount of time and step 1110 is repeated and the location of the CMDs and the VDS again compared. This step can be repeated until there is sufficient distance between the VDS and the MCBL to discriminate associated VMDs in the vehicle.

Alternately, the SDS may wait a predetermined time after trip start to determine location of the CMDs and VDS, so as to allow sufficient time for there to be adequate distance between the VDS and the MCBL to discriminate the location of CMDs in our out of the vehicle. The predetermined amount of time may be in a range from less than 15 seconds to five minutes or greater. This time may be set by the user interface 115 as a criteria in the MCBL information and stored in the SDD 110, or be a default amount. Once there is sufficient distance between the VDS and MCBL, the CMDs within the vehicle, as described herein, are disabled (Step 1112).

If the desired VDS is not associated with either a SCBL or MCBL go to step 1114. On trip start, the SDS queries the SDD for the most recent location of the CMDs registered to the VDS. The CMDs that were determined to be within the vehicle in the previous trip, are considered to be potentially within the vehicle for the current trip. CMDs that were not in the vehicle at the end of the previous trip are assumed to not be in the vehicle. Similarly, any registered CMDs that were in the vehicle during the previous trip, but whose last known location is such that they could not be in the vehicle at the beginning of the trip, are considered to not be in the vehicle (for instance, a registered CMD that had a location 30 miles from the VDS 15 minutes prior to the start of trip, would be considered to not be in the vehicle, as it would have to have traveled at 120 mph to be in the vehicle). Next, the CMD or CMDs that are considered to be in the vehicle are disabled. (Step 1116). Optionally, a verify step 1108 may be performed as previously described herein.

In one embodiment, the SDS is operable to receive information as to the identification and location of the cell tower that a given registered CMD is connected to, and thereby determine when the CMD switches its connection from one tower to another, thereby indicating that CMD is in motion providing additional information that allows the SDS to determine there is an increased probability the CMD is in a vehicle if the associated VDS is has also been determined to be in motion, increasing the ability of the SDS to quickly discriminate CMDs within our separate from the vehicle. Alternately, as the SDS receives information that the CMD has not switched to a different cell tower although the associated VDS is in motion for a period of time, the SDS can determine that it is less probable that the CMD is in the vehicle, increasing the performance of the SDS in a similar way.

In addition, velocity information of the CMDs that is provided through various means such as GPS and network based velocity determination means can be used to aid in discriminating CMDs that could be in a moving vehicle from those that are stationary and therefore not in a vehicle. For example, if it is determined that the VDS is in motion, and a CMD associated or registered with a VDS is not moving, it can be inferred that the CMD is not in the moving vehicle and should not be disabled, and similarly the probability that the other CMDs associated with the vehicle is raised allowing potentially a more accurate or more timely determination of which CMD should be disabled.

Similarly, if the velocity of associated or registered CMDs differs from the velocity of the VDS it can be inferred it is not in the associated vehicle, or, if it matches the velocity of the VDS it is likely in the vehicle. Similarly, the direction of the velocity of either the VDS or the CMD can also be used to further clarify the velocity information and infer if a CMD is in a target vehicle or not depending if the direction of velocity of a CMD matches that of a VDS or not.

In one embodiment, location information from previous trips may be used to improve the ability of the SDS to identify if a CMD is in a vehicle as described previously. This information may be stored in a memory, e.g., the SDS 125, SDD 110 or both. The location of a MCBL or SCBL, may be provided by the subscriber via the SDRS 105 and stored in the SDD 110, or this location may be inferred by the SDS from data from previous trips. By way of example, if location information indicates that a high percentage of trips starting from a particular geographical location are determined to occur with a specific CMD in a vehicle associated with a VDS, then it can be inferred that location is a SCBL associated with that specific VDS and CMD, and similarly if previous trip information captured by the SDD and or SDS indicates that multiple CMDs are associated with a vehicle VDS are present in trips that start from that location, or that CMDs associated with the vehicle are frequently at that location, then it can be inferred that that location is a MCBL for that VDS and CMDs. As described elsewhere, this information can then be used by the SDS to calculate the probability that a specific CMD is in a vehicle at trip start independent of CMD location information, thereby improving the ability of the SDS to quickly determine which CMDs to disable.

In one embodiment, on trip start the SDS is operable to compare the trip start location for a vehicle associated with a VDS (determined either from the location captured at the end of the previous trip, or from location information provided by the VDS at trip start) with the location of a MCBL associated with the VDS, and in the case where the location of trip start is distant from the MCBL, the SDS is operable to determine that there is a high probability that the CMD in the vehicle during the previous trip is the CMD in the vehicle at current trip start, thereby allowing an immediate disable signal to be sent, or in other ways increase the effectiveness of the SDS by increasing the effectiveness of discrimination.

In one embodiment, on trip start the SDS is operable to compare the location of the VDS on trip start with the geographical location associated with a SCBL for that VDS, allowing the SDS to determine there is a high probability that the CMD associated with that SCBL and VDS is within the vehicle, thereby allowing an immediate disable signal to be sent, or in other ways increase the effectiveness of the SDS by increasing the effectiveness of discrimination.

In one embodiment, on trip start the SDS is operable to compare various CMDs last known locations with the time and geographic location of a trip start in order to establish on trip start whether a particular CMD has a low probability of being within a vehicle. In this embodiment, the SDS is operable to calculate the distance between the last known location of a CMD and compare that with a VDS start of trip location, as well as the time of last known location and the time of trip start to thereby calculate the velocity that the CMD would have to have been travelling to be in the vehicle at trip start, and compare that with a threshold velocity to establish the probability that the CMD is within the vehicle. By way of example, if fifteen minutes prior to the start of a new trip, an associated CMD was identified to be 30 miles away from the VDS there is a low probability that CMD can be in the vehicle as the CMD would have to have been travelling at 120 mph to be in the vehicle. Thereby, establishing the CMD does not require disabling, and increasing the probability that other associated CMDs may be in the vehicle, thereby increasing the effectiveness of the SDS by increasing the effectiveness of discrimination.

In one embodiment, the SDD may accumulate location information over time from VMD and the CMD associated with the VMD. With this information the SDS may autonomously determine home or base areas, or areas where there is a high probability a trip may start with one of several CMDs, such as a home where all CMDs may be frequently located (a MCBL), or alternately a location where there is a high probability only one CMD is located and therefore a high probability that at trip that starts there is associated with that CMD (a SCBL).

Information recorded in the SDD, e.g., location of VDS, location of CMD, velocity information, direction information, SCBL information, MCBL information, location of CMDs previous trips, e.g., trip ending information, CMDs identified in vehicle on previous trip, can be used to improve the performance of the system and lessen latency, by a) allowing immediate disabling with subsequent verification, b) immediate low-accuracy location information, or immediate high accuracy location information to increase the certainty that a CMD is in a vehicle, or c) lessen the time necessary to make the determination that a CMD is in a vehicle or, d) eliminate the need for location accuracy queries, e) allow the use of a low or high accuracy location information query performed significantly after trip start to provide a check to confirm that a particular CMD is in our out of the car after a more immediate disable signal has been sent to the CMD.

Figure 12A:
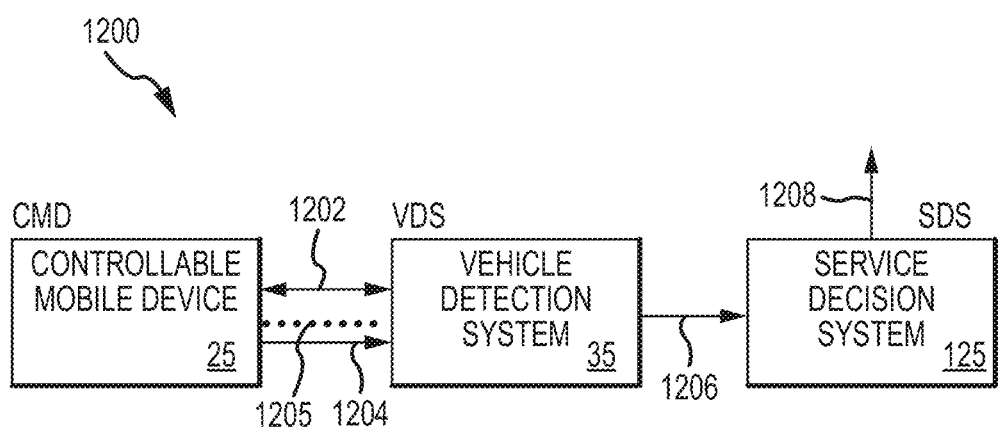
FIG. 12A discloses a system diagram of an illustrative embodiment for a system for controlling mobile devices.

FIG. 12A discloses a system diagram of an illustrative embodiment for a system for controlling mobile devices.

Referring to FIG. 12A, the system 1200 includes a CMD 25, a VDS 35 and SDS 125 in communication with each other. The system 1200 includes other components as described with further detail in system 10 of FIG. 1 and the subset of components are only shown for convenience and not meant to be limiting. The system 1200 is operable to determine whether a CMD is in a vehicle and also operable to disable the CMD.

The VDS 35 is operable to sense a unique wireless signal (UWS) 1205 from a CMD 25 or plurality of CMDs. In a preferred embodiment, the VDS 35 can be configured with an RF receiver or other type of receiver to receive and interpret the UWS 1205.

The UWS 1205 may be any type of communication signal, e.g., a Bluetooth signal, low energy Bluetooth signal, ZigBee, WiFi or other wireless signal. Sensing of UWS 1205 from the CMD may be closed-loop 1202, in which a handshake type connection is made between the VDS and the CMD (such as a Bluetooth handshake) or open-loop connection 1204, in which the VDS identifies a UWS transmitted from the CMD but does not create a handshake connection with the device.

In one embodiment, the UWS 1205 includes an identifier that is unique to a particular CMD. The identifier may be an encrypted or non-encrypted alpha numeric code that is compatible with an established protocol, e.g., Bluetooth protocol or other IEEE protocol. Moreover, more than one unique identifier may in the UWS 1205, e.g., an established protocol identifier and a priority protocol identifier. In a preferred embodiment, the UWS is the transmission signal from the CMD that is used to communicate with a cell tower and therefore requires no additional transmission capability on the CMD. In this embodiment, the VDS is operable to recognize the UWS as distinct and unique to the CMD. Optionally, the MSDS may provide information to the VDS by various means to enable it to decrypt and or recognize the UWS.

In this embodiment, the VDS 35 is operable to receive the UWS 1205 and interpret the signal so as to be able to identify whether the signal is being transmitted by a specific CMD 35 associated with the VDS 35, and to thereby send a signal to the SDS 125 that a particular CMD 35 is in or proximal to the vehicle. Moreover, the UWS 1205 may be user controlled therefore being able to be disabled by a user, either inadvertently or intentionally, so as to conserve power of the CMD, or to attempt to defeat the system.

Figure 12B:
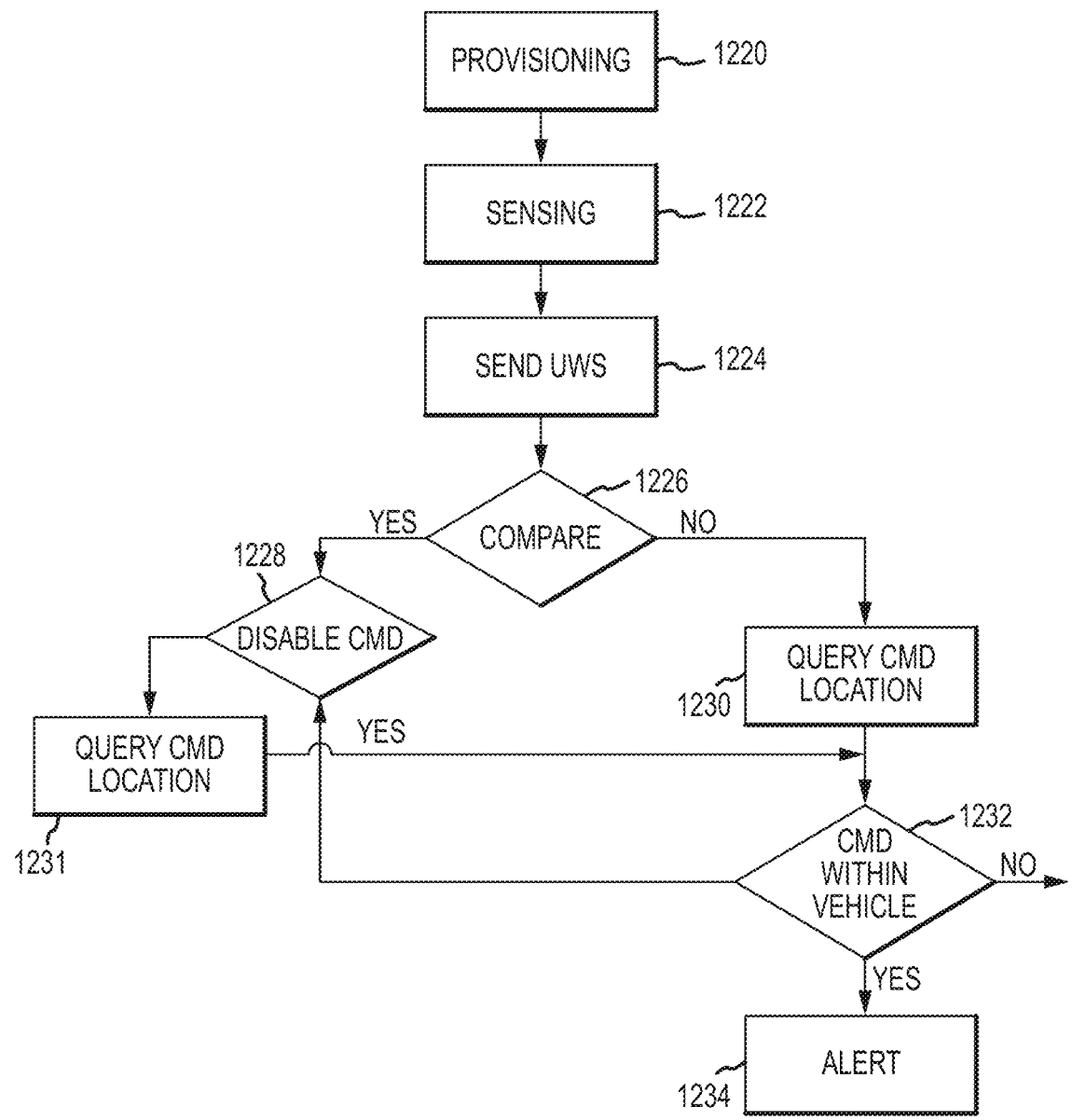
FIG. 12B discloses a flowchart of a simplified embodiment of a technique performed by the mobile services control system to determine if a CMD is in a vehicle with a VDS.

FIG. 12B discloses a flowchart of a simplified embodiment of a technique performed by the mobile services control system to determine if a CMD is in a vehicle with a VDS.

Referring to FIG. 12B, provisioning is performed to establish or associate a particular CMD with a UWS 1205. The provisioning (Step 1220) may be conducted by at least three different provisioning techniques including i.) entering the desired UWS 105 identifier associated with a particular CMD to SDD 110 via SDRS 105 or other part of the system, ii.) locating the CMD near the VDS, the VDS receiving the UWS 105 signal associated with a particular CMD and registering it as associated with a CMD identified as within the vehicle via various means including SDRS 105, and iii.) automatically storing a UWS 105 associated with a particular CMD in the SDD 110, by identifying that a CMD is within a vehicle containing a VDS by other means described herein, and then registering the UWS 105 received by the VDS as associated with that CMD.

Next, sensing is performed with the VDS (Step 1222) to determine whether the VDS is in a safe or unsafe state. An unsafe state is a condition in which the user of CMD could potentially be distracted from driving for instance, they are in a vehicle that is or will be moving. Indications of an unsafe can include information the establishes the vehicle is moving, that a vehicle is above a certain speed threshold, that a key has been turned on, that a battery voltage indicates that a vehicle is prepared to move, that a vehicle is in a location such as on a highway, engine RPM indicative that a vehicle may moving or is about to move, or vibration that indicates that a vehicle is moving or may be moving.

Moreover, an unsafe state may include a condition in which the vehicle is not moving, but that it is in an unsafe condition where distraction can be a problem. By way of definition, throughout this document the terms moving or in motion, shall mean any indication that the vehicle is about to begin a trip, is in mid-trip, and/or is in some other unsafe state where a CMD could potentially be distracting, independent of whether at that point in time the vehicle is actually moving.

If an unsafe state is sensed go to step 1224. In step 1224, the UWS 1205 is communicated to the SDS 1208 from the VDS 35 with communication techniques described herein.

Next, comparing the UWS 1205 with a CMD associated with the VDS is performed via SDS or other part of the system 13 (Step 1226). The comparing step 1226 may include referencing tables in the SDD 110 to determine whether a particular CMD is associated with the UWS 1205, or other information available electronically, including data collected for other means that correlates a unique UWS signature to a particular CMD and or optionally a VDS.

If an associated CMD is found for the compared UWS 1205, go to step 1228 in which the associated CMD is disabled (Step 1228) using techniques described herein. If no associated CMD is found for the UWS go to Step 1230. Optionally, after Step 1228, if only one of multiple CMDs associated with a VDS are identified and disabled, go to Step 1231 to establish if there are other CMDs within the vehicle that may have disabled UWS via a query. The query in Step 1231 in a preferred embodiment is a low cost query.

In Step 1230, the location of CMD associated with the VDS are queried as a means to determine if CMDs are within the vehicle. The location may be queried as described with reference to FIG. 11B or other techniques described herein may be used to determine whether an associated CMD is within the vehicle. If an associated CMD is determined to be within the vehicle go to step 1228 and disable CMD. Moreover, as the CMD is determined to be within the vehicle but a UWS associated with the CMD was not received by the VDS, it indicates that the UWS was disabled, the SDS can optionally send an alert. (Step 1234).

The alert provides notice to a third-party or the owner that the owner of CMD 25 has inadvertently or purposefully disabled the UWS transmission communication means, e.g., Bluetooth, and the like. The alert can be transmitted by email, text message, through the internet to the user via a web interface, or by other means. The alert may include one or more of the following: identity of the CMD, identity of the VDS or vehicle, identity of the CMD owner, time of alert, number of previous alerts, and location of the VDS at the time of alert. The alert may also be sent directly to the CMD owner to alert them to reeneable the UWS. This alert provides a means for ensuring that the UWS remains enabled thereby improving the effectiveness of the SDS.

After disabling a CMD in step 1228, optionally a check may be performed to determine if multiple CMDs are in a vehicle by querying location of registered or associated CMDs with the VDS (Step 1231 and Step 1232). As it is a check, rather than a primary means for determining if a CMD is in the vehicle, the query may be delayed to ensure adequate separation from the start of trip location, or may be a low cost query, so as to lessen the frequency and cost of location queries. If additional registered CMDs are found in the vehicle, disable the CMDs (Step 1228) and optionally send an alert (Step 1234).

Alternately step 1228 and step 1230 may determine whether a CMD is in a vehicle, or should be disabled by other means described herein that may or may not require a location query.

Figure 13A:
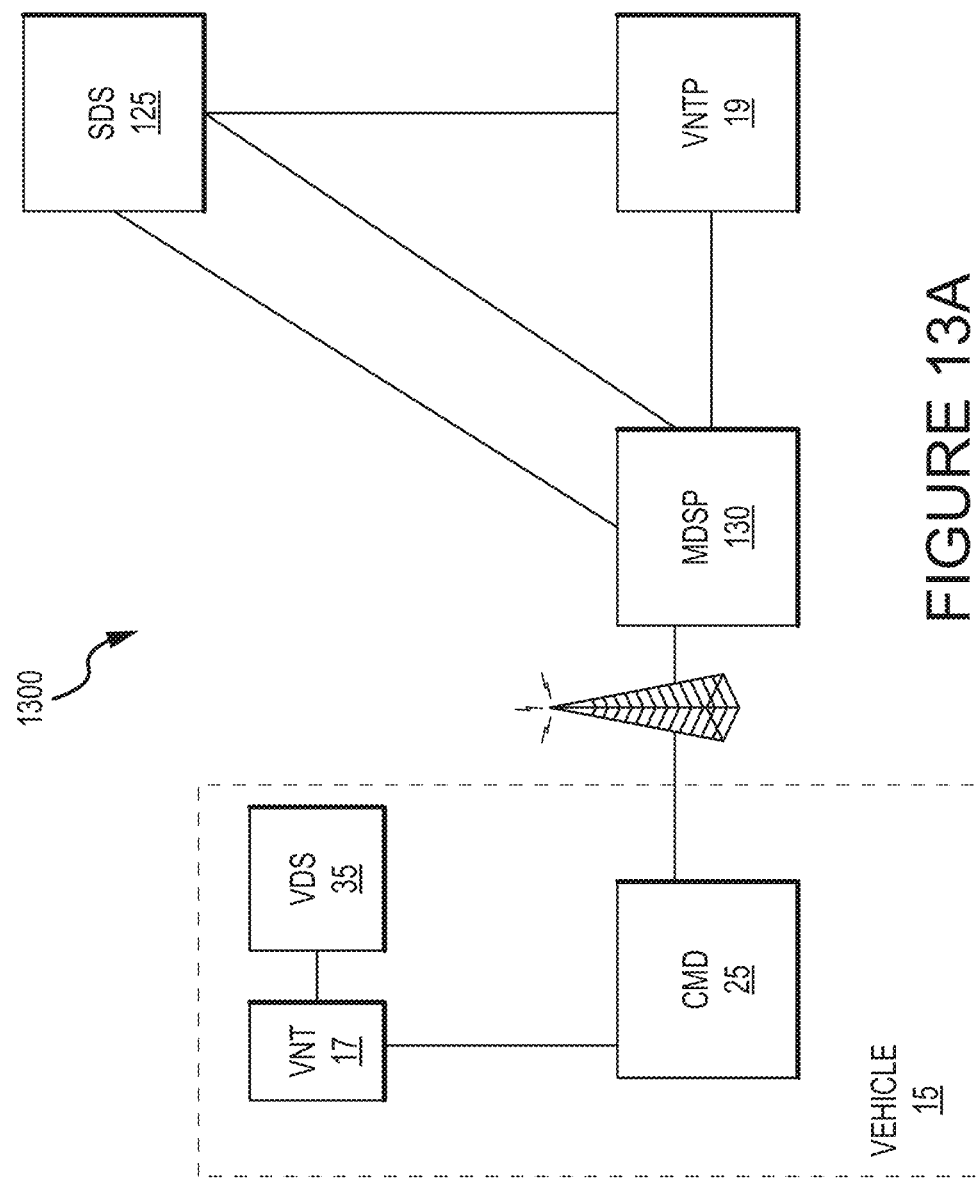
FIG. 13A discloses a system diagram of an illustrative embodiment for a system for controlling mobile devices.

FIG. 13A discloses a system diagram of an illustrative embodiment for a system for controlling mobile devices.

Referring to FIG. 13A, the system 1300 includes a Velocity Notification Transmitter (VNT) 17, vehicle 15, CMD 25, a VDS 35, a Velocity Notification Transmitter Processor (VNTP) 19 and a SDS 125 in communication with each other. The system 1300 includes other components as described with further detail in system 10 of FIG. 1 and foregoing components are shown for convenience.

The VNT 17 described herein can be utilized in any aspect of the invention. In one embodiment, the VNT 17 is a subset of the VDS 35 as a separate hardware and/or software feature. Alternatively, the VNT 17 may be a standalone hardware and/or software feature. In this embodiment, the VNT 17 is located within the vehicle 15, and provides a unique wireless signal over a short range whenever the vehicle 15 is moving. The unique wireless signal is of a form that is received by the CMD on a similar frequency to that used for communication between the CMD and the MDSP, or some other frequency able to be received by the CMD during normal operation. The signal may be similar to that provided by a cell carrier femtocell repeater, or it may be some other signal that the CMD is operable to receive without the need for CMD software or firmware beyond that needed for normal operation, or with minimal modifications or minimal software or firmware required to receive and interpret the VNT signal.

In one embodiment, the VNT is located within the vehicle and provides a unique wireless signal over a short range whenever the vehicle is in an unsafe state. The wireless signal is configured to be received by a CMD. In the preferred embodiment, the wireless signal is transmitted at a frequency similar to that of a cell tower, however, the wireless signal may be Bluetooth, Zigby, or any other signal that has a CMD transmission/receive frequency or other similar RF protocol to permit communication with a CMD. The wireless signal contains a unique identifier for the VDS.

In one embodiment, the unique wireless signal provided by the VNT 17 is transmitted at a frequency similar to that of a network cell tower, so that RF receivers on the CMD used for communicating to cell towers also receive the signal from the VNT, with the range of the VNT transmission such that it is only received by CMDs within the vehicle or near the vehicle.

Moreover, the unique wireless signal transmitted by the VNT 17 can be formatted so as to appear as an additional cell tower to the CMD, with a tower ID including a unique identifying characteristic that varies depending on the velocity or state of the vehicle and unique wireless signal can also include identifying characteristic that are unique to the VDS. For example, the unique wireless signal can be configured with any existing communication protocol to mimic a cell tower or to provide some other form of signal that will be forwarded to the MDSP 130.

In one embodiment, a CMD that has received a unique identifying characteristic from the VNT processes the signal as if it were a cell tower. Thereby, the CMD provides the VNT cell tower information to the MDSP 130 or a part of MDSP 130 communication protocols, with the presence of the unique identifier data providing data to the MDSP that indicates that a specific CMD is within a vehicle associated with a specific VDS, and the vehicle is in an unsafe state. For instance, the cell tower ID information may be formatted to be processed by the CMD as a functional cell tower ID, but contain unique information within the cell tower ID that indicates to the VNTP that the cell tower ID contains information associated with the System.

In a preferred embodiment, the unique wireless signal from the VNT is of a low signal strength, and/or sends other information that prevents the CMD from connecting to it as a functioning cell tower, e.g., the unique wireless signal may include a tower busy signal to prevent connection or other signal as known in the art in order to prevent connection. The MDSP 130 identifies this unique wireless signal through a VNT processor identifier (VNTP) 19.

In one embodiment, the unique wireless signal includes a VNTID as part of the signal generated from the VNT. The VNTID is configured to include a unique identifier of a VDS, information about the state of the VDS, e.g., unsafe state or safe state, and/or may include other information about the vehicle, e.g., velocity, direction, RPM, on, off, battery voltage, and the like. The VNT processor and/or software is operable to process the VNTID and identify it as information associated with any of the systems described herein, to process the VNTID so as to identify the unique identifying information associated with the VDS and to associate that information with a unique CMD identifier, such as the CMD phone number.

In one embodiment, access to the VNTID can be provided by the VNTID through the internet, or other means to the SDS 125 indicating the presence of a particular CMD within a particular moving vehicle. This information is then combined with other collected information relevant to distracted driving to determine if a particular CMD is being used by a driver of a moving vehicle, and if so, a notification is transmitted to the MDSP, third party network element provider, or wirelessly to the mobile device itself, enabling the MDSP, a third party network element provider, or software on the CMD itself to limit various distracting functions provided by the CMD using means described elsewhere in this description, or to disable the CMD using techniques described elsewhere.

In another embodiment, the VNTID can be interpreted by software or firmware within the CMD to indicate that the CMD is within a moving vehicle 15. The CMD upon receipt of an interpreted signal then provides notification wirelessly from the CMD to the SDS via the MDSP, that a particular CMD is within vehicle 15 and the vehicle is in an unsafe state, allowing the SDS to disable the CMD through techniques included herein.

In one embodiment, the VNT 17 is operable to connect to the MDSP, either directly through a wireless connection, or through the CMD to the MDSP, to receive provisioning information necessary for the VNT to provision itself as a cell tower, in an equivalent manner to how a femtocell repeater is provisioned to act as a cell tower.

Figure 13B:
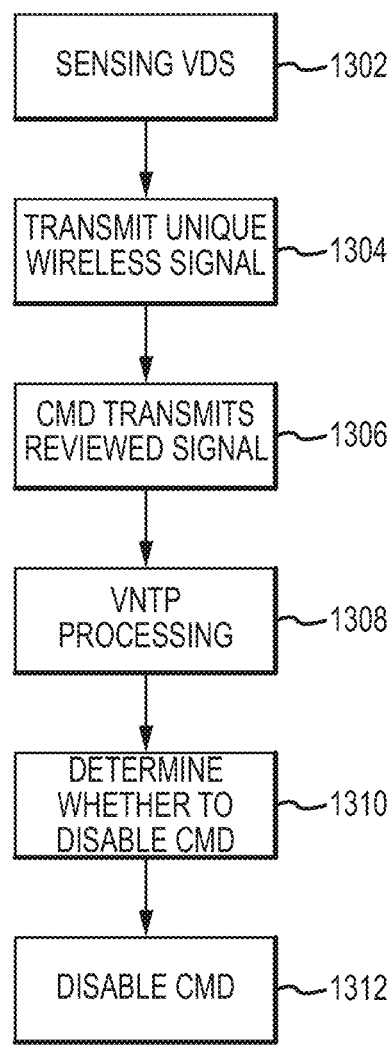
FIG. 13B discloses a flowchart of a simplified embodiment of a technique performed by the mobile services control system to determine if a CMD is in a vehicle with a VDS.

FIG. 13B discloses a flowchart of a simplified embodiment of a technique performed by the mobile services control system to determine if a CMD is in a vehicle with a VDS.

Referring to FIG. 13B, the flowchart describes disabling a CMD by utilizing a VNTID without the need for specialized software on the CMD, and/or the need for any VDS to connect to the network.

Initially, sensing of the VDS is performed to determine a safe or unsafe state of the vehicle. An unsafe state is a condition of the vehicle that indicates that a CMD may be potentially distracting as previously described herein. Again, an unsafe state or condition is not limited to when the vehicle is moving, but may include an unsafe condition where a distraction can occur.

In one embodiment, movement or other indication of a potentially unsafe state, such as sensing vehicle start or key on may be sensed directly by connection to the vehicle computer network either by the OBDII port or some other wireless or directly connected means, or the movement may be sensed by a GPS device connected to the VNT, or by accelerometers connected to the VNT.

If an unsafe state is sensed a unique wireless signal and VNTID is transmitted from the VNT 17 (Step 1304). Next, a CMD receives the unique wireless signal and VNTID and retransmits VNTID via communication network and MDSP 130 (Step 1306).

In one embodiment, access to this data is then provided by the MDSP through the internet, or other means to the SDS indicating the presence of a CMD in a vehicle that is in an unsafe state. This information is then combined with other collected information relevant to distracted driving to determine if it is probable that a particular CMD is being used by a driver of a vehicle in an unsafe state, and if so, a notification is transmitted to the MDSP, third party network element provider, or wirelessly to the CMD itself via the MDSP, enabling the MDSP, a third party network element provider, or software on the CMD itself to limit various distracting functions provided by the CMD, such as texting, computer software applications requiring interaction with the mobile device owner, or talking on the cell phone, or through other techniques described herein.

Next, the VNTP processing is performed (Step 1308). The VNTP processing receives information from the network including the VNTID and the identity of the CMD associated with the VNTID. The VNTP then processes this information to extract the VDS identity, information as to the state of the vehicle, and the identity of the CMD associated with the VNTID. Next the processing includes sending the bundled information from the VNTP 19 to the SDS 125.

The SDS 125 is operable to determine the probability that the CMD is in use by a driver of a vehicle by combining the bundled information from the VNTP 19 with information related to the CMD, the vehicle and the driver that is available to the SDS via the SDD, using techniques described herein (Step 1310) and if the SDS determines it is likely the CMD is in use by a driver of the vehicle disable the CMD using techniques described herein (Step 1312).

Figure 14:
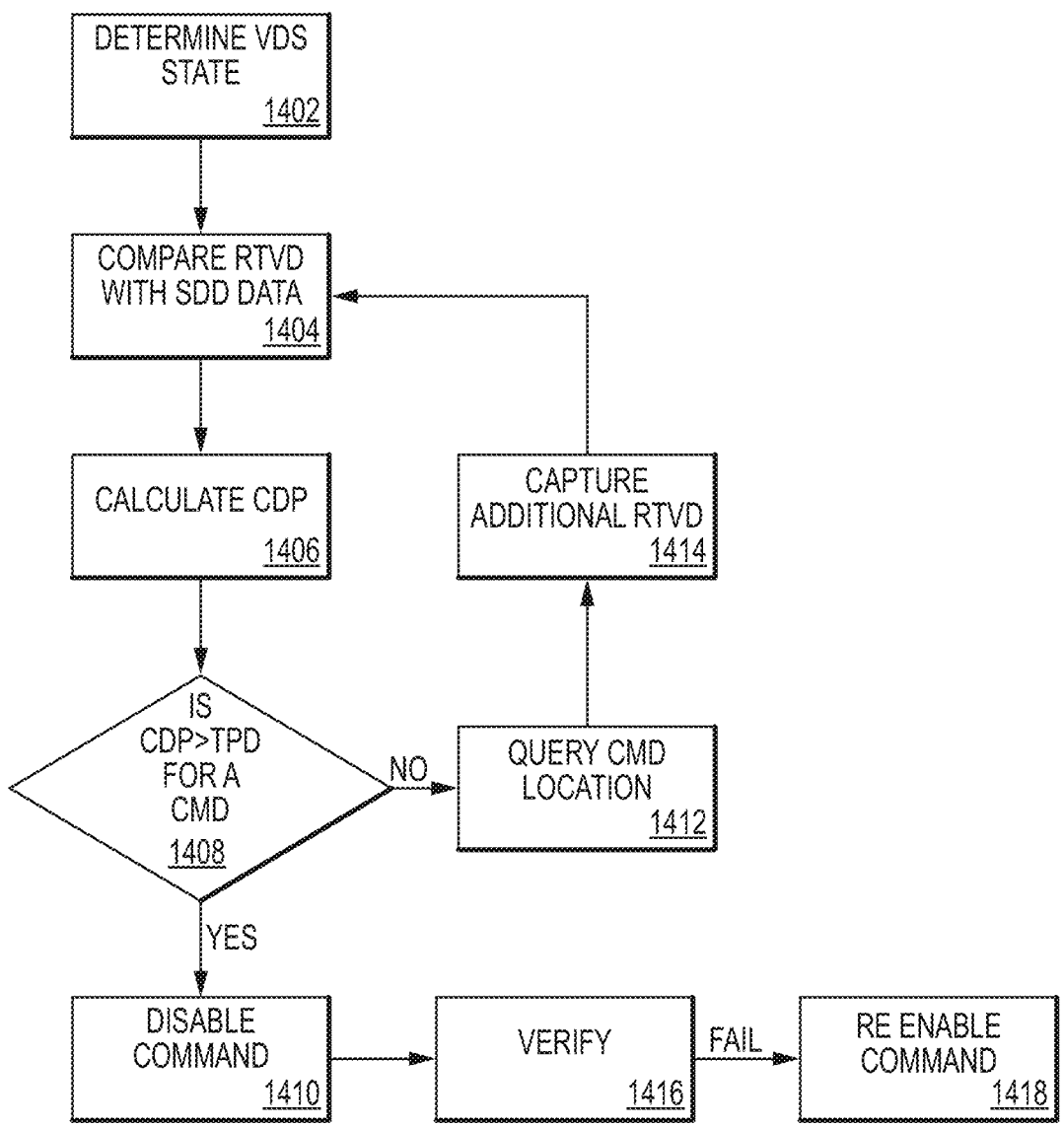
FIG. 14 discloses a flowchart of a simplified embodiment of a technique performed by the mobile services control system to determine if a CMD is in a vehicle with a VDS.

FIG. 14 discloses a flowchart of a simplified embodiment of a technique performed by the mobile services control system to determine if a CMD is in a vehicle with a VDS.

In this embodiment, additional information is utilized in the determination of whether to disable a CMD or multiple CMDs. This additional information may be obtained in a variety of different ways and can include information specific to a particular driver including information collected during provisioning (Driver Profile Information, DPI), information related to the driving behavior of a driver or vehicle (Driving Behavior Pattern Information, DBPI), information related to previous and recent trips (Recent Trip Data, RTD), information related to the frequency and nature of CMD overrides (Driving Override Record, DOR), information collected during a trip including but not limited to information related to a vehicle, driver, CMD, VDS, or other information (Real Time Vehicle Data, RTVD). All of this information may be stored in the SDD 110 or other storage device, or may be processed by the SDS and not stored.

This information can be transmitted by the VDS to the SDS during previous trips, either via data collected from the vehicle via the OBDII port, through integral velocity, location and acceleration sensors on the VMD, other sensors integral to the VDS, or similar data collected and transmitted by a CMD within the vehicle, as well as data transmitted or captured during a previous trip from other sources associated with a vehicle, CMD, VDS or driver.

In one embodiment, this information is used to generate a unique DPBI for each of the drivers associated with CMDs.

In one embodiment, the DPBI and DPI includes driving patterns and information associated with specific portions of a trip (such as a specified period at the beginning or end of a trip), or for specific locations during a trip (such as behaviors at stop signs, or geographic locations with specific speed restrictions), or data collected throughout the trip. Moreover, the DPBI can include such information as acceleration rates, maximum speed, average speed, trip start locations, trip end locations, driving behaviors at stop signs, driving behaviors during cornering, vehicle route information during a portion of the trip, linear acceleration patterns, braking patterns, cornering acceleration patterns, rpm vs. location patterns, rpm vs. velocity patterns, rpm patterns, times of day a specific driver has been determined to be likely to be driving, probability a certain driver will be driving a vehicle, probability that a certain driver will be driving a vehicle when there are more than one registered CMDs in the vehicle, times of day a particular driver has been determined to be likely to be driving along a certain route, driver seat position, time to first motion of the vehicle after key-on, velocity while backing up, selection of radio channel, choice of audio or video entertainment, key identification data, and any other information able to be captured by the onboard vehicle electronics, other sensors, provisioning or through other techniques that could be unique to a particular driver.

In one embodiment, RTVD may include self-identification information (Self ID Information) that may be intentionally sent by the driver of the vehicle to identify them as the driver such as sending a text message or making a call that can be received by the SDS and associated with a specific driver, opening a self-ID application or website on their CMD that transmits the identity of the driver to the SDS, by performing actions unique to a particular driver of the vehicle that can be sensed by the VDS via the OBDII connection or other means of sensing vehicle information, and transmitted to the SDS, such as, but not limited to, blinking the high-beam lights a certain number of times, turning on lights a certain amount of times, tapping the brakes a certain number of times or any other means for communicating to the SDS that a specific individual is driving the vehicle.

In one embodiment, the SDS disables all CMDs associated or registered with a VDS on sensing an unsafe state until a driver of the associated vehicles self identifies using communication techniques described herein, providing a motivation for the driver to self-identify due to the inconvenience from an associated CMD of a non-driver being disabled.

In one embodiment, DOR can include data from previous trips, during which certain individuals in the vehicle transmitted a request to override a disable command from the SDS for a specific CMD, as described elsewhere in this description, indicating a possibility that the CMD was at that time not associated with the driver of a vehicle and or not within the vehicle, implying the SDS had made an incorrect determination that a particular CMD was in a vehicle, or associated with the driver of the vehicle. This information then being used to improve the SDS ability to discriminate by identifying possible errors in probability calculations that can be corrected, either as an autonomous capability of the SDS software (self learning), or by manual reprogramming of the SDS software.

DBPI can be associated with a specific driver by various means, such as positively identifying the driver later in a trip by other means such as collocation of a CMD within the vehicle, statistically by identifying a particular unique driver profile, and then later associating it with a specific driver when the collected data indicates a high probability that the unique driver profile is associated with a specific driver, by self identifying as described herein or other techniques that associate a driver with a particular driving pattern.

DPI for specific drivers associated with a specific vehicle can also be captured directly via the SDRS user interfaces. For example, information on the probability that a specific driver will be driving a specific vehicle, probability that a driver will start a trip at a particular time of day, geographic locations that a particular driver often starts a trip from (for instance a home or place of business), a location the driver often ends a trip at, probability that if multiple registered drivers are in a specific vehicle, that a particular registered driver will be the driver of that vehicle (for instance, when the family is in the car, the mother is likely to be the driver), the probability that a specific driver will "self police" and voluntarily not use a distracting device, and the probability that a specific driver will not use a distracting device when other passengers are in the vehicle.

Collected data can also include data collected by the SDS during recent trips (Recent Trip Data). This data can be associated with a) the specific VDS b) concurrent trips associated with a different VDS that has associated drivers that are also associated with the specific VDS, c) most recent location of CMDs associated with the specific VDS, d) location of the previous end of trip for the specific VDS, e) location of previous end-of-trips for associated VDS's, and other recent trip data specific to a particular VDS and the associated CMDs.

In one embodiment, the SDS incorporates a Real Time CMD Driving Probability (RTCDP) processor as a component of the SDS which is operable to compare RTVD information with DPI, DBPI, RTD, DOR, Self ID information and other information (collectively the ID Information) to calculate the probability that a particular CMD is either in a vehicle or associated with the driver of the vehicle, the CMD Driving Probability (CDP). The RTCDP is operable to compare information and patterns represented in the Real Time Vehicle Data with information and patterns in the ID Information to calculate the CDP. In one embodiment, the RTCDP processor identifies individual elements of similarity or dissimilarity between the RTVD information and the ID Information, and calculates the CDP by applying historical weighting factors to each areas of similarity that increase probability and then applying historical weighting factors to each area of dissimilarity the decreases probability and calculating the resulting CDP by calculating aggregate probability based on these individual probabilities. For example, if a comparison of RTVD and DPI information shows that a vehicle is being driven at a time of day where there is a low probability an individual with a given CMD would be driving, this would indicate a decreased probability for that CMD being distracting, while simultaneously, the behavior of the associated vehicle at a stop sign may be similar to that associated with DPBI information associated with that same CMD and individual indicating a higher probability that the CMD is associated with the vehicle driver, while simultaneously, the location of the vehicle matches route information within the DPBI that indicates an increased probability that the CMD is associated with the driver of the vehicle. The RTCDP then uses weighting factors for each of these probabilities (established historically from the data, or entered manually) to calculate a composite CDP, which may or may not indicate a high probability that the CMD is being used by a driver and potentially distracting. In similar ways the RTCDP can compare any RTVD with other ID information data or other data to identify elements of similarity or difference between the RTVD and ID information and thereby calculate aggregate CDP for comparison with threshold probability values for disabling.

In one embodiment, the time of day that a particular vehicle is being driven is compared with DPI indicating the probability that a driver is driving at that time of day.

In one embodiment, the route of a vehicle in the first portion of trip is compared with DBPI related to the routes taken by specific drivers to indicate the probability that a specific driver is driving the vehicle.

In one embodiment, at least one of the velocity, acceleration and de-acceleration information of a vehicle at or near a stop sign is compared with DBPI related to at least one of the velocity, acceleration and de-acceleration information of specific drivers at or near stop signs, indicating whether they typically do a rolling stop, or a full stop, or other behavior that determines the probability that a specific driver is driving the vehicle.

In another embodiment, the RTVD information related to accelerations during cornering is compared with DBPI related to specific driver cornering to indicate the probability that a specific driver is driving.

In another embodiment, the RTVD information related to velocity compared to speed limit, or velocity on a particular segment of a route, is compared with equivalent DBPI to determine the probability that a specific driver is driving.

In another embodiment, RTVD information related to the time between turning the key of the vehicle on and first motion, which can be associated with individual-specific time taken to prepare to drive after turning on the car, is compared with equivalent DBPI to determine the probability that a specific driver is driving.

In another embodiment, RTVD information on braking patterns during a particular segment of a trip, or at any point in the trip, such as average de-acceleration or maximum de-acceleration are compared with equivalent DBPI to determine the probability that a specific driver is driving.

In another embodiment, RTVD information on rpm vs. velocity, indicative of individual-specific shifting patterns in both automatic and manual transmissions is compared with equivalent DBPI to determine the probability that a specific driver is driving.

In another embodiment, probabilities from individual positive and negative correlations between RTVD and DPBI information are combined to provide a more accurate composite CDP.

Referring now to FIG. 14, the state of VDS is determined by the SDS through means described herein throughout (Step 1402). When the VDS senses that the vehicle is in a potentially unsafe state, such as the engine is running, or the vehicle is moving, or another unsafe state as described elsewhere, it notifies the SDS via any communication technique as described herein of the potentially unsafe state.

After an unsafe state has been sensed go to step 1404.

The RTCDP component of the SDS is operable to compare RTVD information with SDD data including at least one, or a combination of Driver Profile Information, Self ID Information, Driving Behavior Pattern Information, Recent Trip Data, Driver Disable Record Information and other data related to identifying the driver of a vehicle. (Step 1404).

Next, to determine the probability that a specific driver associated with a particular CMD is driving a vehicle (CMD Driving Probability, CDP) is calculated (Step 1406) using techniques described herein. The SDS is operable to compare the CPD with a threshold probability (Threshold Probability for Disabling, TPD) that is a probability value that establishes if the SDS should enable or disable a CMD, and has been pre-established to provide optimum SDS performance, or is autonomously derived by the SDS by comparing the accuracy of disable discrimination from previous trips (determined by evaluating DOR information or other means, Step 1408).

When the TPD is exceeded, the SDS is operable to send a signal to disable, or partially disable the function of a specific CMD, or alternately to record the identity of the driver in the SDS for subsequent comparison with CMD use records to report distracting CMD use as described elsewhere in this description (Step 1410).

Optionally, when the TPD is not exceeded, the SDS is operable to query locations of CMD associated with the VMD and compare those locations with the VMD location using techniques described elsewhere in this description, or to utilize any other information or process described herein that improves the ability of the SDS to determine if the CMD should be disabled (Step 1412). Moreover, the SDS is operable to update the CDP in real-time as additional information is received by the VMD (Step 1414).

Optionally, a verify step 1416 is performed to confirm CMD within the vehicle via a location query of CMD associated with the VDS through means described elsewhere. The verify step is describe herein with reference to step 1108 of FIG. 11B. If the verify step indicates that CMD that would not be distracting have been disabled send a reenable command (Step 1418) and optionally record this information in the SDD to allow the performance of the SDS to be improved In one embodiment, information associated with a SDS determination of when CMD may be used in a distracting manner is used to monitor instances of distracting CMD use rather than to disable the CMD. In this embodiment, information is recorded in the SDD or other means, or is provided real time to the SDS, related to the likelihood of the a CMD being in a vehicle that is in an unsafe state and possibly being used in a distracting manner. This information can include the identification of CMD that would have been disabled by the SDS by means described herein, the time the CMD would have been disabled, the location of the VDS, the calculated probability the CMD is in the vehicle, the calculated probability the CMD is in use by a driver, the location of the CMD, the identity of the vehicle, the velocity of the vehicle during a trip, the time that the CMD would have been enabled, the location at which the CMD would have been enabled, and other data from the SDS or RTVD associated with the use of a CMD in a distracting manner. For instance, the SDS may record information related to when a CMD was in a vehicle that was in an unsafe state, when a CMD would have been disabled by the system, when a CMD would have been enabled, by the system and the identity of the VDS it was associated with during the trip.

The SDS is operable to compare this information as to when a CMD was in a vehicle in an unsafe state, or the when a CMD was associated with the driver of a vehicle in an unsafe state, with CMD usage information provided by the MSDP or other parties indicating the time and nature of CMD function or operation (for instance, texting sending and receiving, call sending or receiving, or other use of the CMD) as well as any other information related to potential distracting use of a CMD. This usage information can be provided autonomously by the MDSP or a third party provider with access to that information, or can be provided by the subscriber by uploading usage information provided them by the MDSP, to the DSS via the SDRS or other means. The SDS is then operable to determine instances when the CMD was used in a potentially distracting manner, by comparing time of usage of the CMD with times that CMD use may have been distracting, record these instances and related data in the SDD, and provide reports and alerts to the CMD user, the vehicle owner, insurance companies, federal agencies, or other parties, so as to identify potentially distracting use of a CMD by a driver or passenger. These reports may be provided by email, by text, by web interface or be provided by other means. They optionally can include additional information beyond instance of distracting CMD use, including other relevant information, such as location of distracted use, velocity of the vehicle at the time, severity of the distracted use (such as use on high speed two lane roads), probability of occurrence, etc.

In another embodiment, any means described herein for determining if a CMD is in a vehicle that is in an unsafe state, and therefore should be disabled or enabled, and any information captured by the SDS and SDD by means described herein may be used to report instances of distracted CMD use as an alternative to disabling the CMD. Additionally, this information can be used in conjunction with disabling the CMD to confirm that the CMD was effectively disabled by comparing usage information with periods of time where the CMD should have been disabled by the SDS.

In embodiments described herein, the above techniques improve the performance of the SDS by one or more of a) lessening the time lag and improving the accuracy of determining if a CMD is in use by a driver of a vehicle, is in use by a passenger of a vehicle, or is not in the vehicle. b) lessening the need for time-consuming, costly, or ineffective discernment methods (such as location queries), and c) providing a more accurate record of CMDs that were in a vehicle or in use by the driver of a vehicle, that when compared with CMD usage records as described elsewhere in this description, provide a more accurate record of when a CMD was used in a potentially distracting manner.

Figure 15:
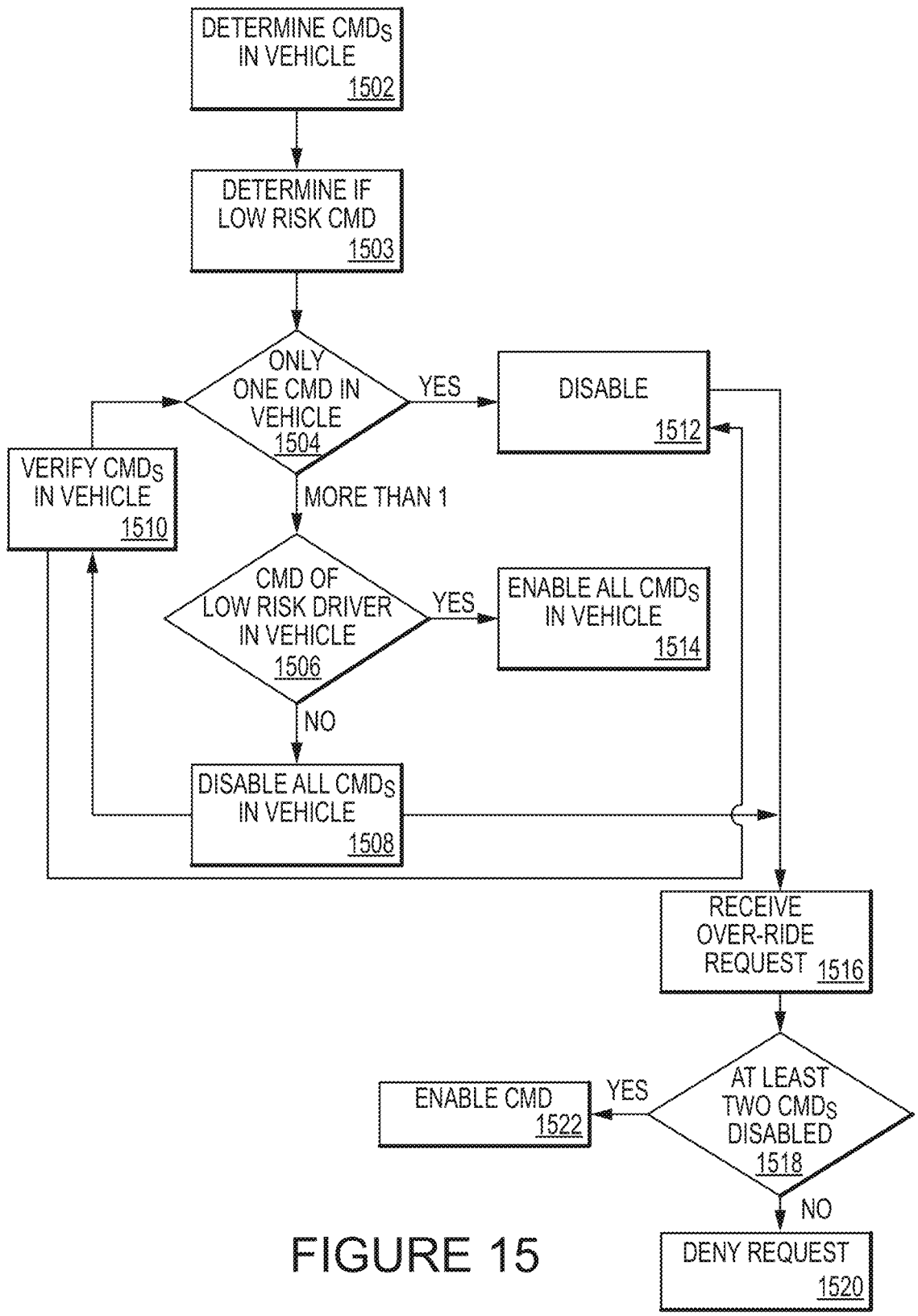
FIG. 15 discloses a flowchart of a simplified embodiment of a technique performed by the mobile services control system to determine if a CMD is in a vehicle with a VDS.

FIG. 15 discloses a flowchart of a simplified embodiment of a technique performed by the mobile services control system to optimize the number of CMDs that are disabled in a vehicle with a VDS so as to lessen the need for override requests.

Referring to FIG. 15, the flowchart illustrates a simplified embodiment of the processing for disabling certain CMDs when multiple CMDs are in a vehicle that recognizes that distracting CMD use of more prevalent when a driver is alone in the vehicle compared to when there are multiple people in a vehicle, and it is possible that they will self police to prevent distracted driving. The system utilized in this embodiment is generally described with reference to FIG. 1.

Determine CMDs associated or registered with the VMD are within the vehicle using techniques included elsewhere in the description (Step 1502). Determine if the CMD in the vehicle is associated with a low risk driver, e.g., a driver that is unlikely to use a CMD in a distracting manner when others are in the vehicle, and or, is likely to prevent others from using a CMD in a distracting manner in the vehicle they are within such as a parent, or in a commercial vehicle, a supervisor (Step 1503).

Determine number of other CMDs associated with the VMD in the vehicle (Step 1504). If it is determined only one CMD associated with the VMD is in the vehicle, send disable command (Step 1512), optionally, go to Step 1510 to verify if there are more than one CMDs in the vehicle. The verify step is described herein with reference to FIG. 11B (Step 1108).

If it is determined that there is more than one CMD associated with the VMD in the vehicle, the SDS is operable to determine if any of the CMDs in the vehicle is registered to a low risk driver (Step 1506).

If one or more CMDs are registered to low risk drivers, enable any previously disabled CMD associated with the VDS for the remainder of the trip and exit the process (Step 1514).

If none of the CMDs in the vehicle are registered to low risk drivers, disable all CMDs in the vehicle (Step 1508).

Optionally, continue to determine if CMDs associated with the vehicle are within the vehicle or not in the vehicle (Step 1510), and repeat step 1504 until all CMDs associated with the vehicle are determined to be in or out of the vehicle, or it is determined there is are more than one CMDs within the vehicle and one of the CMDs is registered to a low risk driver.

In one embodiment of the above cases, each CMD is able to send an override signal wirelessly to the SDS, either through a text message, or through some other simple function on the SDS described herein, requesting that the CMD owner is not driving, and requesting the SDS to re-enable potentially distracting functions (Step 1516). The SDS is operable to enable the CMD (Step 1522), or optionally to determine if there are at least two CMDs in the vehicle that have been disabled, so that on granting the override request, there will remain one CMD that is disabled, presumably the driver (Step 1518). If there are two CMDs disabled, go to Step 1522. If there is only one disabled CMD in the vehicle go to Step 1520. On re-enabling these functions, the SDS optionally can simultaneously send a notification to the owner of the vehicle, or to the subscriber that an override has been received and executed. If through these notifications, the owner of the vehicle determines that this override function is being abused, they have the optional ability to provide notification to the SDS that overrides shall not be allowed for that particular CMD without their authorization.

In one embodiment of the invention, it is desired to improve the ability of the VDS to provide data in real-time that the SDS that the vehicle is in an unsafe state or not, and reduce lags and inaccuracies in the ability of the SDS to disable and enable CMDs, as well as to provide data that indicates if a driver of the vehicle has attempted to disable the VDS.

In one embodiment, the VDS includes elements to improve VDS performance such as a) means to sense and transmit information helpful in determining if a vehicle is in a potentially unsafe state such as battery voltage, rpm, location and key-on or key-off signals, b) means to send and receive text (SMS) messages via the MSDS to the SDS, c) means to receive and respond via either SMS or other data transfer means to queries for specific vehicle information helpful in determining if a vehicle is in a potentially unsafe state such as rpm, battery voltage, location, velocity, key on, or key off, d) on-board timers that can connect or disconnect the wireless connection to the MDSP e) means to send data intermittently to the MDSP to confirm that the vehicle continues to be in an unsafe state or not. and f) means to connect the VDS to the MDSP when the VDP senses motion of the vehicle, key on, or some other event that indicates that the vehicle may be about to enter into an unsafe state (Unsafe State Indicator Data, USID).

In one embodiment, the VDS is operable to be in a standby mode where it is not connected to the MDSP but is powered. On recognizing USID data, the VDS is operable to immediately connect to the MDSP, and on connection to the MDSP, sends an SMS message to the SDS indicating that the vehicle may be in an unsafe state, such SMS message being able to be transmitted with a considerably weaker data connection than that required for other data transfer, allowing the VDS to connect to the SDS quickly in cases in which the wireless connection between the VDS and the SDS is weak (such as in a parking garage, or in the mountains). The means for sending the SMS immediately may be accomplished by the SDS sending an SMS query to the VDS while it is in standby mode, that would be automatically responded to when the VDS first connects to the MDSP, or by the firmware on the VDS automatically sending the SMS when it first connects to the MDSP. Optionally the data sent to the SDS via SMS can be either a simple flag indicating a possible unsafe state, or be the transmission of data such as the USID data that when combined with other data, helps the SDS better determine if the vehicle is actually in an unsafe state.

In one embodiment it is desired to enable the SDS to determine the end of a trip in the instance that the end of trip occurs in an area of weak wireless connectivity (such as a parking garage, or in mountainous areas). In this example, the VDS is operable to send an intermittent signal at a constant interval (for instance every 30 seconds) that transmits either a flag indicating the vehicle is in a safe, or unsafe state, or transmits USID data that enables the SDS to determine if the vehicle is in a safe or unsafe state. In this example, the SDS is operable to monitor signals from the VDS, and if it no longer receives signals at a regular interval for a pre-determined period, the SDS determines that the VDS either has ended a trip in an area of weak connectivity, or has entered an area of weak connectivity for an extended period in which a CMD would also lose connectivity and be less capable of distracting a driver. In either case, the SDS then is operable to send a re-enable command for the CMD until it again receives data indicating that the VDS senses a potentially unsafe vehicle state indicating both the unsafe state and that the vehicle is in a location with connectivity that allows potential distracting use of the CMD. Optionally, if the SDS does not receive signals from the VDS over a pre-determined period indicating weak wireless connectivity, the SDS is operable to query the VDS using SMS and the VDS is operable to responds to that query, providing USID data, or a flag, indicating that the vehicle is in a safe or unsafe state, such SMS transmission being able to occur in areas of weak connectivity, thereby increasing the effectiveness of the SDS in being able to determine if the vehicle is in an unsafe state. Alternately, the MDSP can provide data to the SDS indicating that a connection is present between the VDS and the MDSP, the SDS being operable to respond in a similar manner as that described above, when the MDSP data indicates that a connection between the VDS and the MDSP has been lost.

In one embodiment of the invention designed to discourage drivers from disabling the VDS, the VDS incorporates a rechargeable battery that provides sufficient power to maintain a wireless connection to the SDS and provide the SDS a signal that a VDS has been disconnected from the vehicle. The SDS is then operable to disable or partially disable the CMD or CMDs associated with that VDS until such time as the VDS is reconnected, or alternately to provide an alert to the vehicle owner that the VDS in that vehicle has been disconnected.

In one embodiment of the invention, it is desired to eliminate the lag time resulting from the establishment of the handshake connection between the VDS and the MDSP that occurs when the vehicle is turned on. In this embodiment, the wireless connection, is maintained between the VDS and the MDSP while the vehicle is turned off, so that it is not necessary to establish a handshake connection when the vehicle is turned on, thereby enabling the SDS to sense when a vehicle is in an unsafe state shortly after the vehicle is turned on. This connection may optionally be a limited functionality stand-by mode. Optionally, the VDS can include a timer that will disconnect the VDS to MDSP wireless connection after a certain number of hours, to prevent unnecessary battery drain when the vehicle is parked for multiple days (for instance when parked in an airport parking lot).

One embodiment, is directed towards a method for determining if a CMD is in a vehicle by utilizing one or more of velocity, direction of velocity, location in order to establish whether a CMD is in a vehicle, without needing location information from CMD and/or VDS. More specifically, this embodiment can be utilized with CMDs and VDSs having location and velocity capability. The velocity of a CMD is compared to the velocity of the VDS to see if it is substantially identical. Also, the direction of CMD is compared to the direction of the VDS to see if it is substantially identical. Monitor cell tower switching for CMDs indicating motion of CMD SDS utilizes the tower switching to indicate a CMD is moving or not when a VDS is moving. If CMD velocity or direction is substantially identical it indicates that a CMD is in that particular. Moreover, if CMD velocity or direction is not substantially identical it indicates that a CMD is not in a particular vehicle. In addition, if tower switching indicates CMD motion, while VDS is in motion, it increases the likelihood that CMD is in vehicle. If no tower switching then it indicates CMD is not in vehicle.

One embodiment is directed towards a method for determining if a CMD is in a vehicle by using one or more of previous trip and information and start of trip location and velocity. In this embodiment, locations are identified where multiple registered drivers may be in a vehicle at trip start (MCBL) and where a single registered driver may be in the vehicle (SCBL). In one embodiment, these locations may be identified by provisioning or be reviewing past trip history. If the vehicle starts from a location other than a MCBL, disable CMDs that were in the previous trip, then confirm CMDs in the vehicle through other verification procedures as described herein. If the vehicle starts from a location that is a MCBL, establish CMDs in the vehicle through various techniques described herein and disable CMDs in the vehicle. Evaluate the last known location of other registered CMDs to determine those that could not be in the vehicle at start of trip being located too far from the start of trip.

One embodiment is directed towards a method of determining if a CMD is in a vehicle by using one of more of following, provisioned information associated with a driver or vehicle or location, driving pattern information established from previous trip information associated with a specific CMD, and real time information from a current trip. Real time information during a trip is compared with previous information associated with a particular CMD, Vehicle or Driver (profile information) and a comparison is made between real time information and profile information. When real time information is similar to profile information, the probability that CMD is in the vehicle is increased. When real time information is dissimilar to profile information, the probability that CMD is in the vehicle is decreased. In a preferred embodiment, SDS compares the information with other information to determine overall probability that the CMD is in the vehicle and or if the CMD should be disabled. SDS compares this probability with a threshold value to determine if the CMD should be disabled. Presence of CMDs in vehicle can optionally be confirmed from other techniques such as location of CMDs versus location of VDS. In one embodiment, information includes information described herein including but not limited to: information associated with specific portions of a trip (such as a specified period at the beginning or end of a trip), or for specific locations during a trip (such as behaviors at stop signs, or geographic locations with specific speed restrictions), data collected throughout the trip, acceleration rates, maximum speed, average speed, trip start locations, trip end locations, driving behaviors at stop signs, driving behaviors during cornering, vehicle route information during a portion of the trip, linear acceleration patterns, braking patterns, cornering acceleration patterns, rpm vs. location patterns, rpm vs. velocity patterns, rpm patterns, times of day a specific driver has been determined to be likely to be driving, times of day a particular driver has been determined to be likely to be driving along a certain route, probability that a driver will be driving a particular vehicle, driver seat position, time to first motion of the vehicle after key-on, velocity while in backing up, selection of radio channel, choice of audio entertainment, key identification data, and any other information able to be captured by the onboard vehicle electronics, other sensors, provisioning or through other techniques that could be unique to a particular driver and/o self ID from driver.

One embodiment is directed towards a method of reducing lags between the time that a vehicle is in a safe or unsafe state and the ability for system to respond and disable CMDs. In this embodiment, using a network service, e.g., texting messages (SMS) to connect the VDS to the SDS in areas of weak connectivity, thereby keeping VDS connected to the MDSP when the vehicle is off to eliminate lags from connection making Monitor data from VDS on a regular time interval to determine if vehicle has ended trip in an area with weak connectivity. Query VDS if state of vehicle is unknown by SMS to receive vehicle information indicating state of vehicle, such as power on, velocity, rpm, battery voltage etc. Monitor VDS MDSP connectivity at MDSP to confirm vehicle state and connectivity.

One embodiment is directed towards a method of reporting use of a CMD in a distracting situation rather than to disable the CMD, therefore providing information that can be used monitor distracted use of the CMD without the need for control. In this embodiment, any event is record that indicates a CMD is in a vehicle that is in an unsafe state using techniques described herein. This recording can include additional information about the unsafe state, e.g., severity of event, etc. This information is compared with CMD usage records from the MDSP to identify uses of the CMD while in a vehicle. A report is created to incidences of CMD usage including associated elements such as location of use, velocity of vehicle etc.

One embodiment is directed towards a simple method of determining the CMD within the vehicle. In this embodiment, CMDs are registered or associated with a VDS. The CMD owner can to identify that they are driving, such as text message, phone call, opening an application on a CMD, or performing a function that can be sensed by the VDS and transmitted to the SDS such as tapping brakes a certain number of times, blinking lights a certain number of times. When an unsafe state is determined, and a driver has not been identified, disable all CMDs associated with that vehicle. When the driver self-identifies enable non-driver CMDs. Optionally, compare the location of the disabled CMD with the location of the vehicle to confirm the identity of the driver.

One embodiment is directed towards using self-policing to limit the number of CMDs disabled when multiple CMDs are in a vehicle, thereby lessening the need for override requests. In this embodiment, identify which CMDs are associated with low risk drivers (unlikely to use a distracting CMD with others in the vehicle) as well as CMDs associated with high risk drivers (likely to use a distracting CMD with others in the vehicle. When a single CMD is in the vehicle, disable all CMDs in the vehicle. When multiple CMDs are in the vehicle and one is a low risk driver, enable all CMDs. When multiple CMDs are in the vehicle and none are low risk drivers, disable all CMDs. Optionally, with multiple CMDs disable in a vehicle, allow all but one CMD to request an override.

One embodiment is directed towards using unique wireless signals transmitted from the CMD that can be received by the VDS to determine if a CMD is in a vehicle. In this embodiment, registered CMDs may be used within the vehicle to transmit a Unique Wireless Signal such as Bluetooth or other RF signal with a unique identifier. In a preferred embodiment the UWS is the transmission that the CMD utilizes to communicate with the MSDP and therefore does not require any additional RF transmission beyond that required for operation. Optionally the MSDP may provide information through various means to the VDS to enable it to decrypt the UWS. The registered CMDs are associated to a specific UWS by provisioning or by the VDS sensing the UWS with the known CMD in the vehicle. When a UWS is received while a vehicle is in an unsafe state, a notification is made that the CMD associated with the UWS should be disabled. Optionally, the presence of CMDs in the vehicle but with a UWS disabled can be verified by comparing the location of the CMDs with the location of the VDS or other means described herein. Optionally, an alert can be sent that a CMD has a disabled UWS, allowing it to be enabled.

One embodiment is directed towards using a unique wireless signal transmitted from the VNT to the CMD that can be received by the CMD and transmitted to the MSDP without the need for software on the CMD, or with minimal software on the CMD, so as to provide information via the MSDP as to the presence of a CMD in a vehicle in an unsafe state, allowing it to be disabled. Registered CMDs may be used within the vehicle. On detecting an unsafe state, the VNT transmits a unique wireless signal (UWS) including one or more of notice of the unsafe state, vehicle information associated with the unsafe state, the ID of the vehicle and the ID of the VDS and VNT. The UWS is able to be received by the CMD without any modifications or software, or alternately with minor modifications or software. In a preferred embodiment, the UWS is configured to be received by the CMD and retransmitted to the MSDP as part of normal CMD protocols. In a preferred embodiment frequency of UWS is same as frequency CMD uses to communicate with MSDP. In a preferred embodiment, UWS is configured to appear as a cell tower transmission, such as femtocell transmission, with identification information incorporated as an element of the UWS in the form of cell tower ID information, but in a manner that the CMD does not attempt to connect to the VNT as a cell tower. UWS information can then be transmitted to the MSDP via this cell tower ID information (or by other means). MDSP is operable to decode the UWS to determine vehicle ID, CMD ID, state of vehicle, and provide to the system described herein. The system is operable to combine with other information to determine if the CMD should be disabled.

In one preferred embodiment where it is desired to provide information for other purposes other than controlling a potentially distracting mobile device, a vehicle is equipped with a VDS that is operable to capture vehicle information for the purposes of establishing a more accurate insurance rate for the vehicle and at the same time improving the driving behavior of individuals by providing feedback as to their driving behavior. In this embodiment the VDS provides data related not only to the identification of CMDs within the vehicle as described herein, but optionally can provide one of more of vehicle, driver and CMD information related to evaluating the driving patterns of the vehicle and drivers so as to establish an accurate risk factor for the vehicle for insurance purposes (Insurance Rating Information, IRI), or for other commercial purposes. In this embodiment, the SDS is operable to capture IRI information provided by the VDS and store it on the SDD, or forward it directly to be used for insurance ratings purposes, while utilizing information provided by the VDS for disabling CMDs using techniques described herein. Alternately, VDS information can be captured by a third party (for example and insurance company) and information necessary for disabling CMDs using techniques described herein can be provided to the SDS or SDD. In an embodiment, techniques describe herein to determine if a CMD is in a vehicle, if an individual is in a vehicle, or a specific individual is driving, are used to determine one or more of the occupants of the vehicle during trips, the driver of the vehicle during trips, the driving behavior of individuals, the amount of driving by a particular individual, and other information of commercial value related to driving behavior and the identification of individuals that are passengers or drivers of the vehicles. This information can then be provided to insurance companies, or commercial vehicle owners, or such companies. to provide driver and vehicle passenger information that can be used for purposes of establishing more accurate insurance rates for that vehicle or individual, or for providing driving behavior feedback, or for determining favorable or unfavorable individuals or vehicles to insure. In another embodiment, the system and techniques described herein are used exclusively to determine this information without the incorporation of the elements of the system that actually control the potentially disabling electronic device.

In one embodiment, the method for capturing events that indicate the mobile device is or may be being used in a distracting manner by the driver can include indications such as the system is engaged or not while driving, e.g., game engaged, whether a distracted driving system has been overridden (FIG. 15 step 1516), whether distracting events have occurred during driving, and whether or not the driver has identified themselves as the driver at some point during the trip through such as identifying themselves via software on the CMD. The system can transmit a message via the CMD that identifies the driver, or combinations. In one embodiment, the method for identifying the geographic location of the unsafe events, including using location capability on VDS 35, or CMD 25, or combinations, can be transmitted.

Optionally or alternatively, the method for providing information and scoring on unsafe driving behavior to the driver, the subscriber to the system 10, or others electronically, including CMD 25 and User Interface 115, includes providing the score in "real time" at the end of the drive to the driver through the CMD. The method can include providing discounts, e.g., e-commerce incentives, to a user near a location of the user at the end of the trip, e.g., using the location of the vehicle provided by the system. The e-commerce incentives can be generated automatically by the system or in combination with partners, such as companies that are willing to provide discounts to safe drivers and include tangible rewards (such as a discount on a products), potentially in real time through the CMD, or through another user interface. The incentives can also be rewards that are provided to a third party, such as a charity. In one embodiment, the type of rewards can be selected from a list by the user so as to be highly motivating to improve driving behavior, or be previously selected to be highly motivating to a particular driving demographic and be incorporated into the game based on demographic information provided by the user during registration.

Figure 16:
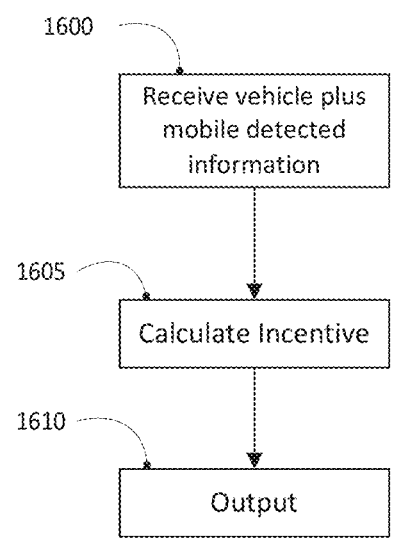
FIG. 16 discloses a flowchart of a simplified embodiment of a technique performed by the mobile services control system to generate a score of a game according to an embodiment.

In one embodiment, the Service Decision System 125 may be operational to connect with the CMD 25, VDS 35, Mobile Device Service Provider (MDSP) 130, Vehicle Service Provider VSP 100, or third-party source with network 60, network 45, data network 90, user interfaces 115 or other means to receive the vehicle plus mobile detected information. The vehicle plus mobile detected information may be received by the Service Decision System 125 periodically at set intervals or in a real-time near-continuous stream of data. Referring now to FIG. 16, a high level flowchart illustrates some of the steps in the service decision engine to generate a score based on predetermined parameters.

In this embodiment, the Safe Driving Registration System 105 (FIG. 1) is configured through one or more of the User Interfaces 115 (by a person and/or an automated input) with information specific to functionality of the game including game parameters, awards, discounts, and information specific to a user and/or a plurality of users, wherein the information includes: (i) game parameters for determining awards, discounts, and score, (ii) associations with other users or groups, and/or (iii) at least one primary operator of vehicle 15, or if multiple operators are scheduled for the vehicle, information specifying the times that a specific one of the operators will be operating the vehicle 15. Additionally, the Safe Driving Registration System 105 is provided (e.g., via a User Interface 115) with CMD information identifying which CMD 25 or CMDs 25 are associated with each of the operator(s), as well as information as to what incoming and outgoing calls, text messages or other information should be allowed for emergency use or otherwise while services to such CMD(s) are being controlled by the mobile services control system 10. Note that in this embodiment, the vehicle 15 incorporates a Vehicle Detection System (VDS) 30 that may or may not incorporate a Detection Engine 300 since the requirement you detect the location or position of an operator's CMD 25 within the vehicle occupant enclosure 20 may not be necessary.

Referencing FIG. 1 and the flowchart in FIG. 16, in step 1600, the Service Decision System 125 (and optionally Safe Driving Registration System 105) receives vehicle plus mobile detected information. This vehicle plus mobile detected information is used to calculate a score based (1605) on game parameters received from the Safe Driving Registration System 105. In one embodiment, the score is configured to promote safe driving behavior. The score includes one or more scores and can also be associated with awards, tokens (e.g., graphical pins and badges), and discounts (e.g., insurance discounts, e-commerce discounts, store discounts within a predetermined geographical distance, e.g., 5 miles or less based on CMD location, or VDS location, and monetary rewards). Various program logic can be used to calculate one or more scores, or generate one or more awards, or generate one or more discounts, and combinations of the same based on the one or more scores with the vehicle plus mobile detected information. The program logic is predetermined or provided real time via the system 10 (e.g., user interfaces 115). In one embodiment, the program logic is configured to determine the number of segments for the trip (e.g., calculated by equation: (minutes driven/predetermined segment minutes), the predetermined segment minutes may be any number greater than 1, e.g., 10 minutes, number of perfect segments (e.g., perfect driving streak calculated) and/or other desired scores configured to modify or motivate driving behavior (e.g., tokens, badges awarded on good driving, fuel efficient driving, etc.). Alternatively, the segments may be measured in distance driven rather than time driven, or a combination of time and distance to compensate for long trips at a slow speed, or short trips at high speed. The SDS 125 can also be configured to calculate bonuses, e.g., if a user self IDs, that is, notifies the system that they are the user of the vehicle 15. This may be done by a number of different ways, e.g., with the CMD 25, or VDS 35, or texting, or calling a number, or seat position, or flashing the lights on the vehicle or some other indication that a particular individual is driving the vehicle. That is, the user, subscriber or third-party can specify a predetermined way to identify the user. The bonuses may be any type of bonus, e.g., increased score percentage, awards, discounts, combinations of the same and the like. In one embodiment, one or more of the following can be generated or obtained by the system, including but not limited to a total bonus calculated by summing all bonuses, a basic score calculated by equation (number of perfect driving×predetermined number (e.g., 1000), a total score calculated by equation (basic score×total bonus), an average score per segment per user, or per team, or per social group and combinations, a cumulative score per segment/mile, and/or a driving time per segment. In addition, one or more of the following can be generated or obtained by the system, including but not limited to a distance and miles, number of braking events (hard braking or excessive braking) above a predetermined g-force number with or without location of the event, a number of hard turn events (hard corners or excessive cornering) above a predetermined g-force number with or without location of the event, a number of acceleration events above a predetermined limit, variations in speed indicative of distracted driving, whether one or more disabled service was overridden (e.g., CMD User Override), number of times above the speed limit with or without location is determined with system 10, and/or other information indicating fuel economy of vehicle is presented in a score. In one embodiment, the score, or bonuses, or rewards, or discounts and/or combinations can be calculated with predetermined rules or programs provided by a user, or a subscriber and/or a third-party to the Safe Driving Registration System 105. Optionally or alternatively, the incentive is configured to reward sequential periods of safe driving by providing a multiplier to the base score such that for an individual who has a history of sequential safe driving, the point score increases more rapidly, further incentivizing safe driving.

The service decision engine may receive vehicle plus mobile detected information from one or more of CMD 25, VDS 35, and external inputs outside the vehicle. The information may be provided in real time, at predetermined intervals or after use of the vehicle 15. If the vehicle 15 is not in operation (as determined in step 710) the service decision engine 600 sends an enable services directive to either the MDSP 130 or the SDRS 110, depending on how it is configured (disclosed in FIG. 1). Conversely, if the vehicle is in operation (as determined in step 710) and the option to check for CMD 25 positioning relative to the restricted zone (step 715) is off, then the service decision engine 600 sends a disable services directive (step 725) to either the MDSP 130 or the SDRS 110. Alternately, if the vehicle 15 is in operation (as determined in step 710), the option to check for CMD positioning is on (step 715), and the CMD 25 is within the restricted zone of the vehicle (as determined in step 720), then the service decision engine 600 sends a disable services directive in step 725, or if the CMD is outside the restricted zone, then the service decision engine 600 sends an enable services directive in step 730. Regardless, after the service decision engine 600 sends the appropriate enable/disable service directive, it waits a predetermined amount of time in step 700 (e.g., a minute or two, or perhaps even seconds) before repeating the process and receiving updated vehicle plus mobile detected information in step 705. The service directive may specify individual services, direct all services (except emergency response services), direct disabling the battery on the CMD (which in turn, would prevent operation of the CMD), directly disable all functions on the CMD, or send a warning message to the user of the CMD and/or to the subscriber.

In step 1605, the Service Decision System 125 (and optionally the Safe Driving Registration System 105) received vehicle is configured to output the incentive including one of a score, or rewards, or bonus, or discounts and combinations of the same to the CMD 25, VDS 35, user interface 115, social media, portal, internet, subscriber, operator, or third party. In this embodiment, the output is done with the system 10 over a network (e.g., wireless network 45, wireless network 65, data network 90, other network or combinations therein). The output to the CMD 25 may be substantially instantaneous after the trip or at any predetermined time after the trip, e.g., when instantaneous, at key off of the vehicle 15. Outputs may include multimedia, sound, video and combinations thereof. In one embodiment, upon key off an incentive is audibly generated by the SDS 125 in step 1605 and sent to a CMD 25 and/or vehicle 15 to provide relatively instant feedback to the user. Moreover, the output may be sent via an application on the CMD 25 or other device accessible via internet to a graphical user display (e.g., in one embodiment as described with reference to FIGS. 18-20 herein), social medial, stored in a database of SDRS 105, and/or other outputs. These outputs can be predetermined to include emails, SMS, texts and the like.

Figure 17:
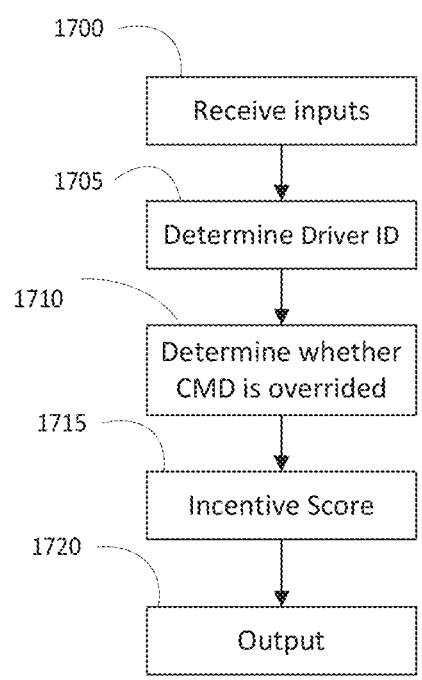
FIG. 17 discloses a flowchart of a simplified embodiment of a technique performed by the mobile services control system to generate a score of a game according to an embodiment.

Referencing FIG. 1 and the flowchart in FIG. 17A, in step 1700, the Service Decision System 125 (and optionally the Safe Driving Registration System 105) receives one or more inputs including vehicle plus mobile detected information. This information may be provided after a vehicle trip or by any system including a CMD 25 and a vehicle 15, e.g., a third party system. In step 1705 a driver ID is determined as described previously via the associated information, or the driver ID may be self identified, or may be identified by another technique as known in the art. The CMD 25, or the SDS 125, or combinations thereof is configured to determine whether any restricted service on the CMD has been overridden, (e.g., CMD User Override). An incentive is generated in step 1715, e.g., a score, or a reward, or a discount, or a token, and combinations thereof. Next, in step 1720, an output may be sent via an application on the CMD 25 or other device accessible via internet to a graphical user display (e.g., in one embodiment as described with reference to FIGS. 18-20 herein), social medial, stored in a database of SDRS 105, and/or other outputs.

In one embodiment, the incentive, e.g., score, and method can include a method for capturing unsafe driving events that can include swerving, excessive speed, abrupt braking either wirelessly from the vehicle, or from a mobile device associated with the driver utilizing the Vehicle Detection System (VDS) 35.

In one embodiment, the service decision engine 125 is configured to determine when a vehicle is moving, who the are passengers in the vehicle are and who is the driver of the vehicle 15; receive inputs from the vehicle 15 or CMD 15; and determine the location and occurrence of unsafe events. The SDS 125 determines a score for the driver using the system 10, as well as calculates other data that will improve the efficacy of the system to modify driving behavior. Optionally or alternatively, the incentives, e.g., score, may be generated on a game engine external to the system, (e.g., FIG. 1, 10), or on the CMD 25, or VDS 35, or in any combination.

Figure 18:
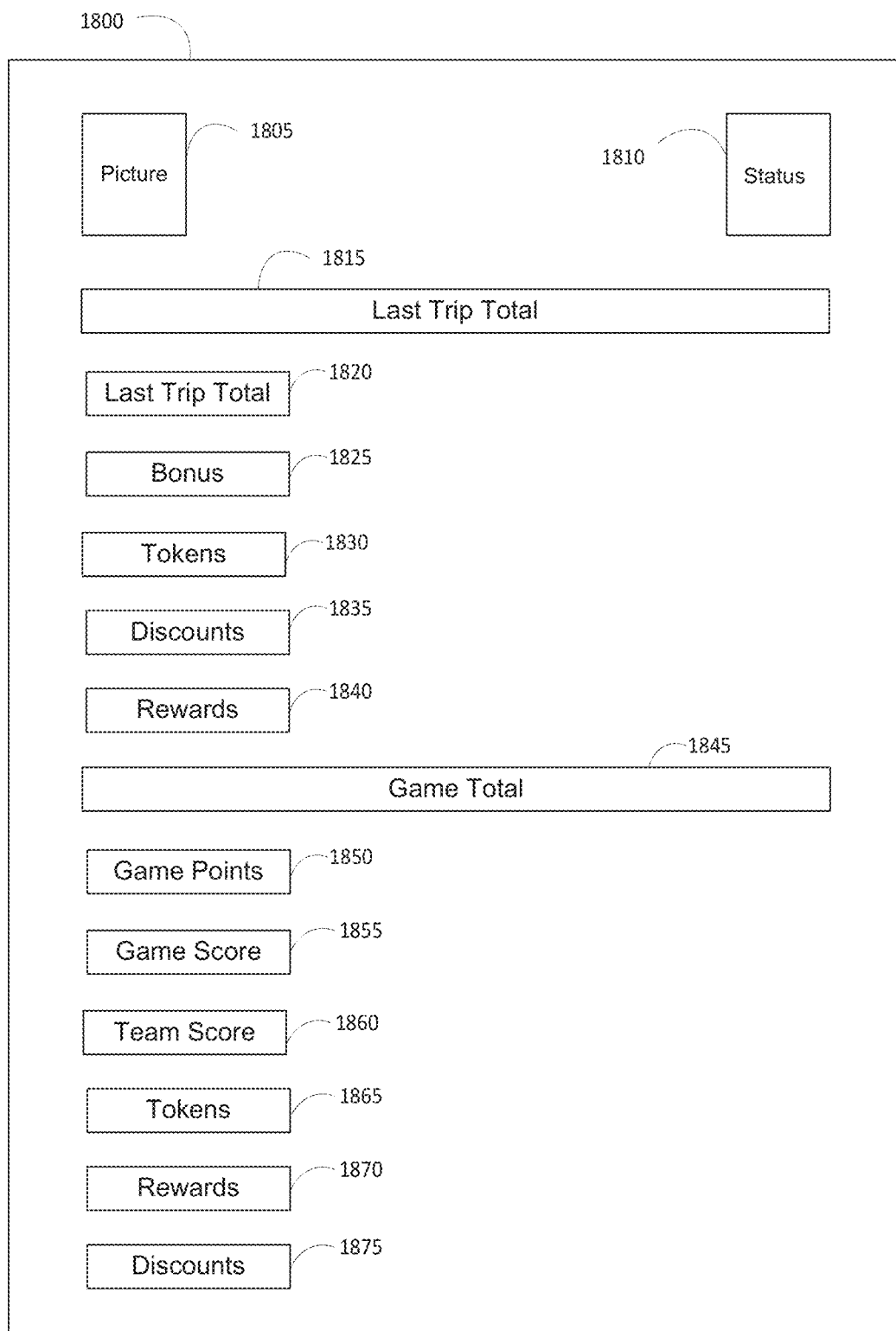
FIG. 18 discloses a simplified screen shot of an output of the system according to an embodiment.
Figure 19:
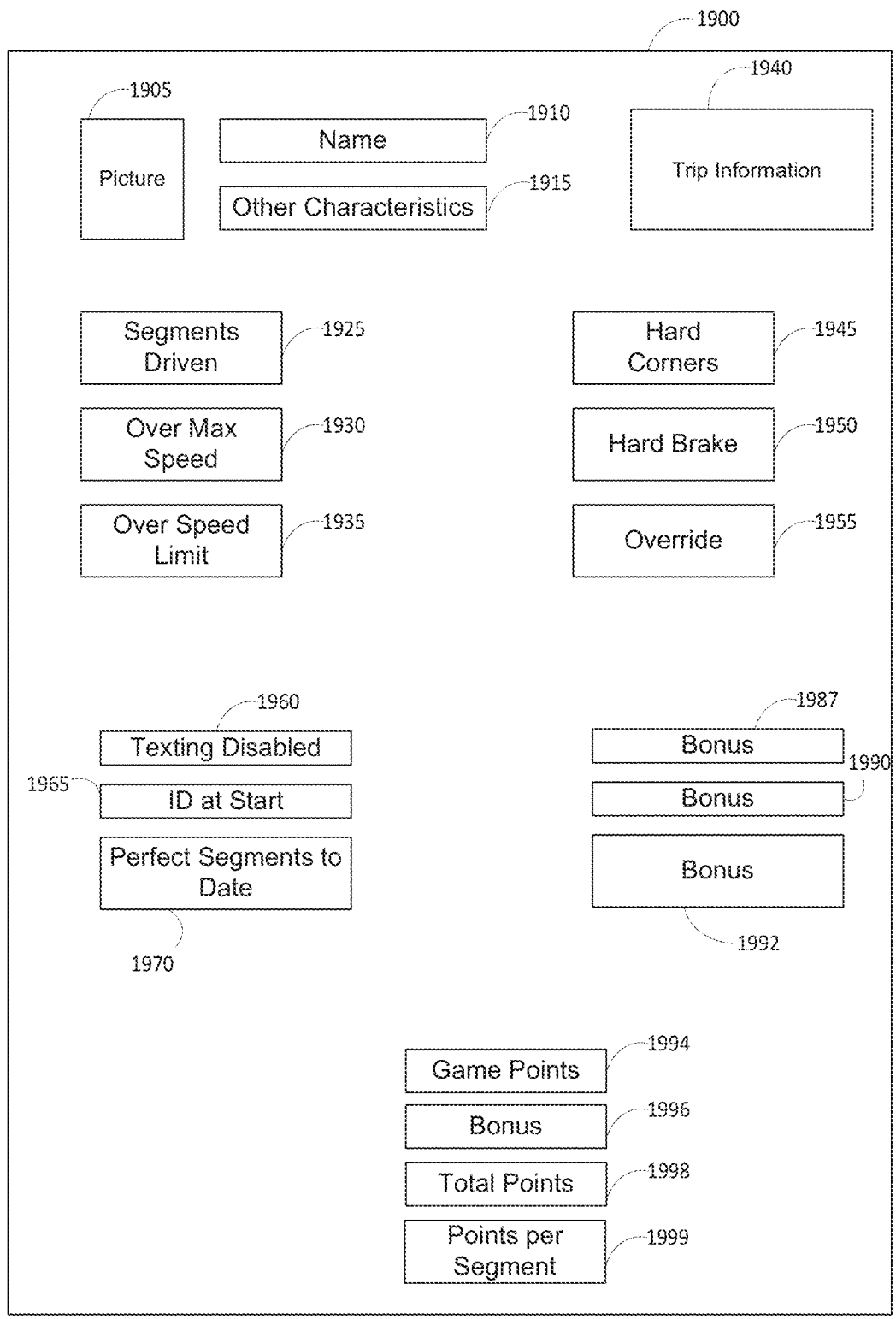
FIG. 19 discloses a simplified screen shot of an output of the system according to an embodiment.
Figure 20:
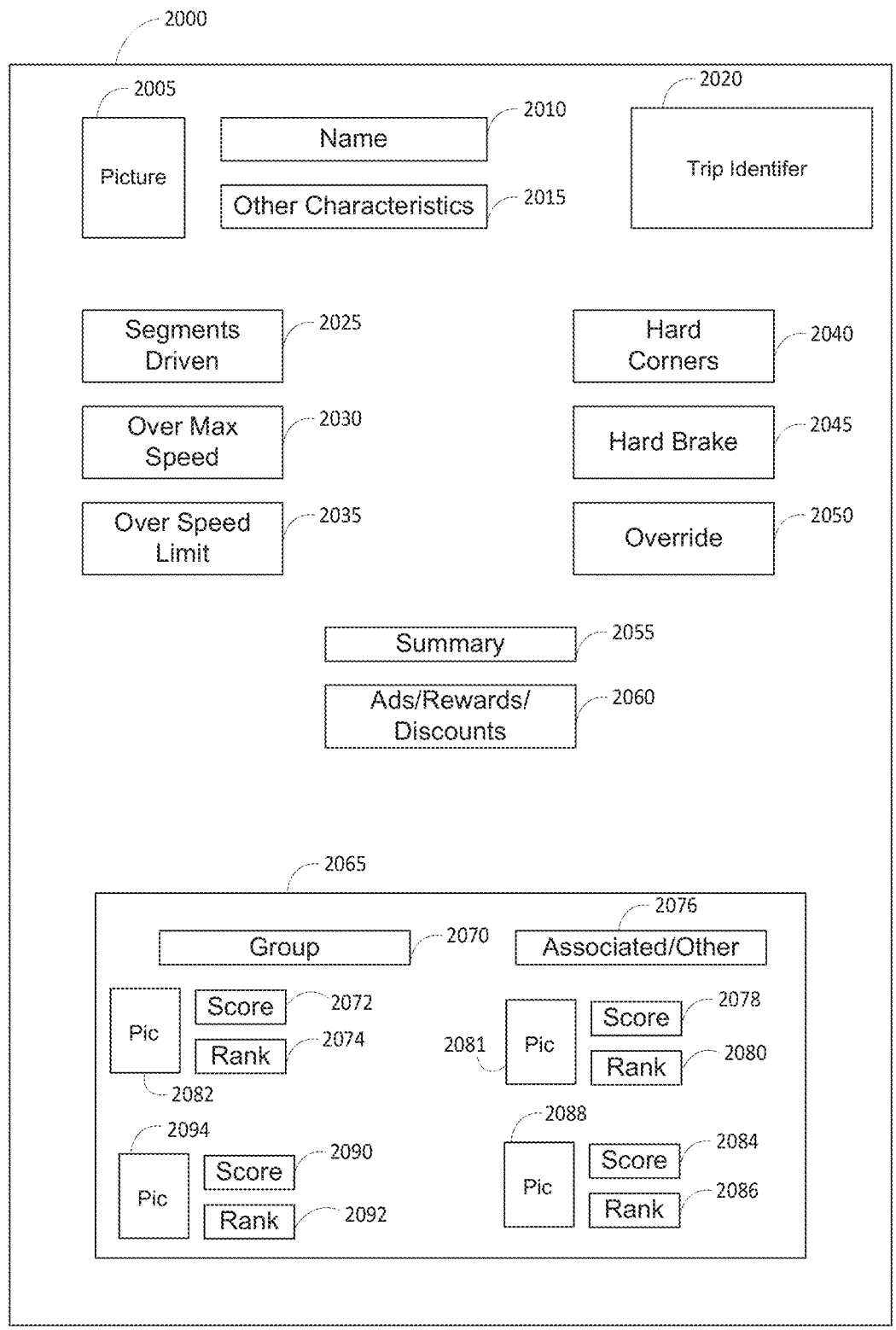
FIG. 20 discloses a simplified screen shot of an output of the system according to an embodiment.

FIGS. 18-20 illustrates an exemplary embodiments with regard to a graphical outputs of various screen shots of the game. In this embodiment, the screen shots 1800, 1900, and 2000 may include web portal screen shots and/or CMD application screen shots. These are representative examples of outputs, e.g., steps 1610 and 1720.

Referring now in detail to FIG. 18, the screen shot 1800 may be a home screen of the application, e.g., game. This can be visible to the user, subscriber and/or third-party. It includes a picture 1805 of the user or symbol that can be provided to the SDRS 105 and stored in the SDD 110. A real time status 1810 (e.g., I'm Driving Now, or other programmable text) of the user can be displayed. A most recent trip identifier 1815 is shown to indicate or associate the most recent trip incentive, e.g., scores. For example, the score can include any as described herein and in this embodiment includes a last trip total 1820, bonus 1830, discounts 1835 and rewards 1840. The discounts 1835 and rewards 1840 can be automatically generated by matching the current location of the user, available discounts and rewards, and preferences of the user or subscriber. A game total section 1845 includes a user's game total for the year or other predefined time period. In this embodiment, the section includes game total points 1850, game total score 1855, team score 1860, e.g., a summary of other users selected or assigned to the team, one or more tokens 1865, rewards 1870, and discounts 1875. Optionally or alternatively, the rewards 1870 and/or discounts 1875 display may include the number of points required to earn the next reward or discount.

Optionally or alternatively, one or more of the items may include outputting to social media to allow broad dissemination as well as enable different forms of games, competitions and rewards for individuals or teams. The data may also include scoring the driving behavior of the driver based on the number of unsafe events during a drive and be presented to the driver as a game that optionally may allow other drivers' scores to be compared for the purposes of competition, such as scoring changing the behaviors of the drivers from the desire to improve the score.

Referring now in detail to FIG. 19, the screen shot 1900 may be a detailed last trip screen of the application, e.g., game. This can be visible to the user, subscriber and/or third-party. It includes a picture 1905 of the user or symbol that can be provided to the SDRS 105 and stored in the SDD 110, a user name 1910, and other user characteristics 1915 (e.g., phone number, email, and the like), and a trip information 1940 identifier (e.g., description of trip, or name of trip). The screen shot 1900 can also include the score as described herein and in this embodiment includes indication of segments driven 1925; indication of segments over maximum speed 1930; indication of segments over the speed limit 1935; indication of corners exceeding a predetermined g-force 1945; indication of number of hard braking exceeding a predetermined g-force 1950; indication of CMD User Override 1955; an indication of a texting disabled event 1960 and an indication of associated bonus 1987; an indication of whether the user provided a self-identification at the trip (e.g., during, before, and/or after the trip) and an indication of associated bonus 1990; and an indication of number of segments driven 1970 and an indication of associated bonus 1992. In one embodiment, the indications may include any combination of alpha numeric text, or a whole number, or a fraction number, or a color or combination of primary colors, or a graphic, or a combination of one or more of the same. It is noted that any incentive may be displayed in this screen and these are shown merely as an illustrative embodiment. Optionally or alternatively, one or more of the items in screen shot 1900 may be output to social media to allow broad dissemination as well as enable different forms of games, competitions and rewards for individuals or teams. The data may also include scoring the driving behavior of the driver based on the number of unsafe events during a drive and be presented to the driver as a game that optionally may allow other drivers scores to be compared for the purposes of competition, such scoring changing the behaviors of the drivers from the desire to improve the score.

Referring now in detail to FIG. 20, the screen shot 2000 may be a detailed summary of the user's last trip, or total trips over a predetermined time. The screen shot 2000 also includes a comparison section 2065 of other team members, highest ranking drivers, selected friends and/or other users. This screen shot 2000 can be visible to the user, subscriber and/or a third-party. It includes a picture 2000 of the user or symbol that can be provided to the SDRS 105 and stored in the SDD 110, a user name 2010, and other user characteristics 2015 (e.g., phone number, email, and the like) and a trip information identifier 2020 (e.g., description of trip, or name of trip). The screen shot 2000 can also include the score as described herein and in this embodiment includes indication of segments driven 2025, indication of segments over maximum speed 2030, indication of segments over speed limit 2035, indication of corners exceeding predetermined g-force 2040, indication of number of hard braking exceeding a predetermined g-force 2045, indication of CMD User Overrride 2050, an indication of total of points 2055, and an indication of rewards, discounts, advertisements 2060 or any combination. In one embodiment, the indications may include any combination of hyperlinks to a separate webpage, or document, alpha numeric text, or a whole number, or a fraction number, or a color or combination of primary colors, or a graphic, or a combination of one or more of the same. Section 2065 includes data, e.g., scoring, indicative of behavior of the driver based on the number of unsafe events during a drive in which the score is presented to the driver as a game that optionally may allow other drivers scores to be compared for the purposes of competition, such as scoring changing the behaviors of the drivers from the desire to improve the score. In this embodiment, the section 2065 includes an indication of the group 2070 (e.g., company name, sport's team name, etc.), a picture or graphic of a team member 2082, an indication of score 2072, an indication of rank 2074, a picture or graphic of the next team member 2094, an indication of score 2090 associated with member 2094, an indication of rank 2092 associated with member 2094, and optionally other members (not shown). Indication 2076 may include all time highest ranking users, or team members or the like. In this embodiment, a picture or graphic of a team member 2081, an indication of score 2078, an indication of rank 2080, a picture or graphic of the next associated member 2088, an indication of score 2084 associated with member 2088, an indication of rank 2086 associated with member 2088, and optionally other members (not shown). Optionally or alternatively, one or more of the items my include outputting to social media to allow broad dissemination as well as enable different forms of games, competitions and rewards for individuals or teams.

While various embodiments of the present disclosure have been described in detail, it is apparent that modifications and alterations of those embodiments will occur to those skilled in the art. However, it is to be expressly understood that such modifications and alterations are within the scope and spirit of the present disclosure, as set forth in the following claims.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the disclosure.

Moreover, though the present disclosure has included description of one or more embodiments and certain variations and modifications, other variations and modifications are within the scope of the disclosure, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A mobile services control system for generating a score based on driving events and use of a controllable mobile device, comprising:
   an in-vehicle detection system configured to determine one or more characteristics of a vehicle indicative of the vehicle being operated by a user; and
   a computational equipment that is configured to generate the score based on a first input indicative of whether a controllable mobile device is within the vehicle when the vehicle is in operation, a second input comprising the one or more characteristics of a vehicle indicative of the vehicle being operated by a user, and a third input indicative of one or more of a use of the controllable mobile device by the user, a use of the system that controls distracting use of the controllable mobile device, overriding the system and one or more events indicative of driving behaviors, wherein the system is configured to communicate one or more rewards to a user based on the score and wherein the computational equipment is configured to communicate, during or after the end of a trip, one or more of an audible, vibrational or visible alert to the user to indicate that the score has been achieved.

2. The mobile services control system of claim 1, wherein the use of the controllable mobile device comprises one or more of reviewing text message, typing a text message, voice call, sending a text message, reviewing an email message, typing a text message, sending an email, playing a game, viewing a video, information provided via the Internet and interaction with an interface of the controllable mobile device.

3. The mobile services control system of claim 1, further comprising a memory.

4. The mobile services control system of claim 1, wherein the score is indicative of a driving behavior of the user.

5. The mobile services control system of claim 4, wherein the score comprises one or more of a number of excessive cornering events, a number of excessive braking events, a number of excessive acceleration events, use of the system to control distracting features of a mobile device while driving, a number of overrides of the system to control distracting features of a mobile device while driving, a number of segments, of a specified distance, driven without an event indicative of unsafe driving, a number of segments, of a specified time, driven without an event indicative of unsafe driving, a number of incidences of exceeding a predetermined maximum velocity, a number of incidences of exceeding a speed limit, a number of miles driven, an indication that a user identified themselves as a driver, and vehicle speed variation over distance and time.

6. The mobile services control system of claim 1, wherein the score is indicative of distracted driving behaviors.

7. The mobile services control system of claim 1, wherein the score is configured to encourage a desired driving behaviors by optimizing scores or rewards.

8. The mobile services control system of claim 1, wherein the score is calculated using scoring techniques based on score multipliers for desirable behaviors and score multipliers for sequential periods of driving with the desired behavior, and wherein the score includes one or more of badges and awards and is configured to encourage competition between users.

9. The mobile services control system of claim 1, wherein the score comprises one or more of a trip score, a cumulative score for a period, game information, and a reward.

10. The mobile services control system of claim 1, wherein the computation equipment is configured to generate a reward based on the first input, the second input and the third input, wherein the reward includes one or more of discounted merchandise, free merchandise, services, and a donation that can be given to third party specified by the user.

11. The mobile services control system of claim 10, wherein the score further comprises one or more of a reward or a discount based on data including one or more characteristics indicative of the one or more services being used, a location of the vehicle and driving behavior of the user.

12. The mobile services control system of claim 1, wherein the computation equipment is configured to generate a reward based on the first input, the second input and the third input, wherein the reward includes one or more of a reward based on a location of the vehicle, a location of redemption based on the location of the vehicle, a redemption location provided to the user concurrently with the reward, and an expiration time for the reward.

13. The mobile services control system of claim 1, wherein the score is calculated using scoring techniques based on one or more score multipliers for desirable behavior and score multipliers for sequential periods of driving with the desired behavior.

14. The mobile services control system of claim 1, wherein the system is configured to allow the user to preselect awards that will be particularly motivating in changing the behavior of the user.

15. The mobile services control system of claim 1, further comprising a communication unit configured to communicate the score to one or more of a subscriber, a social media, the controllable mobile device, and a third-party.

16. The mobile services control system of claim 1, wherein the computation equipment resides at least in part on one or more of the controllable mobile device, a wireless a vehicle vibration indicative of vehicle movement.

17. The mobile services control system of claim 1, wherein the computation equipment is configured to communicate with the controllable mobile device.

18. The mobile services control system of claim 1, wherein the computation equipment is configured to compare scores among one or more users of the system so as to create competition among the users.

19. The mobile services control system of claim 1, wherein the computation equipment is configured to programically deduce whether the user has overridden a disabled feature or a disabled service of the controllable mobile device.

20. The mobile services control system of claim 1, wherein the score comprises a number of segments driven by the user.

21. The mobile services control system of claim 20, wherein at least one of the segments is selected from a group consisting of a length of time, a distance, and combinations thereof.

22. The mobile services control system of claim 1, wherein the score comprises a discount including a financial vehicle insurance discount.

23. The mobile services control system of claim 1, wherein the score comprises a reward including an e-commerce discount based on a location of the vehicle.

24. The mobile services control system of claim 1, wherein the in-vehicle detection system receives vehicle movement data from one or more vehicle movement detectors, the movement detectors detecting one or more of a vehicle acceleration, velocity, and the vehicle, services are restricted to the controllable movable device by one or more of notifying the provider to restrict services or transmitting a signal to the controllable movable device to restrict services.

25. The mobile services control system of claim 1, further comprising a communication interface configured to intermittently transmit additional data external to the vehicle.

26. The mobile services control system of claim 1, wherein the use of the controllable mobile device comprises texting.

27. The mobile services control system of claim 1, wherein the in-vehicle detection subsystem comprises a wireless Bluetooth interface.

28. The mobile services control system of claim 1, wherein the computational equipment comprises a data management system for storing identifications of: (i) a subscriber for subscribing to the mobile services control system, (ii) the controllable mobile device wherein the controllable mobile device is identified with the subscriber, and (iii) the vehicle or the in-vehicle detection subsystem.

29. The mobile services control system of claim 28, wherein the data management system provides the first and second input to at least one component of the computational equipment for determining one of: when the controllable mobile device is within a predetermined geospatial envelope, and when a predetermined vehicle movement is detected.

30. The mobile services control system of claim 1, wherein the computational equipment uses a communication between the controllable mobile device and one or more base stations for a wireless service provider to determine a particular location of the controllable mobile device, and a communication between an interface and a wireless network for determining a particular location of the vehicle when the location of the controllable mobile device and vehicle are determined to be such that the controllable mobile device is within network, and a wireless service provider.

31. The mobile services control system of claim 30, wherein one of a signal strength, a signal time delay, an identification of one of the base stations and gps location is used in determining the particular location of one or more of the controllable mobile device and the vehicle.

32. The mobile services control system of claim 30, wherein a signal strength, a signal time delay, an identification of one of the base stations of a wireless network and gps is used in determining the particular location of the vehicle or the in-vehicle detection subsystem.

33. The mobile services control system of claim 1, wherein the one or more characteristics of a vehicle indicative of the vehicle being operated by a user comprises one or more of information indicative of unsafe driving behaviors and information indicative of distracted driving behaviors.

34. The mobile services control system of claim 1, wherein the one or more characteristics of a vehicle indicative of the vehicle being operated by a user comprises one or more of information indicative excessive cornering, information indicative of excessive braking, information indicative of swerving, information indicative of acceleration, information indicative of uneven speed maintenance, and information indicative of speeding.

35. The mobile services control system of claim 1, wherein the controllable mobile device moves independently from the in-vehicle detection subsystem.

36. The mobile services control system of claim 1, wherein the computation equipment at least partially resides in a cloud.

37. The mobile services control system of claim 1, wherein the first input comprises data including one or more of data indicative of the controllable mobile device being associated with the vehicle, data indicative of the controllable mobile device being scheduled to be in the vehicle, and data indicative of the controllable mobile device being associated with the user who is associated with the vehicle.

38. The mobile services control system of claim 1, wherein the use of the system that controls distracting use of the controllable mobile device comprises one or more of monitoring the controllable mobile device, disabling the controllable mobile device, disabling one or more service of the controllable mobile device and reporting on usage of the controllable mobile device.

39. The mobile services control system of claim 1, wherein the reward is an intangible reward.

40. The mobile services control system of claim 39, wherein the intangible award is selected from a group consisting of badges, personal scores, team scores, competitors scores, recognition on social media, public acknowledgement, networked communication and combinations.

41. The mobile services control system of claim 1, wherein the reward is a tangible award.

42. The mobile services control system of claim 41, wherein the tangible award comprises one or more of an economic incentive and a product of value.

43. The mobile services control system of claim 41, wherein the product of value comprises a discount on automobile insurance.

44. The mobile services control system of claim 1, wherein the reward comprises a tangible award and an intangible award.

45. A mobile services control system for generating a score based on driving events, comprising:
computational equipment that is configured to generate the score based on a first input indicative of whether a mobile communication device is within the vehicle when the vehicle is in operation, a second input comprising the one or more characteristics indicative of the vehicle being operated by a user, and a third input indicative of one or more of a use of the controllable mobile device, a use of the system that prevents unsafe use of the controllable mobile device, overriding the system that prevents unsafe use of the controllable mobile device, and unsafe driving events, and wherein the computational equipment is configured to communicate, during or after the end of a trip, one or more of an audible, vibrational or visible alert to the user to indicate that a particular award or score has been achieved.

46. The mobile services control system of claim 45, wherein the system is configured to communicate one or more rewards to a user based on the score.

47. The mobile services control system of claim 45, wherein the score is indicative of a driving behavior of the user.

48. The mobile services control system of claim 45, rein the score comprises one or more of a number of excessive cornering events, a number of excessive braking events, a number of excessive acceleration events, use of the system to control distracting features of a mobile device while driving, a number of overrides of the system to control distracting features of a mobile device while driving, a number of segments, of a specified distance, driven without an event indicative of unsafe driving, a number of segments, of a specified time, driven without an event indicative of unsafe driving, a number of incidences of exceeding a predetermined maximum velocity, a number of incidences of exceeding a speed limit, a number of miles driven, an indication that a user identified themselves as a driver, and vehicle speed variation over distance and time.

49. The mobile services control system of claim 45, wherein the score is configured to encourage a desired driving behaviors by optimizing scores or rewards.

50. The mobile services control system of claim 45, wherein the score is calculated using scoring techniques based on score multipliers.

51. The mobile services control system of claim 45, wherein the system is configured to communicate one or more rewards to a user based on the score.

52. The mobile services control system of claim 45, wherein the score comprises one or more of a trip score, cumulative score for a period, game information, and rewards for desired behavior are made available to the user at the end of each driving event.

53. The mobile services control system of claim 45, wherein the computation equipment is configured to generate a reward based on the first input, the second input and the third input, wherein the reward includes one or more of discounted merchandise, free merchandise, services, and a donation that can be given to third party specified by the user.

54. The mobile services control system of claim 45, wherein the computation equipment is configured to generate a reward based on the first input, the second input and the third input, wherein the reward includes one or more of a reward based on a location of the vehicle, a location of redemption based on the location of the vehicle, a redemption location provided to the user concurrently with the reward, and an expiration time for the reward.

55. The mobile services control system of claim 45, wherein the score is calculated using scoring techniques including one or more of calculating score based on score multipliers for desirable behavior, score multipliers for sequential periods of driving with the desired behavior, badges or awards, competitions between teams, leader boards, random rewards for a given behavior, and publication on social media.

56. The mobile services control system of claim 45, wherein the system is configured to allow a user to preselect awards that will be motivating in changing the users behavior.

57. The mobile services control system of claim 45, further comprising a communication unit configured to communicate the score to one or more of a subscriber, a social media, the controllable mobile device, and a third-party.

58. The mobile services control system of claim 45, further comprising an in-vehicle detection system comprising a wireless Bluetooth interface.

59. The mobile services control system of claim 58, wherein the in-vehicle detection system and the controllable mobile device communicate with the Bluetooth interface on an over-the-air connection.

60. The mobile service control system of claim 59, wherein the communication on the over-the-air connection comprises the one or more characteristics indicative of the vehicle being operated by a user.

61. The mobile services control system of claim 45, further comprising a wireless Bluetooth interface.

62. The mobile services control system of claim 45, wherein the computation equipment is configured to programically deduce whether the user has overridden a disabled feature or a disabled service of the controllable mobile device.

63. The mobile services control system of claim 45, wherein the first input comprises data including one or more of data indicative of the controllable mobile device being associated with the vehicle, data indicative of the controllable mobile device being scheduled to be in the vehicle, and data indicative of the controllable mobile device being associated with the user who is associated with the vehicle.

64. The mobile services control system of claim 45, further comprising a communication interface configured to intermittently transmit additional data external to the vehicle.

65. The mobile services control system of claim 45, wherein the computation equipment at least partially resides in a cloud.

66. A mobile services control system comprising:
an in-vehicle detection system configured to determine one or more characteristics of a vehicle indicative of the vehicle being operated by a user; and
a computational equipment configured to identify a user of the vehicle, restrict one or more services of the controllable mobile device, and generate the score, wherein the score is based on a first input indicative of whether a controllable mobile device is within the vehicle when the vehicle is in operation, a second input comprising the one or more characteristics of a vehicle indicative of the vehicle being operated by a user, and a third input indicative of one or more of a use of the controllable mobile device, a use of the system that prevents unsafe use of the controllable mobile device, overriding the system that prevents unsafe use of the controllable mobile device, and unsafe driving events, wherein the computation equipment is configured to generate a reward based on the first input, the second input and the third input, wherein the reward includes one or more rewards based on one or more of a location of the vehicle, a location of redemption based on the location of the vehicle, a redemption location provided to the user concurrently with the reward, and an expiration time for the reward.

67. The mobile services control system of claim 66, wherein the system is configured to allow the user to preselect awards.

68. The mobile services control system of claim 66, wherein the computation equipment is configured to programically deduce whether the user has overridden a disabled feature of the controllable mobile device or a disabled service of the controllable mobile device.

69. The mobile services control system of claim 66, further comprising a communication interface configured to intermittently transmit additional data external to the vehicle.

70. The mobile services control system of claim 66, wherein the computation equipment at least partially resides in a cloud.

71. The mobile services control system of claim 66, wherein the first input comprises data including one or more of data indicative of the controllable mobile device being associated with the vehicle, data indicative of the controllable mobile device being scheduled to be in the vehicle, and data indicative of the controllable mobile device being associated with the user who is associated with the vehicle.

72. The mobile services control system of claim 66, wherein the system is configured to communicate one or more rewards to a user based on the score.

73. The mobile services control system of claim 66, further comprising an in-vehicle detection system comprising a wireless Bluetooth interface.

74. The mobile services control system of claim 66, wherein the in-vehicle detection system and the controllable mobile device communicate with the Bluetooth interface on an over-the-air connection.

75. The mobile services control system of claim 66, wherein the communication on the over-the-air connection comprises the one or more characteristics indicative of the vehicle being operated by a user.

76. The mobile services control system of claim 66, further comprising a wireless Bluetooth interface.

\* \* \* \* \*